US010526418B2

(12) United States Patent
Shi

(10) Patent No.: US 10,526,418 B2
(45) Date of Patent: Jan. 7, 2020

(54) MODULATORS OF ACYL-COA LYSOCARDIOLIPIN ACYLTRANSFERASE 1 (ALCAT1) AND USES THEREOF

(71) Applicant: The Penn State Research Foundation, University Park, PA (US)

(72) Inventor: Yuguang Shi, Hershey, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 15/651,758

(22) Filed: Jul. 17, 2017

(65) Prior Publication Data

US 2017/0320964 A1  Nov. 9, 2017

Related U.S. Application Data

(62) Division of application No. 14/378,525, filed as application No. PCT/US2013/026311 on Feb. 15, 2013, now Pat. No. 9,708,411.

(60) Provisional application No. 61/599,496, filed on Feb. 16, 2012.

(51) Int. Cl.
| C07K 16/40 | (2006.01) |
| A61K 38/17 | (2006.01) |
| A61K 38/46 | (2006.01) |
| A61K 39/395 | (2006.01) |
| C12N 15/113 | (2010.01) |
| C12Q 1/6883 | (2018.01) |
| A61K 39/00 | (2006.01) |

(52) U.S. Cl.
CPC .......... *C07K 16/40* (2013.01); *A61K 38/1709* (2013.01); *A61K 38/46* (2013.01); *A61K 39/3955* (2013.01); *C12N 15/1137* (2013.01); *C12Q 1/6883* (2013.01); *A61K 2039/505* (2013.01); *C07K 2317/21* (2013.01); *C07K 2317/24* (2013.01); *C07K 2317/76* (2013.01); *C12N 2310/111* (2013.01); *C12Q 2600/136* (2013.01); *C12Q 2600/158* (2013.01); *C12Y 306/05* (2013.01)

(58) Field of Classification Search
None
See application file for complete search history.

(56) References Cited

U.S. PATENT DOCUMENTS

| 3,645,090 A | 2/1972 | Mochizuki et al. |
| 3,940,475 A | 2/1976 | Gross |
| 4,302,204 A | 11/1981 | Wahl et al. |
| 4,358,535 A | 11/1982 | Falkow et al. |
| 5,288,514 A | 2/1994 | Ellman |
| 5,474,796 A | 12/1995 | Brennan |
| 5,506,337 A | 4/1996 | Summerton et al. |
| 5,519,134 A | 5/1996 | Acevedo et al. |
| 5,525,735 A | 6/1996 | Gallop et al. |
| 5,539,083 A | 7/1996 | Cook et al. |
| 5,549,974 A | 8/1996 | Holmes |
| 5,569,588 A | 10/1996 | Ashby et al. |
| 5,593,853 A | 1/1997 | Chen et al. |
| 5,605,662 A | 2/1997 | Heller et al. |
| 6,127,159 A | 10/2000 | Fuller et al. |
| 6,140,067 A * | 10/2000 | Anderson ............ C12Q 1/6883 435/14 |
| 2002/0086356 A1 | 7/2002 | Tuschl et al. |

FOREIGN PATENT DOCUMENTS

| EP | 63879 B1 | 11/1989 |
| GB | 2019404 | 12/1982 |
| GB | 2034323 | 1/1983 |
| WO | WO8403564 | 9/1984 |
| WO | WO9119735 | 12/1991 |
| WO | WO9200091 | 1/1992 |
| WO | WO9320242 | 10/1993 |
| WO | WO9323569 | 11/1993 |
| WO | WO9525116 | 9/1995 |
| WO | WO9535505 | 12/1995 |

OTHER PUBLICATIONS

Kozal, M. et al, "Extensive polymorphisms observed in HIV-1 Glade B protease gene using high-density oligonucleotide arrays", Nat. Med., vol. 2(7), pp. 753-759, (Jul. 1996) Abstract.
Chen, H. et al, "Mitochondrial fusion is required for mtDNA stability in skeletal muscle and tolerance of mtDNA mutations", Cell, vol. 141, pp. 280-289, (Apr. 2010).
Martins De Brito, O. et al, "Mitofusion 2 tethers endoplasmic reticulum to mitochondria", Nature, vol. 456, pp. 605-610, (Sep. 2004) Abstract.
Li, J. et al, "Cardiolipin remodeling by ALCAT1 links oxidative stress and mitochondrial dysfunction to obesity", Cell Metab., vol. 12(2), pp. 154-165, (Aug. 2010).
Gebert, N. et al, "Mitochondrial cardiolipin involved in out-membrane protein biogenesis: implications for Barth syndrome", Current Biology, vol. 19, pp. 2133-2139, (Dec. 2009).
Bach, D. et al, "Mitofusion-2 determines mitochondrial network architecture and mitochondrial metabolism", J. Biol. Chem., vol. 278(19), pp. 17190-17197, (2003).
Yu, T. et al, "Increased production of reactive oxygen species in hyperglycemic conditions requires dynamic change of mitochondria! morphology", PNAS, vol. vol. 103(8), pp. 2653-2658, (Feb. 2006).

(Continued)

*Primary Examiner* — Changhwa J Cheu
(74) *Attorney, Agent, or Firm* — McHale & Slavin, P.A.

(57) ABSTRACT

Compositions of modulators of acyl-CoA lysocardiolipin acyltransferase 1 (ALCAT1) expression, function or activity are provided. In particular, inhibitors of ALCAT1 are useful in treating metabolic diseases, cardiac diseases and, in general diseases associated with mitochondrial dysfunction. Assays for identification of novel ALCAT1 modulators are provided.

6 Claims, 31 Drawing Sheets
(16 of 31 Drawing Sheet(s) Filed in Color)
Specification includes a Sequence Listing.

(56) References Cited

OTHER PUBLICATIONS

Han, X. et al, "Alterations in mychondrial cardiolipin content and composition occur at the very earliest stages of diabetes: a shotgun lipidomics study", Biochemistry, vol. 46(21), pp. 6417-6428, (Dec. 2007).
Sparagna, G. et al, "Cardiolipin remodeling in the heart", J. Cardiovasc. Pharmacol., vol. 53(4), pp. 290-301, (Apr. 2009) Abstract.
Lee, H. et al, "Selective remodeling of cardiolipin fatty acids in the aged rat heart", Lipids in Health and Disease, vol. 5:2, pp. 1-4, (Jan. 2006).
Paradies, G. et al, "Oxidative stress, mitochondrial bioenergetics, and cardiolipin in aging", Free Radic. Biol. Med., vol. 48:10, pp. 1286-1295, (May 2010) Abstract.
Choi, S. et al, "A common lipid links Mfn-mediated mitochondrial fusion and SNARE-regulated exocytosis", Nat. Cell Biol., vol. 8(11), pp. 1255-1262, (Epub Oct. 2008).
Huang, H. et al, "piRNAs meet mitochondria", Dev. Cell, vol. 20(3), pp. 376-387, Mar. 2011).
Claypool, S. et al, "The complexity of cardiolipin in health and disease", Trends Biochem. Sci., vol. 37(1), pp. 32-41, (Jan. 2012).
Drummond, G. et al, "Combating oxidative stress in vascular disease: NADPH oxidases as therapeutic targets", Nat. Rev. Drug Discov., vol. 10(6), pp. 453-471, (Jun. 2011).
Lesnefsky, E. et al, "Ischemia, rather than reperfusion, inhibits respiration through cytochrome oxidase in the isolated, perfused rabbit heart: role of cardiolipin", Am. J. Physiol. Heart Circ. Physiol., vol. 287, pp. H258-H267, (2004).
Cao, J. et al, "ALCAT1 is a polyglycerophospholipid acyltransferase potently regulated by adenine nucleotide and thyroid status", American. Journal of Physiology Endocrinology and Metabolism, vol. 296, pp. E647-E653, (2009).
Li, J. et al, "Cardiolipin remodeling by ALCAT1 links oxidative stress and mitochondrial dysfunction to obesity", Cell Metabolism, vol. 12, pp. 154-165, (Aug. 4, 2010).
Xiong, J. et al, "An acyltransferase controls the generation of hematopoietic and endothelial lineages in zebrafish", Circulation Research, vol. 102, pp. 1057-1064, (2008).
Reddy, J. et al, "Lipid metabolism and liver inflammation. II. Fatty liver disease and fatty acid oxidation", Am. J. Gastrointest Liver Physiol., vol. 290, pp. g852-g858, (2006).
Claypool, S. et al, "The complexity of Cardiolipin in health and disease", Trends Biochem., vol. 37(1), pp. 32-41, (Jan. 2012).
Greenwood, F. et al, "The preparation of [131] I-labelled human growth hormone of high specific radioactivity", Biochem. J., vol. 89, pp. 114-123, 1963.
David, G. et al, "Protein iodination with solid state lactorperoxidase", Biochemistry, vol. 13(5), pp. 1014-1021, (Feb. 1974) Abstract.
Leary, J. et al, "Rapid and sensitive colorimetric method for visualizing biotin-labeled DNA probes hybridized to DNA or RNA immobilized on nitrocellulose bio-blots", Proc. Natl. Acad. Sci. USA, vol. 80, pp. 4045-4049, (Jul. 1983).
Benz, M. et al, "A colorimetric method for DNA hybridization", Nucl. Acids Res., vol. 12, pp. 3435-3444, (1984).
Richardson, R. et al, "Biotin and fluorescent labeling of RNA using T4 RNA ligase", Nucl. Acids Res., vol. 11(18), pp. 6167-6184, (1983).
Smith, L. et al, "The synthesis of oligonucleotides containing an aliphatic amino group at the 5' terminus: synthesis of fluorescent DNA primers for use in DNA sequence analysis", Nucl. Acids Res., vol. 13, pp. 2399-2412, (1985).
Meinkoth, J. et al, "Hybridization of nucleic acids immobilized on solid supports", Anal. Biochem., vol. 138, pp. 267-284, (1984) Abstract.
Rotman, B., "Measurement of activity of single molecules of beta-D-galactosidase.", Proc. Natl. Acad. Sci. USA, vol. 47, pp. 1981-1991, (1961).
Czarnik, A., "Encoding strategies in combinatorial chemistry", Proc. Natl. Acad. Sci. USA, vol. 94, pp. 12738-12739, (Nov. 1997).

Thompson, L. et al, "Synthesis and applications of small molecule libraries", Chem. Rev. vol. 96, pp. 550-600, (1996).
Kenan. D. et al, "Exploring molecular diversity with combinatorial shape libraries", Trends in Biochem. Sci., vol. 19(2), pp. 57-64, (Feb. 1994) Abstract.
Janda, K. "Tagged versus untagged libraries: methods for the generation and screening of combinatorial chemical libraries", Proc. Natl. Acad. Sci. USA, vol. 91, pp. 10779-10785. (Nov. 1994).
Lebl, M. et al, "One-bead-one-structure combinatorial libraries", Biopolymers, vol. 37(3), pp. 177-198, (1995) Abstract.
Eichler, J. et al, "Peptide, peptidomimetic, and organic synthethic combinatorial libraries", Med. Res. Rev., vol. 15, pp. 481-496, (Nov. 1995) Abstract.
Chabala, J., "Solid-phase combinatorial chemistry and novel tagging methods for identifying leads", Curr. Opin. Biotechnol., vol. 6(6), pp. 632-639, (1995) Abstract.
Dolle, R., "Discovery of enzyme inhibitors through combinatorial chemistry", Mol. Divers., vol. 2(4), pp. 223-236, (1997).
Fauchere, J. et al, "Peptide and nonpeptide lead discovery using robotically synthesized soluable libraries", Can. J. Physiol. Pharmacol., vol. 75, pp. 683-689, (1997).
Eichler, J. et al, "Generation and utilization of synthetic combinatorial libraries", Mol. Med. Today, vol. 1(4), pp. 174-180, (Jul. 1995) Abstract.
Kay, B. et al, "Identification of enzyme inhibitors from phage-displayed combinatorial peptide libraries", Chomb. Chem. High Throughput Screen, vol. 4(7), pp. 535-543, (Nov. 2001).
Hobbs-Dewitt, S. et al, ""Diversomers": an approach to nonpeptide, nonoligomeric chemical diversity", PNAS, vol. 90(15), pp. 6909-6913, Aug. 1993).
Hagihara, M., "Vinylogous polypeptides: an alternative peptide backbone", J. Am. Chem. Soc., vol. 114(16), pp. 6568-6570, (Jul. 1992).
Hirshmann, R. et al, "Nonpeptidal peptidomimetics with .beta.-D-glucose scaffolding. A partial somatostatin agonist bearing a close structural relationship to a potent, selective substance P antogonist", J. Am. Chem. Soc., vol. 114(23), pp. 9217-9218, (1992) Abstract.
Chen, C. et al, ""Analogous" organic synthesis of small-compound libraries: validation of combinatorial chemistry in small-molecule synthesis", J. Amer. Chem. Soc., vol. 116(6), pp. 2661-2662, (1994).
Cho, C. et al, "An unnatural polymer", Science, vol. 261(5126), pp. 1303-1305, (Sep. 1993) Abstract.
Campbell, D. et al, "Phosphonate ester synthesis using a modified Mitsunobu condensation", J. Amer. Chem. Soc., vol. 59, pp. 658-660, (1994) Abstract.
Vaughn, T. et al, "Human antibodies with sub-nanomolar affinities isolated from a large non-immunized phage display library", Nature Biotechnol., vol. 14(3), pp. 309-314, (Mar. 1996).
Liang, R. et al, "Parallel synthesis and screening of a solid phase carbohydrate library", Science, vol. 274(5292), pp. 1520-1522, (Nov. 1996) abstract.
Baum, R., "Solid-phase synthesis of benzodiazepines", Chem. Eng. News, vol. 71(3), pp. 33-34, (1993) Abstract.
Moore, M. et al, "Site-specific modification of pre-mRNA: the 2'-hydroxyl groups at the splice sites", Science, vol. 256, pp. 992-997, (May 1992).
Shabarova, Z., "Chemical ligation of DNA: the first non-enzymatic assembly of a biologically active gene", Nucleic Acids Res., vol. 19(15), pp. 4247-4251, (Jul. 1991).
Bellon, L. et al, "Amino-linked ribozymes: post-synthetic conjugation of half-ribozymes", J. Prog. in Second Gen. Oligomer Therapeutics, vol. 16(7-9), pp. 951-954, ( Aug. 2006).
Bellon, L. et al, "Post-synthetically ligated ribozymes: an alternative approach to iterative solid-phase synthesis", Bioconjugate Chem., vol. 6(2), pp. 204-212, (Mar. 1997) Abstract.
Gold, L. et al, "Diversity of oligonucleotide functions", Annu. Rev. Biochem., vol. 64, pp. 763-797, (1995) Abstract.
Brody, E et al, "Aptamers as therapeutic and diagnostic agents", J. Biotechnol., vol. 74(1), pp. pp. 5-13, (2000).
Sun, S. Technology evaluation: SELEX, Gilead Sciences, Inc., Curr Opin Mol. Ther., vol. 2(1), pp. 100-105, (Feb. 2000) Abstract.

(56) References Cited

OTHER PUBLICATIONS

Kusser, W., "Chemically modified nucleic acid aptamers for in vitro selections: evolving evolution", Rev. in Molecular Biotechnology, vol. 74(1), pp. 27-38, (Mar. 2000) Abstract.

Hermann, T. et al, "Adaptive recognition by nucleic acid aptamers", Science, vol. 287(5454), pp. 820-825, (Feb. 2000).

Jayasena, S., "Aptamers: an emerging class of molecules that rival antibodies in diagnostics", Clinical Chemistry, vol. 45(9), pp. 1628-1650. (1999).

Schena, M. et al, "Parallel human genome analysis: microarray-based expression monitoring of 1000 genes", Proc. Natl. Acad. Sci. USA, vol. 93, pp. 10614-10619, (Oct. 1996).

Heller, R. et al, "Discovery and analysis of inflammatory disease-related genes using cDNA microarrays", Proc. Natl. Acad. Sci. USA, vol. 94, pp. 2150-2155, (Mar. 1997).

Merrifield, R., "Solid phase synthesis. I. The synthesis of a tetrapeptide", J. Amer. Chem. Soc., vol. 85, pp. 2149-2154, (Jan. 1963) Abstract.

Geysen, H. et al, "Strategies for epitope analysis using peptide synthesis", J. of Immunol. Meth., vol. 102(2), pp. 259-274, (Sep. 1987) Abstract.

Frank. R. et al, "Simultaneous multiple peptide synthesis under continuous flow conditions on cellulose paper discs as segmental solid supports", Tetrahedron, vol. 44(19), pp. 6031-6040, (1988) Abstract.

Fodor, S. et al, "Light-directed, spatially addressable parallel chemical synthesis", Science, vol. 251(4995), pp. 767-773, (Feb. 1991) Abstract.

Sheldon, E. et al, "Matrix DNA hybridization", Clin. Chem., vol. 39(4), pp. 718-719, (1993).

\* cited by examiner

SEQUENCE LISTING

```
<160> NUMBER OF SEQ ID NOS: 18

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence:  Synthetic
      primer

<400> SEQUENCE: 1
tgacccatag ccataatatg attt                                            24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ttctacgtta aaccctgata ctaa                                            24

<210> SEQ ID NO 3
<211> LENGTH: 20
<212> TYPE: DNA
```

-continued

<213> ORGANISM: Artificial Sequence
<220> FEATURE:
<223> OTHER INFORMATION: Description of Artificial Sequence: Synthetic
      primer

<400> SEQUENCE: 3
acacgccata atggcactcc                                                    20

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cagtcttggc agtgcagat                                                     19

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agggcgacct caacgagat                                                     19

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cagcagactc tggaggctct t                                                  21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gctgctttgg gcacaagata g                                                  21

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggagctcttc ctacaacaac tt                                                 22

<210> SEQ ID NO 9
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 9
gtgtacagtg cggtgtccaa                                                   20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
acctcatctt ctaccggatc                                                   20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gttcgcgctc tctctcctca                                                   20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcaaccacag cacgattgtc                                                   20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gagcggagag tactggatcg                                                   20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gttcgggctg atgtaccagt                                                   20

<210> SEQ ID NO 15
<211> LENGTH: 20
<212> TYPE: DNA
<213> ORGANISM: Artificial Sequence
<220> FEATURE:
```

-continued

```
<223> OTHER INFORMATION: Description of Artificial Sequence: Synthetic
      primer

<400> SEQUENCE: 15
accaaaaggt gatgctggac                                             20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gacctcgtgc tccagttagc                                             20

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aatggtgaag gtcggtgtg                                              19

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gtggagtcat actggaacat gtag                                        24
```

MODULATORS OF ACYL-COA LYSOCARDIOLIPIN ACYLTRANSFERASE 1 (ALCAT1) AND USES THEREOF

CROSS-REFERENCE TO RELATED APPLICATIONS

In accordance with 37 C.F.R. § 1.76, a claim of priority is included in an Application Data Sheet filed concurrently herewith. Accordingly, the present invention claims priority as a divisional of U.S. patent application Ser. No. 14/378, 525, entitled "MODULATORS OF ACYL-COA LYSO-CARDIOLIPIN ACYLTRANSFERASE 1 (ALCAT1) AND USES THEREOF", filed Aug. 13, 2014, which is a national stage filing in accordance with 35 U.S.C. § 371 of PCT/US2013/026311, entitled "MODULATORS OF ACYL-COA LYSOCARDIOLIPIN ACYLTRANSFERASE 1 (AL-CAT1) AND USES THEREOF", filed Feb. 15, 2013, which claims the benefit of the priority of U.S. Provisional Patent Application No. 61/599,496, entitled "MODULATORS OF ACYL-COA LYSOCARDIOLIPIN ACYLTRANSFERASE 1 (ALCAT1) AND USES THEREOF", filed Feb. 16, 2012, which are incorporated herein by reference in their entirety.

STATEMENT REGARDING FEDERALLY SPONSORED RESEARCH

This invention was made with U.S. government support under grant number DK076685 awarded by the National Institutes of Health. The U.S. government may have certain rights in the invention.

FIELD OF THE INVENTION

Embodiments of the invention are directed to compositions for the treatment of diseases associated with mitochondrial dysfunction, metabolic diseases, neurological diseases and cardiac diseases. Methods of identifying novel agents and uses in treatment are provided.

BACKGROUND

Cardiolipin (CL), a mitochondrial phospholipid initially identified in the heart, plays a pivotal role in maintaining normal cardiac function. In mammals, the biological function of CL is determined by the composition of its fatty acyl chains which is dominated by linoleic acid (18:2) in metabolic tissues, such as heart, liver, and skeletal muscle. This unique acyl composition is believed to support mitochondrial membrane proton gradient and activity of various mitochondrial enzymes and proteins. Consequently, a loss of tetralinoleoyl CL (TLCL), the predominant species in the healthy mammalian heart, occurs during the onset of heart failure both in rodents and humans with dilated cardiomyopathy. CL is biosynthesized in a series of steps from phosphatidic acid. Newly synthesized CL must go through a remodeling process that involves phospholipases and acyltransferase/transacylases to incorporate linoleic acid into its fatty acyl chains. Accordingly, defective CL remodeling causes dilated cardiomyopathy in Barth syndrome, an X-linked genetic disorder characterized by linoleic acid deficiency in CL, mitochondrial dysfunction, growth retardation, and neutropenia. Furthermore, aberrant CL acyl composition from pathological CL remodeling has been implicated in the etiology of mitochondrial dysfunction associated with a host of pathophysiological conditions in aging and age-related diseases including diabetes, obesity, cardiovascular diseases and neurodegeneration, all of which are characterized by oxidative stress, CL deficiency, enrichment of docosahexaenoic acid (DHA) in CL, and mitochondrial dysfunction.

SUMMARY

This Summary is provided to present a summary of the invention to briefly indicate the nature and substance of the invention. It is submitted with the understanding that it will not be used to interpret or limit the scope or meaning of the claims.

Embodiments of the invention are directed, inter alia, to compositions which modulate the expression, function and/or activity of lysocardiolipins, in particular, acyl-CoA lysocardiolipin acyltransferase 1 (ALCAT1). In particular, inhibitors of ALCAT1 are useful in treating metabolic diseases, cardiac diseases and, in general diseases associated with mitochondrial dysfunction. Assays for identification of novel ALCAT1 modulators are provided.

In one embodiment, a method of identifying a modulator of acyl-CoA lysocardiolipin acyltransferase 1 (ALCAT1) expression, function or activity, comprises contacting a biological sample with a test agent; measuring expression, function or activity of a mitofusin molecule in the biological sample. In one embodiment, a test agent is identified as an inhibitor of ALCAT1 expression, function or activity if the agent increases the expression, function or activity of the mitofusin molecule as compared to a baseline control. Preferably, ALCAT1 molecule expression, function or activity is substantially decreased as compared to a normal baseline control.

In another embodiment, an assay to measure mitofusin molecule (e.g. MFN2) expression, function or activity comprises: immunoassays, bioassays, biochip assays, blots, hybridization assays, cell-based assays, high-throughput screening assays, chromatography, chemical assays, phage display assays or combinations thereof.

In another embodiment, a method of identifying a modulator of acyl-CoA lysocardiolipin acyltransferase 1 (AL-CAT1) expression, function or activity, comprises: contacting a biological sample with a test agent; measuring (a) expression of hypertrophic markers indicative of cardiomyopathy comprising: BNP, β-MHC, ANF or ACTA1; (b) expression, function or activity of PTEN-induced putative kinase 1 (PINK1); and, identifying the ALCAT1 modulator.

In one embodiment, an inhibitor of ALCAT1 expression, function or activity is identified if the test agent decreases the expression of hypertrophic markers indicative of cardiomyopathy as compared to a baseline control. In one aspect, an inhibitor of ALCAT1 expression, function or activity is identified if the test agent increases the expression, function or activity of PTEN-induced putative kinase 1 (PINK1) as compared to a baseline control.

In another preferred embodiment, a method of preventing or treating mitochondrial dysfunction in vitro or in vivo, comprising: administering to a cell or patient a therapeutically effective amount of an agent that modulates expression, function activity or combinations thereof, of a lysocardiolipin acyltransferase. In one embodiment, the lysocardiolipin acyltransferase is acyl-CoA lysocardiolipin acyltransferase 1 (ALCAT1).

In another preferred embodiment, an ALCAT1 regulates: mitochondrial polynucleotides mitochondrial polypeptides, mitochondrial proteins, mtDNA copy number; mitochondrial mass; mitochondrial morphology; mitochondrial fusion and mtDNA mutation rates.

In another preferred embodiment, a mitochondrial protein comprises: mitofusins, mitofusin-1 (MFN1), mitofusin-2, (MFN2), prohibitin, peptides, fragments, variants, mutants or combinations thereof.

In another embodiment, a mitofusin is optionally administered with one or more ALCAT1 inhibitors identified by any of the methods herein, including any other as yet undefined ALCAT1 inhibitors.

In one embodiment, the inhibitor of ALCAT1 increases expression, function or activity of MFN2 as compared to a baseline control.

In another embodiment, an inhibitor of ALCAT1 decreases oxidative stress as measured by reactive oxygen species (ROS) and compared to a normal baseline control.

In another embodiment, an inhibitor of ALCAT1 modulates cardiolipin (CL) structure, function, activity, expression or combinations thereof.

In embodiments, an inhibitor of ALCAT1 prevents or treats diseases or disorders associated with mitochondrial dysfunction. Examples include, without limitation: diabetes, obesity, cardiac diseases or disorders, neurodegenerative diseases or disorders, metabolic diseases or disorders.

In another preferred embodiment, a method of preventing or treating mitochondrial dysfunction in vitro or in vivo, comprises: administering to a cell or patient a therapeutically effective amount of a mitofusin molecule; and, preventing or treating mitochondrial dysfunction in vitro or in vivo.

In another preferred embodiment, a method of treating a patient suffering from cardiomyopathy or at risk of cardiomyopathy, comprising: administering to a patient in need thereof, a therapeutically effective amount of an inhibitor of acyl-CoA lysocardiolipin acyltransferase 1 (ALCAT1); and, treating a patient suffering from cardiomyopathy.

In another preferred embodiment, an inhibitor of acyl-CoA lysocardiolipin acyltransferase 1 (ALCAT1) is identified by any of the methods herein.

In another embodiment, a pharmaceutical composition comprising an inhibitor of acyl-CoA lysocardiolipin acyltransferase 1 (ALCAT1) is identified by any of the methods herein.

In another preferred embodiment, a method of identifying a modulator of acyl-CoA lysocardiolipin acyltransferase 1 (ALCAT1) expression, function or activity, comprises contacting a biological sample with a test agent; measuring expression, function or activity of ALCAT1 molecules in the biological sample; and, identifying a modulator of acyl-CoA lysocardiolipin acyltransferase 1 (ALCAT1). Preferably, a test agent is identified as an inhibitor of ALCAT1 expression, function or activity if the agent increases the expression, function or activity of the ALCAT1 molecules as compared to a baseline control.

In embodiments, ALCAT1 molecules comprise: nucleic acids, oligonucleotides, polynucleotides, genes, amino acids, peptides, polypeptides, proteins, variants, fragments, mutants or combinations thereof.

In embodiments, a biological sample comprises: fluids, peptides, polypeptides, oligonucleotides, polynucleotides, cells, tissues or combinations thereof.

In other embodiments, assays to measure any molecules' expression, function or activity comprises: immunoassays, bioassays, biochip assays, blots, hybridization assays, cell-based assays, high-throughput screening assays, chromatography, chemical assays, phage display assays or combinations thereof.

Other aspects are described infra.

BRIEF DESCRIPTION OF THE DRAWINGS

The patent or application contains at least one drawing executed in color. Copies of this patent or patent application publication with color drawings will be provided by the Office upon request and payment of the necessary fee.

FIGS. 1A, 1B: Confocal microscopy analysis of mitochondrial network in C2C12 cells stably expressing ALCAT1 (FIG. 1B) or vector control (FIG. 1A) by Mitotracker Red. Insets represent magnification of the boxed areas. The scale bars represent 5 µm. FIG. 1C: Quantitative analysis of mitochondrial morphology in C2C12 expressing ALCAT1 or vector control in three categories: "tubular" with >90% elongated interconnected networks, "mix" with mixed tubular and short mitochondria, and "fragmented" with >90% short punctated mitochondria from three independent experiments, N=300; FIGS. 1D-1G: EM analysis of mitochondrial morphology in C2C12 cells stably expressing vector control (FIG. 1D, highlighted in FIG. 1F) or ALCAT1 (FIG. 1E, highlighted in FIG. 1G). The scale bars represent 1 µm. FIGS. 1H-1I: RT-PCR analysis of mtDNA copy number (FIG. 1H) and point mutation rate (FIG. 1I) in C2C12 cells stably expressing ALCAT1 or vector control. $*p<0.05$, $**p<0.01$, N=3.

FIGS. 2A-2D: EM analysis of mitochondrial morphology in MEF cells from wild type control mice (WT) (FIG. 2A, highlighted in FIG. 2C) and from ALCAT1 knockout mice (KO) (FIG. 2B, highlighted in FIG. 2D). FIGS. 2E-2F: EM analysis of the tibialis anterior longitudinal section from WT mice (FIG. 2E) and ALCAT1 knockout mice (FIG. 2F). Arrows indicate A band, I bands, Z line, and mitochondria (M), respectively. FIGS. 2G-2H: RT-PCR analysis of mtDNA copy number (FIG. 2G) and point mutation rate (FIG. 2H) in MEF cells isolated from KO mice and the WT controls. $**p<0.01$, N=3.

FIGS. 3A-3B: Real-time PCR analysis of mRNA expression levels of MFN1, MFN2 and OPA1 in C2C12 cells stably expressing ALCAT1 or vector control (FIG. 3A) and in MEFs isolated from WT and KO mice (FIG. 3B). GAPDH expression was used as an internal control. FIG. 3C: Western blot analysis of MFN1, MFN2 and OPA1 protein levels in C2C12 expressing ALCAT1 or vector control. Relative density of each band was shown under each lane using actin as an internal control for protein loading. FIG. 3D: Western blot analysis of protein levels of MFN1, MFN2, OPA1, calnexin, and prohibitin in MEFs isolated from KO and WT control mice using -actin as an internal control for protein loading. N=3 fetuses in each group. FIG. 3E: Quantitative analysis of data shown in panel E. $*P<0.05$, $**P<0.01$ when compared with control.

FIGS. 4A-4D: Confocal images of mitochondria in C2C12 cells stably expressing vector control, which demonstrated complete fusion, as evidenced by the yellow color in FIG. 4C and highlighted in FIG. 4D. FIGS. 4E-4H: Images of mitochondria in C2C12 cell stably expressing ALCAT1, which exhibited fusion defect, as shown by the separated green and red colors in FIG. 4G and highlighted in FIG. 4E. FIGS. 4I-4L, transient expression of MFN2 (MFN2-YFP) rescued the fusion defect in C2C12 cells stably expressing ALCAT1 (K, highlighted in L). The scale bar represents 5 µm.

FIGS. 5A-5D: Confocal image analysis of mitochondrial network in C2C12 cells stably expressing vector control (FIGS. 5A-5B) or ALCAT1 (FIGS. 5C-5D). The stable C2C12 cell lines were transiently transfected with mitochondrial-targeted EGFP expression vector (FIGS. 5A & 5C) and stained with Mitotracker Red (FIGS. 5B & 5D) prior to imaging. FIGS. 5E-5J: Confocal image analysis of mitochondrial network in C2C12 cells stably expressing ALCAT1 and transiently transfected with expression vectors for Myc-tagged MFN1 (FIGS. 5E-5F), MFN2-YFP (yellow fluorescence protein) (FIGS. 5G-5H), or Myc-tagged OPA1 (FIGS. 5I-5J), respectively. For the Myc-tagged proteins, cells were immunostained with anti-Myc antibodies and followed by goat anti-mouse FITC-conjugated antibodies (green), and then Mitotracker Red. The scale bar represents 5 µm.

FIG. 6A, FCCP, a mitochondrial uncoupler; FIG. 6B, rotenone, a complex I inhibitor; FIG. 6C, antimycin, a complex III inhibitor; and FIG. 6D, oligomycin, an ATPase inhibitor. The exogenous and endogenous MFN2 protein levels were analyzed by western blot analysis using MFN2 antibodies, as shown in FIG. 6A. OCR was analyzed by Seahorse X-24 analyzer, and calculated from at least three independent measurements for each chemical treatment. *$p<0.05$ compared to control; #$p<0.05$ and ##$p<0.01$ when compared to nontransfected ALCAT1-expressing cells.

FIGS. 7A-7D: EM analysis of mitochondrial morphology in MEF from WT mice (FIG. 7A, highlighted in FIG. 7C) or KO mice (FIG. 7B, highlighted in FIG. 7D) treated with 1 mM of $H_2O_2$. FIG. 7E: C2C12 cells stably expressing ALCAT1 or vector control were treated with indicated doses of $H_2O_2$, followed by analysis for the level of malonaldehyde (MDA), a lipid peroxidation product from oxidative stress. **$p<0.01$ compared to vector control. FIG. 7F: C2C12 stably expressing ALCAT1 or vector control were treated with increasing doses of $H_2O_2$ as indicated in FIG. 7E, followed by Western blot analysis for MFN1 and MFN2 using β-actin as an internal control for protein loading. FIG. 7G: Western blot analysis of MFN1 and MFN2 expression in C2C12 cells stably expressing vector, ALCAT1, or ALCAT1 but were pretreated various doses (0, 1M, and 5M) of diphenyliodonium (DPI), an NADPH oxidase inhibitor, prior to treatment with 1.5 mM of $H_2O_2$. FIG. 7H: A schematic model depicting a causative role of ALCAT1 in linking oxidative stress to MFN2 deficiency and mitochondrial fragmentation.

FIG. 11B: the real-time production of $H_2O_2$ from isolated mitochondria; FIG. 11C: mtDNA copy number after treatment with indicated doses of $H_2O_2$; mean±SEM (n=3). FIG. 11D: TABRS level was analyzed in isolated cardiac ventricle from wide type (WT) and ALCAT1 knock out (KO) mice treated with vehicle or T4 for 28 consecutive days; mean±SEM (n=5). FIGS. 11E-11F: differentiation of H9c2 cells stably expressing vector control (FIG. 11E) or ALCAT1 (FIG. 11F) to cardiomyocytes.

FIG. 12B: heart to body weight ratio; FIGS. 12C-12E: echocardiographic parameters, including interventricular septal defect (IVSD), left ventricular end diastolic diameter (LVEDD), and left ventricular posterior wall dimensions (LVPWD). n=6-8, *$P<0.05$, **$P<0.01$.

FIGS. 13A-13D: WT and KO mice were treated with vehicle or T4 for 28 days, and were analyzed for cardiomyocyte morphology by H&E staining. FIGS. 13E-13F: quantitative analysis of mean cardiomyocyte size and diameter, n=250. **$P<0.01$. FIG. 13G: distribution analysis of cardiomyocyte size from WT and KO mice after T4 treatment for 28 days, n=250.

FIGS. 14A-14D, representative sections of Masson's trichrome-stained left ventricle from WT and KO mice treated with vehicle (FIGS. 14A, 14C) and T4 (FIGS. 14B, 14D), respectively. Fibrosis areas which exhibit blue staining are highlighted by arrows. FIGS. 14E-14F: RT-PCR analysis of mRNA levels of fibrosis biomarkers, including collagen I and collagen III from same samples used in FIGS. 14A-14D. n=5, *$P<0.05$; **$P<0.01$.

FIGS. 15A-15D: WT and KO mice were treated with vehicle or T4 treatment for 28 days, and then analyzed for mRNA expression level of biomarkers of left ventricular hypertrophy and heart failure, including brain natriuretic peptide (BNP), β-myosin heavy chain (β-MHC), atrial natriuretic factor (ANF), and skeletal muscle α-actin (ACTA1). n=6-8, *P<0.05; **P<0.01.

FIGS. 16A-16D: representative electron micrographs of cardiomyocytes from WT (FIGS. 16A & 16B) and KO (FIGS. 16C & 16D) after T-4 treatment for 28 days. Arrows highlight mitochondria which exhibit damaged structure and abnormal morphology. Boxed areas in FIGS. 16A and 16B are enlarged in FIGS. 16C and 16D, which highlights mitochondria that were undergoing mitophagy. Scale bars represent 1 μM. FIG. 16E: Western blot analysis of autophagic biomarkers LC3, p62, and PINK1 in isolated ventricular tissues from individual WT and KO mice using GAPDH as an internal control. FIGS. 16F-16G: Quantitative analysis of expression levels of LC3 (FIG. 16F) and PINK1 (FIG. 16G) proteins shown in FIG. 16E. *P<0.05; **P<0.01.

FIGS. 17A-17B: H9c2 cardiac cells stably expressing ALCAT1 or vector control were stimulated with indicated doses of insulin (FIG. 17A) or with 100 nM of T3 for the indicated time (FIG. 17B), followed by analysis of phosphorylation of Akt, Erk, S6K1, and 4E-BP by western blot analysis using β-actin as an internal control. FIG. 17C: WT and KO mice were treated with vehicle or T4 for 28 days, followed by Western blot analysis of phosphorylation of Akt, GSK3α/β, and 4E-BP in cardiomyocytes by Western blot analysis using GAPDH as an internal control.

FIG. 18A, H9c2 cells stably expressing Flag-tagged ALCAT1 or vector control were analyzed growth rate for 7 consecutive passages (p1-p7) by cell counting. B, H9c2 cells stably expressing ALCAT1 or vector control were cultured in normal medium or in differentiation medium (DM) to induce differentiation to cardiomyocytes, followed by western blot analysis of myogenin and ALCAT1 expression using anti-myogenin and Flag antibodies. GAPDH was used as an internal control for protein loading (FIG. 18B).

FIGS. 19A-19B: representative electron micrographs of cardiomyocytes from vehicle-treated WT (FIG. 19A) and KO (FIG. 19B) mice. FIGS. 19C-19F, hyperthyroidism caused a marked increase in the number of damaged mitochondria in WT mice (FIG. 19C) when compared with KO (FIG. 19E). Boxed areas in FIGS. 19C and 19E are enlarged in FIGS. 19D and 19F, which highlight mitochondria that were undergoing mitophagy. Scale bar sizes are 1 μM.

As shown in FIGS. 22A and 22B, kidneys from nondiabetic WT and KO mice exhibited normal morphology. In contrast, the onset of diabetes in WT control mice caused renal failure (FIG. 22C), as evidenced by heavy staining with trichrome (blue color). In contrast, these pathological changes were prevented in the kidney of diabetic ALCAT1 KO mice (FIG. 22D).

As shown in FIG. 28A, the onset of diabetes caused atrophy of testis in WT control mice. Additionally, hyperglycemia caused a severe loss of spermatogonia (FIG. 28C, enlarged in FIG. 28D) and induction of giant cells (indicated by arrowhead) in WT control mice. In contrast, these defects were completely ablated in ALCAT1 KO mice (FIGS. 28B and 28E, enlarged in FIG. 28F).

DETAILED DESCRIPTION

Figures 1A, 1B, 1C, 1D, 1E, 1F, 1G, 1H, 1I:
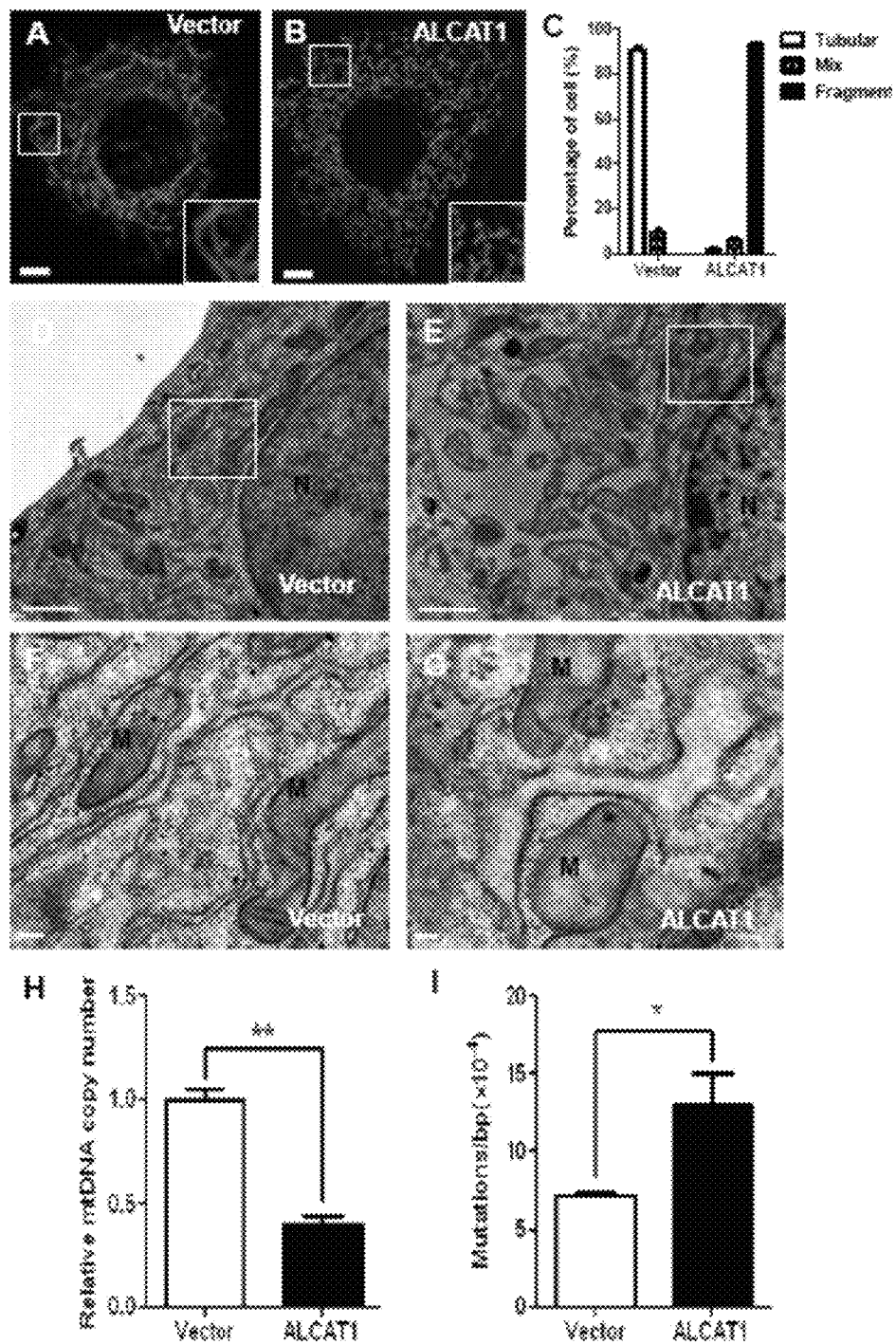
FIGS. 1A-1I show that ALCAT1 causes mitochondrial fragmentation and mtDNA instability in C2C12 cells.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Embodiments of the invention may be practiced without the theoretical aspects presented. Moreover, the theoretical aspects are presented with the understanding that Applicants do not seek to be bound by the theory presented.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes disclosed herein, which in some embodiments relate to mammalian nucleic acid and amino acid sequences are intended to encompass homologous and/or orthologous genes and gene products from other animals including, but not limited to other mammals, fish, amphibians, reptiles, and birds. In preferred embodiments, the genes or nucleic acid sequences are human.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

"Optional" or "optionally" means that the subsequently described circumstance may or may not occur, such that the description includes instances where the circumstance occurs and instances where it does not.

The terms "determining", "measuring", "evaluating", "detecting", "assessing" and "assaying" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

As used herein, the term "agent" is meant to encompass any molecule, chemical entity, composition, drug, therapeutic agent, chemotherapeutic agent, or biological agent capable of preventing, ameliorating, or treating a disease or other medical condition. The term includes small molecule compounds, antisense reagents, siRNA reagents, antibodies, enzymes, peptides organic or inorganic molecules, natural or synthetic compounds and the like. An agent can be assayed in accordance with the methods of the invention at any stage during clinical trials, during pre-trial testing, or following FDA-approval.

The term "ALCAT1" is meant to include, without limitation, nucleic acids, polynucleotides, oligonucleotides, sense and antisense polynucleotide strands, complementary sequences, peptides, polypeptides, proteins, homologous and/or orthologous ALCAT1 molecules, isoforms, precursors, mutants, variants, derivatives, splice variants, alleles, different species, and active fragments thereof.

The term "fragment" or "variant" is meant a fragment that is at least 380 amino acid residues in length and is 100% identical to a contiguous portion of the peptide, polypeptide or protein, or a variant that is at least 90%, preferably 95% identical to a fragment up to and including the full length peptide, polypeptide or protein. A variant, for example, may include conservative amino acid substitutions, as defined in the art, or nonconservative substitutions, providing that at least e.g. 10%, 25%, 50%, 75% or 90% of the activity of the original peptide, polypeptide or protein is retained. Also included are ALCAT1 molecules, fragments or variants having post-translational modifications such as sumoylation, phosphorylation glycosylation, splice variants, and the like, all of which may affect the efficacy of ALCAT1 function.

Unless otherwise indicated, the terms "peptide", "polypeptide" or "protein" are used interchangeably herein, although typically they refer to peptide sequences of varying sizes.

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) or single base mutations in which the polynucleotide sequence varies by one base. The presence of SNPs may be indicative of, for example, a certain population with a propensity for a disease state, that is susceptibility versus resistance.

As used herein, "cardiac disease" refers to any type of heart disease including cardiomyopathy, hypertrophic cardiomyopathy, dilated cardiomyopathy, atherosclerosis, coronary artery disease, ischemic heart disease, myocarditis, viral infection, wounds, hypertensive heart disease, valvular disease, congenital heart disease, myocardial infarction, congestive heart failure, arrhythmias, diseases resulting in remodeling of the heart, etc. Diseases of the heart can be due to any reason, such as for example, damage to cardiac tissue such as a loss of contractility (e.g., as might be demonstrated by a decreased ejection fraction).

Cardiac damage or disorder characterized by insufficient cardiac function includes any impairment or absence of a normal cardiac function or presence of an abnormal cardiac function. Abnormal cardiac function can be the result of disease, injury, and/or aging. As used herein, abnormal cardiac function includes morphological and/or functional abnormality of a cardiomyocyte, a population of cardiomyocytes, or the heart itself. Non-limiting examples of morphological and functional abnormalities include physical deterioration and/or death of cardiomyocytes, abnormal growth patterns of cardiomyocytes, abnormalities in the physical connection between cardiomyocytes, under- or over-production of a substance or substances by cardiomyocytes, failure of cardiomyocytes to produce a substance or substances which they normally produce, and transmission of electrical impulses in abnormal patterns or at abnormal times. Abnormalities at a more gross level include dyskinesis, reduced ejection fraction, changes as observed by echocardiography (e.g., dilatation), changes in EKG, changes in exercise tolerance, reduced capillary perfusion, and changes as observed by angiography. Abnormal cardiac function is seen with many disorders including, for example, ischemic heart disease, e.g., angina pectoris, myocardial infarction, chronic ischemic heart disease, hypertensive heart disease, pulmonary heart disease (cor pulmonale), valvular heart disease, e.g., rheumatic fever, mitral valve prolapse, calcification of mitral annulus, carcinoid heart disease, infective endocarditis, congenital heart disease, myocardial disease, e.g., myocarditis, dilated cardiomyopathy, hypertensive cardiomyopathy, cardiac disorders which result in congestive heart failure, and tumors of the heart, e.g., primary sarcomas and secondary tumors. Heart damage also includes wounds, such as for example, knife wound; biological (e.g. viral; autoimmune diseases) or chemical (e.g. chemotherapy, drugs); surgery; transplantation and the like.

As used herein, "dyslipidemia" refers to a biological condition in which lipid metabolism is abnormal, including lipoprotein overproduction or underproduction. Dyslipidemia in which lipoproteins are over-produced typically results in an elevation of total cholesterol, low-density lipoprotein (LDL) cholesterol and triglycerides concentrations, with a concomitant decrease in high-density lipoprotein (HDL) cholesterol concentration in the blood.

As used herein, "fatty liver disease" or "hepatic steatosis" refers to a condition in which the liver has accumulated greater than normal levels of triglycerides in the hepatocytes of the liver. The triglycerides are contained in either or both micro- or macrovesicular vacuoles within the hepatocyte cells. The diagnosis is made when the lipid content of the liver exceeds 5010% by weight. FLD may or may not be associated with consumption of alcohol (see Reddy et al., *Am. J. Physiol. Gastrointest. Liver Physiol.*, 2006, 290: G852-G858).

As used herein, "alcoholic fatty liver disease" refers to a condition of fatty liver disease in which the subject consumes on average, greater than 20 grams per day of alcohol. AFLD develops in essentially all individuals who consume approximately 60 or more grams of alcohol per day. AFLD can occur after the ingestion of moderate to large amounts of alcohol for even a short period of time. The subject may or may not be overweight or obese. Inclusive of this is liver cirrhosis.

As used herein, "non-alcoholic fatty liver disease" refers to a condition of fatty liver disease in which the subject consumes on average, less than 20 grams per day of alcohol. The subject may or may not be overweight or obese.

As used herein, "nonalcoholic steatohepatitis" or NASH refers to that stage of the development of NA fatty liver disease in which macrovesicles of fat have developed accompanied by lobular inflammation in the liver. Steatohepatitis, in which macrovesicles of fat have developed accompanied by lobular inflammation in the liver, may also occur in alcoholic fatty liver disease.

As used herein, "steatonecrosis" refers to that stage of NA fatty liver disease in which macrovesicles of fat have developed accompanied by lobular inflammation and ballooning degeneration in the liver. Further development of NAFLD from the level of steatonecrosis includes the development of fibrosis in addition to the presence of macrovesicles of fat, inflammation and ballooning degeneration in the liver. Steatonecrosis, in which macrovesicles of fat have developed accompanied by lobular inflammation and ballooning degeneration in the liver, we well as the development of fibrosis in addition to the presence of macrovesicles of fat, inflammation and ballooning degeneration in the liver may also occur in alcoholic fatty liver disease.

As used herein the phrase "diagnostic" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

As used herein the phrase "diagnosing" refers to classifying a disease or a symptom, determining a severity of the disease, monitoring disease progression, forecasting an outcome of a disease and/or prospects of recovery. The term "detecting" may also optionally encompass any of the above. Diagnosis of a disease according to the present invention can be effected by determining a level of a polynucleotide or a polypeptide of the present invention in a biological sample obtained from the subject, wherein the level determined can be correlated with predisposition to, or presence or absence of the disease. It should be noted that a "biological sample obtained from the subject" may also optionally comprise a sample that has not been physically removed from the subject, as described in greater detail below.

"Treatment" is an intervention performed with the intention of preventing the development or altering the pathology or symptoms of a disorder. Accordingly, "treatment" refers to both therapeutic treatment and prophylactic or preventative measures. "Treatment" may also be specified as palliative care. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy. Accordingly, "treating" or "treatment" of a state, disorder or condition includes: (1) preventing or delaying the appearance of clinical symptoms of the state, disorder or condition developing in a human or other mammal that may be afflicted with or predisposed to the state, disorder or condition but does not yet experience or display clinical or subclinical symptoms of the state, disorder or condition; (2) inhibiting the state, disorder or condition, i.e., arresting, reducing or delaying the development of the disease or a relapse thereof (in case of maintenance treatment) or at least one clinical or subclinical symptom thereof; or (3) relieving the disease, i.e., causing regression of the state, disorder or condition or at least one of its clinical or subclinical symptoms. The benefit to an individual to be treated is either statistically significant or at least perceptible to the patient or to the physician.

As defined herein, a "therapeutically effective" amount of a compound (i.e., an effective dosage) means an amount sufficient to produce a therapeutically (e.g., clinically) desirable result. The compositions can be administered one from one or more times per day to one or more times per week; including once every other day. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compounds of the invention can include a single treatment or a series of treatments. A "prophylactically effective amount" may refer to the amount of an agent sufficient to prevent the recurrence or spread of metabolic diseases or disorders, or the occurrence of such in a patient, including but not limited to those predisposed to metabolic disease, for example those genetically predisposed or previously exposed to environmental factors, such as for example, alcohol. A prophylactically effective amount may also refer to the amount of the prophylactic agent that provides a prophylactic benefit in the prevention of disease. Further, a prophylactically effective amount with respect to an agent of the invention means that amount of agent alone, or in combination with other agents, that provides a prophylactic benefit in the prevention of disease.

The term "sample" is meant to be interpreted in its broadest sense. A "sample" refers to a biological sample, such as, for example; one or more cells, tissues, or fluids (including, without limitation, plasma, serum, whole blood, cerebrospinal fluid, lymph, tears, urine, saliva, milk, pus, and tissue exudates and secretions) isolated from an individual or from cell culture constituents, as well as samples obtained from, for example, a laboratory procedure. A biological sample may comprise chromosomes isolated from cells (e.g., a spread of metaphase chromosomes), organelles or membranes isolated from cells, whole cells or tissues, nucleic acid such as genomic DNA in solution or bound to a solid support such as for Southern analysis, RNA in solution or bound to a solid support such as for Northern analysis, cDNA in solution or bound to a solid support, oligonucleotides in solution or bound to a solid support, polypeptides or peptides in solution or bound to a solid support, a tissue, a tissue print and the like.

Numerous well known tissue or fluid collection methods can be utilized to collect the biological sample from the subject in order to determine the level of DNA, RNA and/or polypeptide of the variant of interest in the subject. Examples include, but are not limited to, fine needle biopsy, needle biopsy, core needle biopsy and surgical biopsy (e.g., brain biopsy), and lavage. Regardless of the procedure employed, once a biopsy/sample is obtained the level of the variant can be determined and a diagnosis can thus be made.

In accordance with the present invention, there may be employed conventional molecular biology, microbiology, recombinant DNA, immunology, cell biology and other related techniques within the skill of the art. See, e.g., Sambrook et al., (2001) Molecular Cloning: A Laboratory Manual. 3rd ed. Cold Spring Harbor Laboratory Press: Cold Spring Harbor, N.Y.; Sambrook et al., (1989) Molecular Cloning: A Laboratory Manual. 2nd ed. Cold Spring Harbor Laboratory Press: Cold Spring Harbor, N.Y.; Ausubel et al., eds. (2005) Current Protocols in Molecular Biology. John Wiley and Sons, Inc.: Hoboken, N.J.; Bonifacino et al., eds. (2005) Current Protocols in Cell Biology. John Wiley and Sons, Inc.: Hoboken, N.J.; Coligan et al., eds. (2005) Current Protocols in Immunology, John Wiley and Sons, Inc.: Hoboken, N.J.; Coico et al., eds. (2005) Current Protocols in Microbiology, John Wiley and Sons, Inc.: Hoboken, N.J.; Coligan et al., eds. (2005) Current Protocols in Protein Science, John Wiley and Sons, Inc. : Hoboken, N.J.; Enna et al., eds. (2005) Current Protocols in Pharmacology John Wiley and Sons, Inc.: Hoboken, N.J.; Hames et al., eds. (1999) Protein Expression: A Practical Approach. Oxford University Press: Oxford; Freshney (2000) Culture of Animal Cells: A Manual of Basic Technique. 4th ed. Wiley-Liss; among others. The Current Protocols listed above are updated several times every year.

Compositions and Modulators of ALCAT1

In a preferred embodiment, a pharmaceutical composition comprises an inhibitor of acyl-CoA lysocardiolipin acyltransferase 1 (ALCAT1). In another preferred embodiment, a pharmaceutical composition comprises a plurality of inhibitors of acyl-CoA lysocardiolipin acyltransferase 1 (ALCAT1) in one or more dose concentrations. In another preferred embodiment, a composition comprises at least one inhibitor of acyl-CoA lysocardiolipin acyltransferase 1 (ALCAT1) and at least one other therapeutic agent. For example, the second therapeutic agent may be one that treats a particular symptom. In another example, the agent targets another aspect of the disease, such as for example, abnormal cell proliferation. In this case the agent would be a chemotherapeutic agent used in treating a cancer patient.

Mitofusin-2 (MFN2) encodes a mitochondrial protein that is required for mitochondrial integrity, fusion, metabolism, and tethering with ER. Mutations in MFN2 in humans cause peripheral neuropathy and Charcot-Marie-Tooth disease. MFN2 deficiency is also implicated in mitochondrial dysfunction associated with obesity and type 2 diabetes. Muscle MFN2 expression is reduced in type 2 diabetic patients. MFN2 expression negatively correlates with obesity and positively correlates with insulin sensitivity. Amelioration of insulin resistance in type 2 diabetes by bariatric surgery increases MFN2 expression in muscle. Likewise, moderate physical exercise, which is known to improve insulin sensitivity, significantly increases MFN2 expression and mitochondrial biogenesis. Additionally, targeted deletion of MFN2 in mouse skeletal muscle causes mtDNA instability and high mutation rates leading to severe mtDNA depletion.

Cardiolipin (CL) is a key mitochondrial phospholipid required for oxidative phosphorylation. CL is highly sensitive to oxidative damage of its double bonds by ROS due to its rich content in linoleic acid and location near the site of ROS production in the inner mitochondria membrane, a process also known as CL peroxidation. CL is the only phospholipid in mitochondria that undergoes early oxidation during apoptosis, which triggers the release of cytochrome c to cytosol leading to apoptotic consumption. Consequently, abnormal CL acyl composition from pathological remodeling has been implicated in the etiology of mitochondrial dysfunction commonly associated with diabetes, obesity, cardiovascular diseases, neurological disorders, cancer, aging, and other age-related diseases (Claypool S M & Koehler C M (2012) The complexity of cardiolipin in health and disease. *Trends Biochem Sci.* Jan; 37(1):32-41).

ALCAT1 is a lysocardiolipin acyltransferase that was recently identified to catalyze pathological remodeling of CL in response to oxidative stress in diabetes, obesity, and cardiomyopathy, leading to ROS production, mitochondrial dysfunction, and insulin resistance. CL remodeling by acyl- CoA lysocardiolipin acyltransferase 1 (ALCAT1) also results in changes of CL acyl composition that is reminiscent of age-related diseases, including CL deficiency, depletion of linoleic acid, and enrichment of docosahexaenoic acid (DHA) content in CL. Targeted inactivation of ALCAT1 prevents the onset of diet-induced obesity and its related metabolic complications.

In preferred embodiments, a composition comprises a modulator of acyl-CoA lysocardiolipin acyltransferase 1 (ALCAT1). Preferably, the modulator inhibits the expression, function and/or activity of ALCAT1.

In another preferred embodiment, a composition comprising a modulator of acyl-CoA lysocardiolipin acyltransferase 1 (ALCAT1) is used to prevent or treat mitochondrial dysfunction in a patient. Mitochondrial dysfunction in a patient is associated with metabolic diseases or disorders thereof. Examples include, without limitation: diabetes, fatty liver, infertility, neurodegenerative diseases, neuroinflammatory diseases, obesity, cancer, autoimmune diseases, encephalopathy, renal diseases, liver diseases, cardiac diseases, muscular disease, erectile dysfunction, menopause, metabolic diseases or disorders, aging related diseases, and the like.

In another preferred embodiment, a method of preventing or treating mitochondrial dysfunction in vitro or in vivo, comprises administering to a cell or patient a therapeutically effective amount of an agent that modulates expression, function activity or combinations thereof, of a lysocardiolipin acyltransferase. Preferably the lysocardiolipin acyltransferase is acyl-CoA lysocardiolipin acyltransferase 1 (ALCAT1).

In another preferred embodiment, a modulator of ALCAT1 regulates: mitochondrial polynucleotides mitochondrial polypeptides, mitochondrial proteins, mtDNA copy number; mitochondrial mass; mitochondrial morphology; mitochondrial fusion and mtDNA mutation rates. Preferably, the mitochondrial protein comprises: mitofusins, mitofusin-1 (MFN1), mitofusin-2, (MFN2), prohibitin, peptides, fragments, variants, mutants or combinations thereof.

In one embodiment, a mitofusin molecule is optionally administered to a patient with one or more ALCAT1 inhibitors wherein an inhibitor of ALCAT1 increases expression, function or activity of MFN2 as compared to a baseline control. In another embodiment, an inhibitor of ALCAT1 decreases oxidative stress as measured by reactive oxygen species (ROS) and compared to a normal baseline control. In another preferred embodiment, an inhibitor of ALCAT1 modulates cardiolipin (CL) structure, function, activity, expression or combinations thereof.

In another preferred embodiment, a method of preventing or treating mitochondrial dysfunction in vitro or in vivo, comprises administering to a cell or patient a therapeutically effective amount of a mitofusin molecule. In preferred embodiments, a mitofusin molecule comprises: mitofusin-1 (MFN1), mitofusin-2, (MFN2), fragments, variants, mutants or combinations thereof. Preferably the mitofusin is MFN2.

In one embodiment, an inhibitor of acyl-CoA lysocardiolipin acyltransferase 1 (ALCAT1) is optionally administered to a cell or patient. In preferred embodiments, the inhibitor of ALCAT1 increases expression, function or activity of MFN2 as compared to a baseline control. Other measurements of the effectiveness of the ALCAT1 inhibitor include measuring the oxidative stress as measured by reactive oxygen species (ROS) and compared to a normal baseline control. In another preferred embodiment, an inhibitor of ALCAT1 modulates cardiolipin (CL) structure, function, activity, expression or combinations thereof.

Cardiac Dysfunction, Neurodegenerative and other Diseases: It appears that increased oxidative stress is involved in cardiac hypertrophy and dysfunction. Attenuation of oxidative stress prevents left ventricular remodeling and dysfunction. Oxidative stress is believed to be a principal causative factor of mitochondrial dysfunction and insulin resistance, which has been implicated in the pathogenesis of cardiomyopathy and cardiac dysfunction. Among all the phospholipids, CL is highly sensitive to oxidative damage of its double bonds by reactive oxygen species (ROS), a process known as lipid peroxidation, due to the rich content in polyunsaturated fatty acids and location near the site of ROS production. Hence, CL is the only phospholipid in mitochondria that undergoes early oxidation during apoptosis. Although the molecular mechanisms underlying CL peroxidation remain elusive, it has been shown that increased DHA renders CL highly sensitive to oxidative damage, leading to a vicious cycle of lipid peroxidation and mitochondrial dysfunction. Consequently, DHA content in CL increases in aged heart concurrent with CL deficiency. Ischemia-reperfusion injury of cardiac myocytes causes CL peroxidation, leading to a significant decrease in cytochrome c oxidase activity, which can only be restored by exogenously added CL but not by other phospholipids or peroxidized CL. In particular, the onset of hyperthyroidism in human is associated with elevated oxidative stress and CL peroxidation, which can be mitigated by euthyroidism. Hyperthyroidism stimulates CL remodeling in rodents, leading to a significant increase in polyunsaturated fatty acid and peroxidizability index.

As discussed above, ALCAT1 catalyzes pathological remodeling of CL in response to oxidative stress in diabetes, obesity, and cardiomyopathy, leading to ROS production, mitochondrial dysfunction, and insulin resistance. CL remodeling by ALCAT1 also leads to the production of CL with acyl compositions that are reminiscent of those in heart diseases, including depletion of TLCL and enrichment of DHA. The results herein evidence a role of the enzyme ALCAT1 in the etiology of oxidative stress and cardiac dysfunction.

In a preferred embodiment, a method of treating a patient suffering from cardiomyopathy or at risk of cardiomyopathy, comprises administering to a patient in need thereof, a therapeutically effective amount of an inhibitor of acyl-CoA lysocardiolipin acyltransferase 1 (ALCAT1).

In another preferred embodiment, a patient suffering from or at risk of cardiomyopathy is deficient in PTEN-induced putative kinase 1 (PINK1) as compared to a normal, healthy control. In preferred embodiments, an inhibitor of ALCAT1 is identified if the inhibitor results in increased pink expression, function or activity as compared to a baseline control.

In preferred embodiments, a patient suffering from or at risk of cardiomyopathy expresses hypertrophic comprising: BNP, β-MHC, ANF or ACTA1. In embodiments, an inhibitor of ALCAT1 modulates the expression of one or more of these markers as compared to a baseline control.

In some embodiments, a method of treating a patient suffering from cardiomyopathy or at risk of cardiomyopathy, comprises administering to a patient in need thereof, as part of a therapeutic regimen one or more therapeutic compounds for treating cardiomyopathies, disorders or symptoms thereof.

In another embodiment, a method of preventing or treating a patient suffering from a neurological disease or disorder comprises administering to a patient a therapeutically effective amount of one or more ALCAT1 modulators. Neurological diseases or disorders refers to any disorder of the nervous system and/or visual system. "Neurological disorders" include disorders that involve the central nervous system (brain, brainstem and cerebellum), the peripheral nervous system (including cranial nerves), and the autonomic nervous system (parts of which are located in both central and peripheral nervous system). Neurodegenerative diseases, include, for example, Alzheimer's Disease, stroke, multiple sclerosis etc.

The following is a list of several neurological disorders, symptoms, signs and syndromes that can be treated using compositions and methods according to the present invention: acquired epileptiform aphasia; acute disseminated encephalomyelitis; adrenoleukodystrophy; age-related macular degeneration; agenesis of the corpus callosum; agnosia; Aicardi syndrome; Alexander disease; Alpers' disease; alternating hemiplegia; Alzheimer's disease; Vascular dementia; amyotrophic lateral sclerosis; anencephaly; Angelman syndrome; angiomatosis; anoxia; aphasia; apraxia; arachnoid cysts; arachnoiditis; Anronl-Chiari malformation; arteriovenous malformation; Asperger syndrome; ataxia telegiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome; causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy; chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease; cytomegalovirus infection; dancing eyes-dancing feet syndrome; Dandy-Walker syndrome; Dawson disease; De Morsier's syndrome; Dejerine-Klumke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; fronto-temporal dementia and other "tauopathies"; Gaucher's disease; Gerstmann's syndrome; giant cell arteritis; giant cell inclusion disease; globoid cell leukodystrophy; Guillain-Barre syndrome; HTLV-1-associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile phytanic acid storage disease; infantile refsum disease; infantile spasms; inflammatory myopathy; intracranial cyst; intracranial hypertension; Joubert syndrome; Kearns-Sayre syndrome; Kennedy disease Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gustaut syndrome; Lesch-Nyhan syndrome; leukodystrophy; Lewy body dementia; Lissencephaly; locked-in syndrome; Lou Gehrig's disease (i.e., motor neuron disease or amyotrophic lateral sclerosis); lumbar disc disease; Lyme disease—neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neuron disease; Moyamoya disease; mucopolysaccharidoses; milti-infarct dementia; multifocal motor neuropathy; multiple sclerosis and other demyelinating disorders; multiple system atrophy with postural hypotension; p muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenital; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; post-polio syndrome; postherpetic neuralgia; postinfectious encephalomyelitis; postural hypotension; Prader-Willi syndrome; primary lateral sclerosis; prion diseases; progressive hemifacial atrophy; progressive multifocal leukoencephalopathy; progressive sclerosing poliodystrophy; progressive supranuclear palsy; pseudotumor cerebri; Ramsay-Hunt syndrome (types I and II); Rasmussen's encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus dance; Sandhoff disease; Schilder's disease; schizencephaly; septo-optic dysplasia; shaken baby syndrome; shingles; Shy-Drager syndrome; Sjögren's syndrome; sleep apnea; Soto's syndrome; spasticity; spina bifida; spinal cord injury; spinal cord tumors; spinal muscular atrophy; Stiff-Person syndrome; stroke; Sturge-Weber syndrome; subacute sclerosing panencephalitis; subcortical arteriosclerotic encephalopathy; Sydenham chorea; syncope; syringomyelia; tardive dyskinesia; Tay-Sachs disease; temporal arteritis; tethered spinal cord syndrome; Thomsen disease; thoracic outlet syndrome; Tic Douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau disease; Wallenberg's syndrome; Werdnig-Hoffman disease; West syndrome; whiplash; Williams syndrome; Wildon's disease; and Zellweger syndrome.

In another preferred embodiment, administration of ALCAT1 modulators prevent or treat patients suffering from autoimmune diseases. Examples of autoimmune diseases comprise: rheumatoid arthritis, systemic lupus erythematosus, inflammatory bowel diseases (IBDs) comprising Crohn disease (CD) and ulcerative colitis (UC) which are chronic inflammatory conditions with polygenic susceptibility.

In another preferred embodiment, administration of ALCAT1 modulators prevent or treat patients suffering from diabetic nephropathy and related disorders thereof. An example of such a disorder is diabetic cardiac fibrosis. Other examples are diabetes induced apoptosis in testis and nuage formation in testis.

In another preferred embodiment, ALCAT1 is a prognostic marker for disease progression or outcome or response or resistance to metabolic disease therapies or any disease or disorder associated with mitochondrial dysfunction.

Modulators of ALCAT 1: In preferred embodiments, a method of identifying a modulator of acyl-CoA lysocardiolipin acyltransferase 1 (ALCAT1) comprises contacting a biological sample with a test agent and measuring expression, function or activity of a mitofusin molecule in the biological sample. In preferred embodiments, a test agent is identified as an inhibitor of ALCAT1 if the test agent increases the expression, function or activity of the mitofusin molecule, for example MFN2, as compared to a baseline control.

In another preferred embodiment, a method of identifying a modulator of acyl-CoA lysocardiolipin acyltransferase 1 (ALCAT1) comprises contacting a biological sample with a test agent and measuring expression of hypertrophic markers indicative of cardiomyopathy comprising: BNP, β-MHC, ANF or ACTA1. In preferred embodiments, a test agent is identified as an inhibitor of ALCAT1 if the test agent decreases the expression of hypertrophic markers indicative of cardiomyopathy as compared to a baseline control.

In another preferred embodiment, a method of identifying a modulator of acyl-CoA lysocardiolipin acyltransferase 1 (ALCAT1) expression, function or activity, comprises contacting a biological sample with a test agent; measuring expression of nucleic acid markers or encoded products thereof, indicative of diabetic nephropathy comprising: FAS, TNF, TGF-β, DGAT1, CHREBP1, or SREBP1. In preferred embodiments, a test agent is identified as an inhibitor of ALCAT1 if the test agent modulates expression of FAS, TNF, TGF-β, DGAT1, and SREBP1 as compared to a baseline control.

In another preferred embodiment, a method of identifying a modulator of acyl-CoA lysocardiolipin acyltransferase 1 (ALCAT1) expression, function or activity, comprises contacting a biological sample with a test agent; measuring expression of nucleic acid markers or encoded products thereof, indicative of fatty liver diseases comprising: PPARα, Srebp1c, FAS, ACC1, DGAT1, or CPT1α. In preferred embodiments, a test agent is identified as an inhibitor of ALCAT1 if the test agent modulates expression of PPARα, Srebp1c, FAS, ACC1, DGAT1, and CPT1α as compared to a baseline control.

Examples of fatty liver diseases comprise NAFLD, Alagille syndrome, α-1-antitrypsin deficiency, autoimmune hepatitis, biliary atresia, chronic hepatitis, cancer of the liver, cirrhosis, liver cysts, fatty liver, galactosemia, Gilbert's syndrome, primary biliary cirrhosis, hepatitis A, hepatitis B, hepatitis C, primary sclerosing cholangitis, Reye's syndrome, sarcoidosis, tyrosinemia, type I glycogen storage disease, Wilson's disease, hemochromatosis, and neonatal hepatitis.

In other preferred embodiments, a modulator of acyl-CoA lysocardiolipin acyltransferase 1 (ALCAT1) expression, function or activity, identified by the methods embodied herein.

In other preferred embodiments, a pharmaceutical composition comprises an inhibitor of acyl-CoA lysocardiolipin acyltransferase 1 (ALCAT1) identified by the methods embodied herein.

The biological samples may be obtained from a patient, e.g. cells, fluids etc. The sample can also be synthetic, e.g. peptides, oligonucleotides etc. The sample can also be a transformed cell, a cell transduced with a vector expressing a desired molecule etc. Thus, in embodiments, a biological sample comprises: fluids, peptides, polypeptides, oligonucleotides, polynucleotides, cells, tissues or combinations thereof.

A wide variety of agents can be used to target ALCAT1 and any associated molecules. For example, the associated molecules can be any molecule that is involved in the mechanism of ALCAT1 and can be upstream or downstream in the pathway. For example, the agents may regulate molecules based on the cDNA or regulatory regions, using for example, DNA-based agents, such as antisense inhibitors and ribozymes, can be utilized to target both the introns and exons of the target molecule genes as well as at the RNA level.

Alternatively, the agents may target the molecules based on the amino acid sequences including the three-dimensional protein structures of the target molecules. Protein-based agents, such as human antibody, non-human monoclonal antibody and humanized antibody, can be used to specifically target different epitopes on ALCAT1. Peptides or peptidomimetics can serve as high affinity inhibitors to specifically bind to the promoter site of ALCAT1, inhibiting, for example, expression of ALCAT1. The agents can be identified by a variety of means using the desired outcome to identify which would be suitable, for example, those that modulate MFN2, hypertrophic markers or PTEN-induced putative kinase 1 (PINK1) expression. In addition, ALCAT1 expression, function or activity can also be determined by any assay known in the art. Details are also provided in the examples section which follows.

Labeled Molecules: In another preferred embodiment, the ALCAT1 molecules, ALCAT1 modulators etc., can be radiolabeled. Uses include therapeutic and imaging for diagnostic and prognostic purposes. The label may be a radioactive atom, an enzyme, or a chromophore moiety. Methods for labeling antibodies have been described, for example, by Hunter and Greenwood, *Nature,* 144:945 (1962) and by David et al. *Biochemistry* 13:1014-1021 (1974). Additional methods for labeling antibodies have been described in U.S. Pat. Nos. 3,940,475 and 3,645,090. Methods for labeling oligonucleotide probes have been described, for example, by Leary et al. *Proc. Natl. Acad. Sci.* USA (1983) 80:4045; Renz and Kurz, *Nucl. Acids Res.* (1984) 12:3435; Richardson and Gumport, *Nucl. Acids Res.* (1983) 11:6167; Smith et al. *Nucl. Acids Res.* (1985) 13:2399; and Meinkoth and Wahl, *Anal. Biochem.* (1984) 138:267.

The label may be radioactive. Some examples of useful radioactive labels include $^{32}P$, $^{125}I$, $^{131}I$, and $^{3}H$. Use of radioactive labels have been described in U.K. 2,034,323, U.S. Pat. No. 4,358,535, and U.S. Pat. No. 4,302,204.

Some examples of non-radioactive labels include enzymes, chromophores, atoms and molecules detectable by electron microscopy, and metal ions detectable by their magnetic properties.

Some useful enzymatic labels include enzymes that cause a detectable change in a substrate. Some useful enzymes and their substrates include, for example, horseradish peroxidase (pyrogallol and o-phenylenediamine), β-galactosidase (fluorescein β-D-galactopyranoside), and alkaline phosphatase (5-bromo-4-chloro-3-indolyl phosphate/nitro blue tetrazolium). The use of enzymatic labels has been described in U.K. 2,019,404, EP 63,879, and by Rotman, *Proc. Natl. Acad. Sci. USA*, 47, 1981-1991 (1961).

Useful chromophores include, for example, fluorescent, chemiluminescent, and bioluminescent molecules, as well as dyes. Some specific chromophores useful in the present invention include, for example, fluorescein, rhodamine, Texas red, phycoerythrin, umbelliferone, luminol.

The labels may be conjugated to the antibody or nucleotide probe by methods that are well known in the art. The labels may be directly attached through a functional group on the probe. The probe either contains or can be caused to contain such a functional group. Some examples of suitable functional groups include, for example, amino, carboxyl, sulfhydryl, maleimide, isocyanate, isothiocyanate. Alternatively, labels such as enzymes and chromophores may be conjugated to the antibodies or nucleotides by means of coupling agents, such as dialdehydes, carbodiimides, dimaleimides, and the like.

The label may also be conjugated to the probe by means of a ligand attached to the probe by a method described above and a receptor for that ligand attached to the label. Any of the known ligand-receptor combinations is suitable. Some suitable ligand-receptor pairs include, for example, biotin-avidin or biotin-streptavidin, and antibody-antigen.

In another preferred embodiment, the chimeric fusion molecules of the invention can be used for imaging. In imaging uses, the complexes are labeled so that they can be detected outside the body. Typical labels are radioisotopes, usually ones with short half-lives. The usual imaging radioisotopes, such as $^{123}$I, $^{124}$I, $^{125}$I, $^{131}$I, $^{99m}$TC, $^{186}$Re, $^{188}$Re, $^{64}$Cu, $^{67}$Cu, $^{212}$Bi, $^{213}$Bi, $^{67}$Ga, $^{90}$Y, $^{111}$In, $^{18}$F, $^{3}$H, $^{14}$C, $^{35}$S or $^{32}$P can be used. Nuclear magnetic resonance (NMR) imaging enhancers, such as gadolinium-153, can also be used to label the complex for detection by NMR. Methods and reagents for performing the labeling, either in the polynucleotide or in the protein moiety, are considered known in the art.

Small Molecules: Another example of an agent is a small molecule. In order to identify, small molecules as modulators of ALCAT1, small molecule test compounds can initially be members of an organic or inorganic chemical library. As used herein, "small molecules" refers to small organic or inorganic molecules of molecular weight below about 3,000 Daltons. The small molecules can be natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, Solid-Supported Combinatorial and Parallel Synthesis of Small-Molecular-Weight Compound Libraries, Pergamon-Elsevier Science Limited (1998), and include those such as the "split and pool" or "parallel" synthesis techniques, solid-phase and solution-phase techniques, and encoding techniques (see, for example, Czarnik, *Curr. Opin. Chem. Bio.*, 1:60 (1997). In addition, a number of small molecule libraries are commercially available.

Small molecules may include cyclical carbon or heterocyclic structures and/or aromatic or polyaromatic structures substituted with one or more of the above functional groups. Also of interest as small molecules are structures found among biomolecules, including peptides, saccharides, fatty acids, steroids, purines, pyrimidines, derivatives, structural analogs or combinations thereof. Such compounds may be screened to identify those of interest, where a variety of different screening protocols are known in the art.

The small molecule may be derived from a naturally occurring or synthetic compound that may be obtained from a wide variety of sources, including libraries of synthetic or natural compounds. For example, numerous means are available for random and directed synthesis of a wide variety of organic compounds and biomolecules, including the preparation of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known small molecules may be subjected to directed or random chemical modifications, such as acylation, alkylation, esterification, amidification, etc. to produce structural analogs.

As such, the small molecule may be obtained from a library of naturally occurring or synthetic molecules, including a library of compounds produced through combinatorial means, i.e., a compound diversity combinatorial library. Combinatorial libraries, as well as methods for the production and screening, are known in the art.

Chemical Libraries: Developments in combinatorial chemistry allow the rapid and economical synthesis of hundreds to thousands of discrete compounds. These compounds are typically arrayed in moderate-sized libraries of small molecules designed for efficient screening. Combinatorial methods can be used to generate unbiased libraries suitable for the identification of novel compounds. In addition, smaller, less diverse libraries can be generated that are descended from a single parent compound with a previously determined biological activity. In either case, the lack of efficient screening systems to specifically target therapeutically relevant biological molecules produced by combinational chemistry such as inhibitors of important enzymes hampers the optimal use of these resources.

A combinatorial chemical library is a collection of diverse chemical compounds generated by either chemical synthesis or biological synthesis, by combining a number of chemical "building blocks," such as reagents. For example, a linear combinatorial chemical library, such as a polypeptide library, is formed by combining a set of chemical building blocks (amino acids) in a large number of combinations, and potentially in every possible way, for a given compound length (i.e., the number of amino acids in a polypeptide compound). Millions of chemical compounds can be synthesized through such combinatorial mixing of chemical building blocks.

A "library" may comprise from 2 to 50,000,000 diverse member compounds. Preferably, a library comprises at least 48 diverse compounds, preferably 96 or more diverse compounds, more preferably 384 or more diverse compounds, more preferably, 10,000 or more diverse compounds, preferably more than 100,000 diverse members and most preferably more than 1,000,000 diverse member compounds. By "diverse" it is meant that greater than 50% of the compounds in a library have chemical structures that are not identical to any other member of the library. Preferably, greater than 75% of the compounds in a library have chemical structures that are not identical to any other member of the collection, more preferably greater than 90% and most preferably greater than about 99%.

The preparation of combinatorial chemical libraries is well known to those of skill in the art. For reviews, see Thompson et al., Synthesis and application of small molecule libraries, *Chem Rev* 96:555-600, 1996; Kenan et al., Exploring molecular diversity with combinatorial shape libraries, *Trends Biochem Sci* 19:57-64, 1994; Janda, Tagged versus untagged libraries: methods for the generation and screening of combinatorial chemical libraries, *Proc Natl Acad Sci USA.* 91:10779-85, 1994; Lebl et al., One-bead-one-structure combinatorial libraries, *Biopolymers* 37:177-98, 1995; Eichler et al., Peptide, peptidomimetic, and organic synthetic combinatorial libraries, *Med Res Rev.* 15:481-96, 1995; Chabala, Solid-phase combinatorial chemistry and novel tagging methods for identifying leads, *Curr Opin Biotechnol.* 6:632-9, 1995; Dolle, Discovery of enzyme inhibitors through combinatorial chemistry, *Mol Divers.* 2:223-36, 1997; Fauchere et al., Peptide and non-peptide lead discovery using robotically synthesized soluble libraries, *Can J. Physiol Pharmacol.* 75:683-9, 1997; Eichler et al., Generation and utilization of synthetic combinatorial libraries, *Mol Med Today* 1: 174-80, 1995; and Kay et al., Identification of enzyme inhibitors from phage-displayed combinatorial peptide libraries, *Comb Chem High Throughput Screen* 4:535-43, 2001.

Other chemistries for generating chemical diversity libraries can also be used. Such chemistries include, but are not limited to, peptoids (PCT Publication No. WO 91/19735); encoded peptides (PCT Publication WO 93/20242); random bio-oligomers (PCT Publication No. WO 92/00091); benzodiazepines (U.S. Pat. No. 5,288,514); diversomers, such as hydantoins, benzodiazepines and dipeptides (Hobbs, et al., *Proc. Nat. Acad. Sci. USA*, 90:6909-6913 (1993)); vinylogous polypeptides (Hagihara, et al., *J. Amer. Chem. Soc.* 114:6568 (1992)); nonpeptidal peptidomimetics with β-D-glucose scaffolding (Hirschmann, et al., *J. Amer. Chem. Soc.*, 114:9217-9218 (1992)); analogous organic syntheses of small compound libraries (Chen, et al., *J. Amer. Chem. Soc.*, 116:2661 (1994)); oligocarbamates (Cho, et al., *Science*, 261:1303 (1993)); and/or peptidyl phosphonates (Campbell, et al., *J. Org. Chem.* 59:658 (1994)); nucleic acid libraries (see, Ausubel, Berger and Sambrook, all supra); peptide nucleic acid libraries (see, e.g., U.S. Pat. No. 5,539,083); antibody libraries (see, e.g., Vaughn, et al., *Nature Biotechnology*, 14(3):309-314 (1996) and PCT/US96/10287); carbohydrate libraries (see, e.g., Liang, et al., *Science*, 274:1520-1522 (1996) and U.S. Pat. No. 5,593,853); small organic molecule libraries (see, e.g., benzodiazepines, Baum C&E News, Jan. 18, page 33 (1993); isoprenoids (U.S. Pat. No. 5,569,588); thiazolidinones and metathiazanones (U.S. Pat. No. 5,549,974); pyrrolidines (U.S. Pat. Nos. 5,525,735 and 5,519,134); morpholino compounds (U.S. Pat. No. 5,506,337); benzodiazepines (U.S. Pat. No. 5,288,514); and the like.

Devices for the preparation of combinatorial libraries are commercially available (see, e.g., 357 MPS, 390 MPS, Advanced Chem. Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., Chem-Star, Ltd., Moscow, RU, 3D Pharmaceuticals, Exton, Pa., Martek Bio sciences, Columbia, Md., etc.).

In addition to targeting ALCAT1 and associated molecules, agents may also be used which compete for binding sites or signaling sites.

In embodiments, an agent modulates the interactions of ALCAT1 promoters. Examples of agents, include without limitation: antibodies, aptamers, RNAi, small molecules, high-affinity binding of specific synthetic or natural peptides that interfere with the assembly of the transcription factor-DNA binding and thus inhibit complex formation. In some aspects the agent inhibits ALCAT1 expression (e.g. by siRNA).

One embodiment of the invention includes isolated antibodies, or fragments of those antibodies, that bind to, for example, ALCAT1. As known in the art, the antibodies can be, for example, polyclonal, oligoclonal, monoclonal, chimeric, humanized, and/or fully human antibodies. Embodiments of the invention described herein also provide cells for producing these antibodies.

Interference RNA: Detailed methods of producing the can be obtained using a number of techniques known to those of skill in the art. For example, the siRNA can be chemically synthesized or recombinantly produced using methods known in the art, such as the Drosophila in vitro system described in U.S. published application 2002/0086356 of Tuschl et al., the entire disclosure of which is herein incorporated by reference.

The ability of an RNAi containing a given target sequence to cause RNAi-mediated degradation of the target mRNA can be evaluated using standard techniques for measuring the levels of RNA or protein in cells. For example, RNA of the invention can be delivered to cultured cells, and the levels of target mRNA can be measured by Northern blot or dot blotting techniques, or by quantitative RT-PCR. RNAi-mediated degradation of target mRNA by an siRNA containing a given target sequence can also be evaluated with animal models, such as mouse models. RNAi-mediated degradation of the target mRNA can be detected by measuring levels of the target mRNA or protein in the cells of a subject, using standard techniques for isolating and quantifying mRNA or protein as described above.

In a preferred embodiment, siRNA molecules target overlapping regions of a desired sense/antisense locus, thereby modulating both the sense and antisense transcripts e.g. targeting dendrin. In another preferred embodiment, a composition comprises siRNA molecules, of either one or more, and/or, combinations of siRNAs, siRNAs that overlap a desired target locus, and/or target both sense and antisense (overlapping or otherwise). These molecules can be directed to any target that is desired for potential therapy of any disease or abnormality. Theoretically there is no limit as to which molecule is to be targeted. Furthermore, the technologies taught herein allow for tailoring therapies to each individual.

In preferred embodiments, the oligonucleotides can be tailored to individual therapy, for example, these oligonucleotides can be sequence specific for allelic variants in individuals, the up-regulation or inhibition of a target can be manipulated in varying degrees, such as for example, 10%, 20%, 40%, 100% expression relative to the control. That is, in some patients it may be effective to increase or decrease target gene expression by 10% versus 80% in another patient.

Modulation (up-regulation or inhibition) of gene expression may be quantified by measuring either the endogenous target RNA or the protein produced by translation of the target RNA. Techniques for quantifying RNA and proteins are well known to one of ordinary skill in the art. In certain preferred embodiments, gene expression is inhibited by at least 10%, preferably by at least 33%, more preferably by at least 50%, and yet more preferably by at least 80%. In particularly preferred embodiments, of the invention gene expression is inhibited by at least 90%, more preferably by at least 95%, or by at least 99% up to 100% within cells in the organism. In certain preferred embodiments (e.g. MFN2, PINK1), gene expression is up-regulated by at least 10%, preferably by at least 33%, more preferably by at least 50%, and yet more preferably by at least 80%. In particularly preferred embodiments, of the invention gene expression is up-regulated by at least 90%, more preferably by at least 95%, or by at least 99% up to 100% within cells in the organism.

Selection of appropriate RNAi is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of RNAi that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

In a preferred embodiment, small interfering RNA (siRNA) either as RNA itself or as DNA, is delivered to a cell using aptamers or any other type of delivery vehicle known in the art. In certain embodiments, the nucleic acid molecules of the present disclosure can be synthesized separately and joined together post-synthetically, for example, by ligation (Moore et al., Science 256:9923, 1992; Draper et al., PCT Publication No. WO 93/23569; Shabarova et al., Nucleic Acids Res. 19:4247, 1991; Bellon et al., Nucleosides & Nucleotides 16:951, 1997; Bellon et al., Bioconjugate Chem. 8:204, 1997), or by hybridization following synthesis or deprotection.

In further embodiments, oligonucleotides mediating interference can be made as single or multiple transcription products expressed by a polynucleotide vector encoding one or more siRNAs and directing their expression within host cells. An siRNA or analog thereof of this disclosure may be further comprised of a nucleotide, non-nucleotide, or mixed nucleotide/non-nucleotide linker that joins the aptamers and siRNAs. In one embodiment, a nucleotide linker can be a linker of more than about 2 nucleotides length up to about 50 nucleotides in length. In another embodiment, the nucleotide linker can be a nucleic acid aptamer. By "aptamer" or "nucleic acid aptamer" as used herein is meant a nucleic acid molecule that binds specifically to a target molecule wherein the nucleic acid molecule has sequence that comprises a sequence recognized by the target molecule in its natural setting. Alternately, an aptamer can be a nucleic acid molecule that binds to a target molecule wherein the target molecule does not naturally bind to a nucleic acid. The target molecule can be any molecule of interest. For example, the aptamer can be used to bind to a ligand-binding domain of a protein, thereby preventing interaction of the naturally occurring ligand with the protein. This is a non-limiting example and those in the art will recognize that other embodiments can be readily generated using techniques generally known in the art (see, e.g., Gold et al., Annu. Rev. Biochem. 64:763, 1995; Brody and Gold, J. Biotechnol. 74:5, 2000; Sun, Curr. Opin. Mol. Ther. 2:100, 2000; Kusser, J. Biotechnol. 74:27, 2000; Hermann and Patel, Science 287:820, 2000; and Jayasena, Clinical Chem. 45:1628, 1999).

The invention may be used against protein coding gene products as well as non-protein coding gene products. Examples of non-protein coding gene products include gene products that encode ribosomal RNAs, transfer RNAs, small nuclear RNAs, small cytoplasmic RNAs, telomerase RNA, RNA molecules involved in DNA replication, chromosomal rearrangement and the like.

In accordance with the invention, siRNA oligonucleotide therapies comprise administered siRNA oligonucleotide which contacts (interacts with) the targeted mRNA from the gene, whereby expression of the gene is modulated. Such modulation of expression suitably can be a difference of at least about 10% or 20% relative to a control, more preferably at least about 30%, 40%, 50%, 60%, 70%, 80%, or 90% difference in expression relative to a control. It will be particularly preferred where interaction or contact with an siRNA oligonucleotide results in complete or essentially complete modulation of expression relative to a control, e.g., at least about a 95%, 97%, 98%, 99% or 100% inhibition of or increase in expression relative to control. A control sample for determination of such modulation can be comparable cells (in vitro or in vivo) that have not been contacted with the siRNA oligonucleotide.

In another preferred embodiment, the nucleobases in the siRNA may be modified to provided higher specificity and affinity for a target mRNA. For example nucleobases may be substituted with LNA monomers, which can be in contiguous stretches or in different positions. The modified siRNA, preferably has a higher association constant ($K_a$) for the target sequences than the complementary sequence. Binding of the modified or non-modified siRNA's to target sequences can be determined in vitro under a variety of stringency conditions using hybridization assays and as described in the examples which follow.

Chimeric/modified RNAi's: In accordance with this invention, persons of ordinary skill in the art will understand that mRNA includes not only the coding region which carries the information to encode a protein using the three letter genetic code, including the translation start and stop codons, but also associated ribonucleotides which form a region known to such persons as the 5'-untranslated region, the 3'-untranslated region, the 5' cap region, intron regions and intron/exon or splice junction ribonucleotides. Thus, oligonucleotides may be formulated in accordance with this invention which are targeted wholly or in part to these associated ribonucleotides as well as to the coding ribonucleotides. In preferred embodiments, the oligonucleotide is targeted to a translation initiation site (AUG codon) or sequences in the coding region, 5' untranslated region or 3'-untranslated region of an mRNA. The functions of messenger RNA to be interfered with include all vital functions such as translocation of the RNA to the site for protein translation, actual translation of protein from the RNA, splicing or maturation of the RNA and possibly even independent catalytic activity which may be engaged in by the RNA. The overall effect of such interference with the RNA function is to cause interference with protein expression.

Other agents: These can include any synthetic or natural peptides, glycoproteins, enzymes, modulators of signaling, inhibitors of assembly of transcription or translational factor complexes, organic or inorganic molecules and the like.

Other embodiments of the invention include isolated nucleic acid molecules encoding any of the targeted binding agents, antibodies or fragments thereof as described herein, vectors having isolated nucleic acid molecules or a host cell transformed with any of such nucleic acid molecules. It should be realized that embodiments of the invention also include any nucleic acid molecule which encodes an antibody or fragment of an antibody of the invention including nucleic acid sequences optimized for increasing yields of antibodies or fragments thereof when transfected into host cells for antibody production.

Microarrays: Identification of a nucleic acid sequence capable of binding to ALCAT1 and associated molecules can be achieved by immobilizing a library of nucleic acids onto the substrate surface so that each unique nucleic acid is located at a defined position to form an array. In general, the immobilized library of nucleic acids are exposed to a biomolecule or candidate agent under conditions which favored binding of the biomolecule to the nucleic acids. Non-specifically binding biomolecules could be washed away using mild to stringent buffer conditions depending on the level of specificity of binding desired. The nucleic acid array would then be analyzed to determine which nucleic acid sequences bound to the biomolecule. Preferably the biomolecules would carry a fluorescent tag for use in detection of the location of the bound nucleic acids.

An assay using an immobilized array of nucleic acid sequences may be used for determining the sequence of an unknown nucleic acid; single nucleotide polymorphism (SNP) analysis; analysis of gene expression patterns from a particular species, tissue, cell type, gene identification; etc.

Additional diagnostic uses for oligonucleotides designed from the sequences encoding a desired gene expression product may involve the use of PCR. These oligomers may be chemically synthesized, generated enzymatically, or produced in vitro. Oligomers will preferably contain a fragment of a polynucleotide encoding the expression products, or a fragment of a polynucleotide complementary to the polynucleotides, and will be employed under optimized conditions for identification of a specific gene. Oligomers may also be employed under less stringent conditions for detection or quantitation of closely-related DNA or RNA sequences.

In further embodiments, oligonucleotides or longer fragments derived from any of the polynucleotide sequences, may be used as targets in a microarray. The microarray can be used to monitor the identity and/or expression level of large numbers of genes and gene transcripts simultaneously to identify genes with which target genes or its product interacts and/or to assess the efficacy of candidate therapeutic agents in regulating expression products of genes that mediate, for example, neurological disorders. This information may be used to determine gene function, and to develop and monitor the activities of therapeutic agents.

Microarrays may be prepared, used, and analyzed using methods known in the art (see, e.g., Brennan et al., 1995, U.S. Pat. No. 5,474,796; Schena et al., 1996, *Proc. Natl. Acad. Sci. U.S.A.* 93: 10614-10619; Baldeschweiler et al., 1995, PCT application WO95/251116; Shalon, et al., 1995, PCT application WO95/35505; Heller et al., 1997, *Proc. Natl. Acad. Sci. U.S.A.* 94: 2150-2155; and Heller et al., 1997, U.S. Pat. No. 5,605,662). In other embodiments, a microarray comprises peptides, or other desired molecules which can be assayed to identify a candidate agent.

Another technique for drug screening provides for high throughput screening of compounds having suitable binding affinity to the protein of interest (see, e.g., Geysen et al., 1984, PCT application WO84/03564). In this method, large numbers of different small test compounds are synthesized on a solid substrate. The test compounds are reacted with identified genes, or fragments thereof, and washed. Bound molecules are then detected by methods well known in the art. Alternatively, non-neutralizing antibodies can be used to capture the peptide and immobilize it on a solid support.

The methods of screening of the invention comprise using screening assays to identify, from a library of diverse molecules, one or more compounds having a desired activity. A "screening assay" is a selective assay designed to identify, isolate, and/or determine the structure of, compounds within a collection that have a preselected activity. By "identifying" it is meant that a compound having a desirable activity is isolated, its chemical structure is determined (including without limitation determining the nucleotide and amino acid sequences of nucleic acids and polypeptides, respectively) the structure of and, additionally or alternatively, purifying compounds having the screened activity). Biochemical and biological assays are designed to test for activity in a broad range of systems ranging from protein-protein interactions, enzyme catalysis, small molecule-protein binding, to cellular functions. Such assays include automated, semi-automated assays and HTS (high throughput screening) assays.

In HTS methods, many discrete compounds are preferably tested in parallel by robotic, automatic or semi-automatic methods so that large numbers of test compounds are screened for a desired activity simultaneously or nearly simultaneously. It is possible to assay and screen up to about 6,000 to 20,000, and even up to about 100,000 to 1,000,000 different compounds a day using the integrated systems of the invention.

Typically in HTS, target molecules are administered or cultured with isolated cells with modulated receptors, including the appropriate controls.

In one embodiment, screening comprises contacting each cell culture with a diverse library of member compounds, some of which are ligands of the target, under conditions where complexes between the target and ligands can form, and identifying which members of the libraries are present in such complexes. In another non limiting modality, screening comprises contacting a target enzyme with a diverse library of member compounds, some of which are inhibitors (or activators) of the target, under conditions where a product or a reactant of the reaction catalyzed by the enzyme produce a detectable signal. In the latter modality, inhibitors of target enzyme decrease the signal from a detectable product or increase a signal from a detectable reactant (or vice-versa for activators).

In one embodiment the invention provides soluble assays using any of the molecules embodied herein (e.g. ALCAT1 or modulators of ALCAT1, MFN2, PTEN, etc.), or a cell or tissue expressing any of these molecules protein, either naturally occurring or recombinant. In another embodiment, the invention provides solid phase based in vitro assays in a high throughput format, where, for example, the ALCAT1 molecule or fragment thereof, is attached to a solid phase substrate. Any one of the assays described herein can be adapted for high throughput screening, e.g., ligand binding, cellular proliferation, cell surface marker flux, radiolabeled GTP binding, second messenger flux, e.g., $Ca^{2+}$, IP3, cGMP, or cAMP, cytokine production, etc In the high throughput assays of the invention, either soluble or solid state, it is possible to screen up to several thousand different modulators or ligands in a single day.

This methodology can be used for ALCAT1 proteins in vitro, or for cell-based or membrane-based assays comprising an ALCAT1 protein. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100 to about 1500 different compounds. It is possible to assay many plates per day; assay screens for up to about 6,000, 20,000, 50,000, or more than 100,000 different compounds are possible using the integrated systems of the invention.

For a solid state reaction, the protein of interest or a fragment thereof, e.g., an extracellular domain, or a cell or membrane comprising the protein of interest or a fragment thereof as part of a fusion protein can be bound to the solid state component, directly or indirectly, via covalent or non covalent linkage e.g., via a tag. The tag can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis, Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selection family, and the like; see, e.g., Pigott & Power, The Adhesion Molecule Facts Book I (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and poly- acetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank & Doring, *Tetrahedron* 44:60316040 (1988) (describing synthesis of various peptide sequences on cellulose disks); Fodor et al., *Science*, 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

Administration of Compositions to Patients

The compositions or agents identified by the methods described herein may be administered to animals including human beings in any suitable formulation. For example, the compositions for modulating protein degradation may be formulated in pharmaceutically acceptable carriers or diluents such as physiological saline or a buffered salt solution. Suitable carriers and diluents can be selected on the basis of mode and route of administration and standard pharmaceutical practice. A description of exemplary pharmaceutically acceptable carriers and diluents, as well as pharmaceutical formulations, can be found in Remington's Pharmaceutical Sciences, a standard text in this field, and in USP/NF. Other substances may be added to the compositions to stabilize and/or preserve the compositions.

The compositions of the invention may be administered to animals by any conventional technique. The compositions may be administered directly to a target site by, for example, surgical delivery to an internal or external target site, or by catheter to a site accessible by a blood vessel. Other methods of delivery, e.g., liposomal delivery or diffusion from a device impregnated with the composition, are known in the art. The compositions may be administered in a single bolus, multiple injections, or by continuous infusion (e.g., intravenously). For parenteral administration, the compositions are preferably formulated in a sterilized pyrogen-free form.

The agents or compounds can be administered with one or more therapies. The chemotherapeutic agents may be administered under a metronomic regimen. As used herein, "metronomic" therapy refers to the administration of continuous low-doses of a therapeutic agent.

Dosage, toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of a compound (i.e., an effective dosage) means an amount sufficient to produce a therapeutically (e.g., clinically) desirable result. The compositions can be administered one from one or more times per day to one or more times per week; including once every other day. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compounds of the invention can include a single treatment or a series of treatments.

Formulations: While it is possible for a composition to be administered alone, it is preferable to present it as a pharmaceutical formulation. The active ingredient may comprise, for topical administration, from 0.001% to 10% w/w, e.g., from 1% to 2% by weight of the formulation, although it may comprise as much as 10% w/w but preferably not in excess of 5% w/w and more preferably from 0.1% to 1% w/w of the formulation. The topical formulations of the present invention, comprise an active ingredient together with one or more acceptable carrier(s) therefore and optionally any other therapeutic ingredients(s). The carrier(s) must be "acceptable" in the sense of being compatible with the other ingredients of the formulation and not deleterious to the recipient thereof.

Formulations suitable for topical administration include liquid or semi-liquid preparations suitable for penetration through the skin to the site of where treatment is required, such as liniments, lotions, creams, ointments or pastes, and drops suitable for administration to the eye, ear, or nose. Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified and sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document, applicants do not admit any particular reference is "prior art" to their invention. Embodiments of inventive compositions and methods are illustrated in the following examples.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Example 1

Cardiolipin Remodeling by ALCAT1 Controls Mitochondrial Biogenesis and mtDNA Fidelity through Modulation of MFN2 Expression The present investigation sought to advance the understanding of molecular mechanisms by which ALCAT1 regulates mitochondrial dysfunction associated with oxidative stress. In the process, an unexpected role of ALCAT1 in regulating mitochondrial fusion and mtDNA fidelity, implicating a critical role of ALCAT1 in MFN2 deficiency and mitochondrial fragmentation in age-related diseases was identified.

Materials and Methods

ALCAT1 Knockout Mice: The generation of the ALCAT1 knockout mice and measurement of oxygen consumption rate (OCR) were as previously described (Li J, et al. (2010). Cell Metab 12(2):154-165). All experiments used littermate control of matched age and sex and in accordance with approval of institutional animal care and use protocols according to NIH guidelines (NIH publication No. 86-23, 1985).

Reagents: Antibodies used in the present studies include monoclonal antibodies to prohibitin and calnexin, which were purchased from Santa Cruz Biotechnology (Santa Cruz, Calif.). Monoclonal antibodies to MFN1, MFN2 and OPA1 were from Abcam. Donkey anti-Rabbit and donkey anti mouse IgG horseradish peroxidase-conjugated antibodies were purchased from GE Healthcare (Piscataway, N.J.). Donkey anti-mouse and donkey anti-rabbit FITC-conjugated antibodies were from Santa Cruz Biotechnology. Carbonylcyanide p-trifluoromethoxyphenylhydrazone (FCCP), rotenone, antimycin, oligomycin and diphenyleneiodonium sulfate (DPI) were purchased from Invitrogen.

Animal Care: Male and female C57BL/6J mice, 4 to 6 weeks of age, were purchased from Jackson Laboratory (Bar Harbor, Me.). All animals were maintained in an environmentally controlled facility with diurnal light cycle and free access to water and either a standard rodent chow (Harland Teklad 2018, Madison, Wis.) or a high-fat diet from Research Diets (New Brunswick, N.J.; Cat. #D12492). All experiments involving animals were performed in compliance with approved institutional animal care and use protocols according to NIH guidelines (NIH publication No. 86-23, 1985).

Immunofluorescence Confocal Microscopy and Image Analysis: For immunofluorescence staining, the cells were fixed in 4% paraformaldehyde for 10 min, washed twice with PBS, and then permeabilized with 0.1% Triton X-100 for 10 min. Fixed cells were pre-incubated for 30 min in PBS containing 5% bovine serum albumin at room temperature. Cells were stained with primary antibody (anti-Myc monoclonal antibody, 1:500 dilution) for 3h at room temperature followed by incubation with secondary antibody conjugated with FITC (1:1000 dilution, Santa Cruz). For mitochondrial staining, cells were stained with Mitotracker Red (final concentration 100 nM) for 5 min in 37° C. incubator, washed with PBS three times, 5 min each wash. The cells were then analyzed under confocal microscopy (Leica TCS SP2 AOBS) equipped with a bipolar temperature controller. Images were processed using Adobe Photoshop 7.0, and quantitative analyses were performed using ImageJ (National Institutes of Health). All experiments were performed at least three times with similar results.

EM Analysis: Cells were fixed in 4% paraformaldehyde and 5% glutaraldehyde, stained sequentially in 2% $OsO_4$ and 1% uranyl acetate, dehydrated by a series of ethanol washes and embedded in Embed-812 resin for sectioning and analysis. Samples were analyzed with the use of a JEOL 1200EX transmission electron microscope.

mtDNA Mutation Assays: For mtDNA isolation, MEF and C2C12 cells were homogenized and a mitochondrial fraction was isolated as previously described (Li et al., (2010). Cell Metab 12(2):154-165). Mitochondria were then lysed in the presence of 0.5% SDS and 0.2 mg/ml proteinase K in 10 mM Tris-HCl, 0.15M NaCl, and 0.005M EDTA. mtDNA was purified by phenol/chloroform extraction and ethanol precipitation. The random mutation capture assays were performed as previously described (Chen et al., 2010. Cell 141(2):280-289). Briefly, mtDNA was digested with TaqI for 5h and then diluted in a 96 well format and probed with primers flanking the TaqI restriction site in order to detect mtDNA genomes that contained a mutation in the TaqI restriction site. A control pair of primers was used to detect the amount of mtDNA genomes that was interrogated. PCR was carried out in 20 µl reactions using the ABI STEPONEPLUS™ and 95° C. SYBR®GREEN PCR Master Mix. Quantitative PCR amplification was carried out using the following programs: step 1, 95° C. for 10 min; step 2, for 15 s; step 3, 60° C. for 1 min; step 4, go to step two 40 times; step 5, melt curve from 65° C. to 95° C.

Mitochondrial Fusion Assay: C2C12 cells stably expressing ACLAT1 or vector control were seeded with $5 \times 10^5$ per 6 cm⁻ plate, and transfected with mitochondria-targeted green fluorescent protein (mtEGFP) or with mitochondria-targeted dsRED2 (mtDsred2), respectively. After 30 h, individual pools of cells respectively expressing mtEGFP and mtDsRed2 were mixed and coplated at a 1:1 ratio onto 13-mm round cover slips. Fusion was then induced after 6 h by a 60-sec treatment with a 50% (wt/vol) solution of PEG 1500 in PBS (Sigma), followed by extensive washes in DMEM supplemented with 10% FCS. To inhibit protein synthesis, cycloheximide (20 µg/ml) was added 30 min before fusion and kept in all solutions and cell culture medium used subsequently until cells were fixed for 10 min with ice-cold 4% formaldehyde in PBS. After three washes with PBS, cover slips were mounted on slides and kept in dark box, 4° C. overnight.

Mouse Embryonic Fibroblast (MEF) Preparation: The female mice at 12.5th embryonic day were euthanized. Embryos were dissected out on a dish with HBSS. Head, limbs and internal organs were removed. The remaining embryo was minced with a scalpel or razor blade, and transferred to a 15 ml tube with 4 ml collagenase solution and then with 4 ml to wash the dish to get all the embryonic parts. Tubes were rotated for 30-60 min in a 37° C. incubator until all the tissue chunks were gone. The digested solution was filtered through 100 µm mesh to 50 ml tubes filled with chilled DMEM (30 ml). The samples were centrifuged at 1200 rpm for 5 min and the cell pellet was washed again with 25 ml of DMEM. Then cells were then seeded with complete medium.

XF24 Bioenergetic Assay: Oxygen consumption rate (OCR) was measured using the Seahorse XF24 analyzer (Seahorse Bioscience) as previously described (Li et al., 2010 Cell Metab 12(2):154-165). After equilibration, the test reagent were preloaded in the reagent delivery chambers of the $O_2$ sensor cartridge and injected into the wells after the XF respirometry read the basal $O_2$ consumption rate. $O_2$ consumption rates (pmoles/minutes) were obtained. After the baseline measurement, 70 μl of a testing agent prepared in assay medium was then injected into each well to reach the desired final concentration. This was followed by mixing for 2 minutes to expedite compound exposure to cellular proteins and OCR measurements were then carried out.

Statistical Analysis: Statistical comparisons were done using two-tailed non-paired t tests to determine the difference between the two C2C12 cell lines and between ALCAT1$^{-/-}$ and wild-type mice. Data are expressed as means±SEM. p<0.05 was considered statistically significant.

Results

Figure 8:
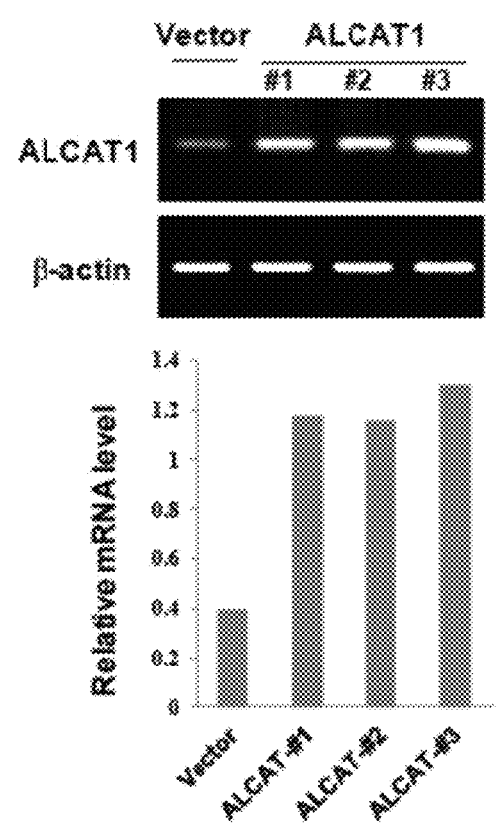
FIG. 8 shows the RT-PCR analysis of ALCAT1 mRNA expression level in C2C12 cells stably expressing ALCAT1. C2C12 cells stably transfected with ALCAT1 expression vector or an empty vector were selected for individual clones. The C2C12 cell lines stably expressing ALCAT1 or vector control were analyzed for ALCAT1 mRNA expression by RT-PCR analysis.
Figures 9A, 9B, 9C, 9D:
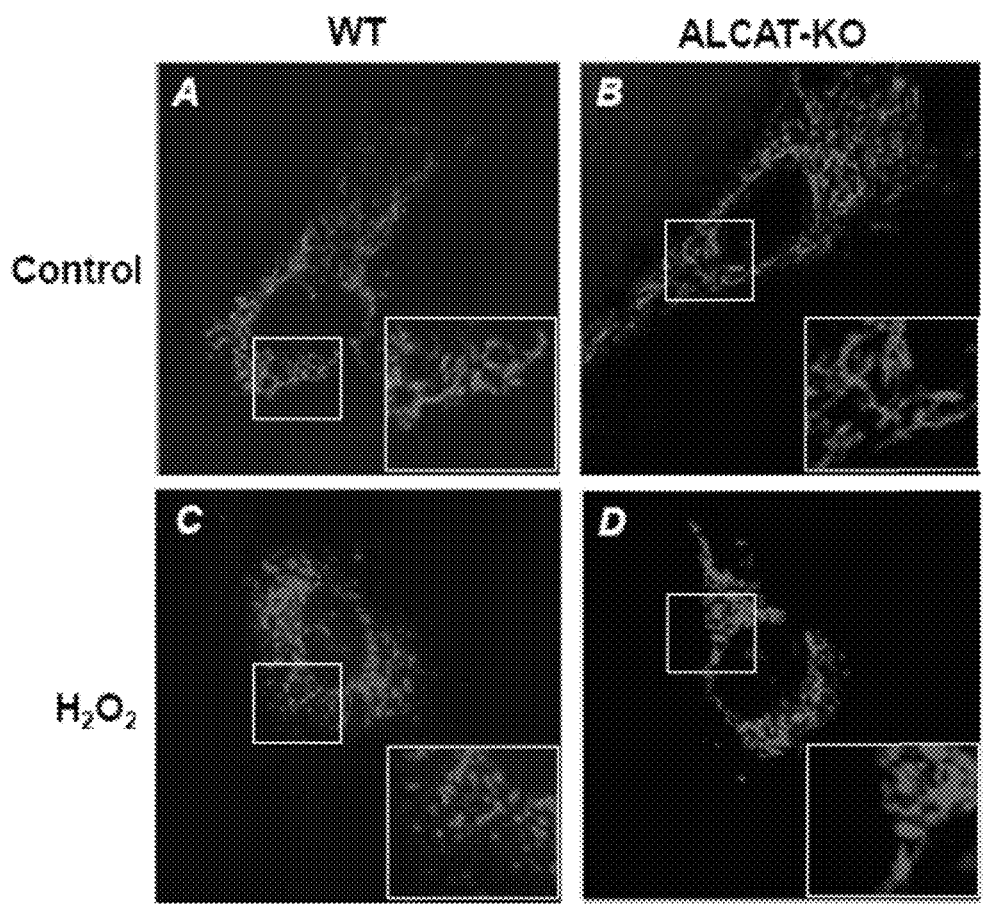
FIGS. 9A-9D show that ALCAT1 deficiency prevented mitochondrial fragmentation in response to oxidative stress in MEFs. Isolated MEFs from ALCAT1 knockout (KO) mice (FIGS. 9B & 9D) and the wild type (WT) control mice (FIGS. 9A and 9C) were cultured in the absence (FIGS. 9A & 9B) or presence (FIGS. 9C & 9D) of 0.5 mM of $H_2O_2$ for 2 hour, followed by analysis of mitochondrial network by staining with Mitotracker Red. In contrast to vector control, ALCAT1 deficiency prevented mitochondrial fragmentation in response to oxidative stress.

ALCAT1 Causes Mitochondrial Fragmentation and mtDNA Instability in C2C12 Cells. ALCAT1 is a lysocardiolipin acyltransferase that catalyzes pathological CL remodeling, leading to ROS production and mitochondrial dysfunction in diabetes and obesity. ROS causes mitochondrial fragmentation which has been implicated in age-related diseases. Here, a role of ALCAT1 overexpression was investigated in regulating mitochondria and ER morphology in C2C12 cell lines stably transfected with flag-tagged ALCAT1 cDNA (C2C12-A1) or vector control (C2C12-V). The mRNA expression level of ALCAT1 in the C2C12-A1 cells is only three fold higher than the C2C12-V cells (FIG. 8), and matches the level of ALCAT1 expression induced by the onset of diabetes and obesity. As shown in FIGS. 1A-1I (quantified in FIG. 1 1C), ALCAT1 overexpression causes mitochondrial fragmentation, as evidenced by more than 95% of fragmented mitochondria in the C2C12-A1 cells. Additionally, ALCAT1 overexpression led to shortened mitochondria and mitochondrial swelling in C2C12-A1 cells (FIG. 1E, highlighted in FIG. 1G), as analyzed by electron microscopic (EM) analysis. Furthermore, ALCAT1 overexpression also caused ER dilation when compared with vector control (FIG. 1D, highlighted in FIG. 1F with dotted lines), which is consistent with previously reported localization of ALCAT1 at mitochondria-associated membrane (MAM).

Mitochondrial fragmentation is often associated with mtDNA instability. Given the abnormal mitochondrial morphology, the role of ALCAT1 in regulating mtDNA copy number and mutation rates was investigated by RT-PCR analysis. Remarkably, ALCAT1 overexpression significantly depleted mtDNA copy number in C2C12-A1 cells (FIG. 1H). Furthermore, ALCAT1 overexpression also significantly increased mtDNA mutation rate (FIG. 1I), providing evidence for a major role of ALCAT1 in regulating mitochondrial mass and mtDNA stability.

Figures 2A, 2B, 2C, 2D, 2E, 2F, 2G, 2H:
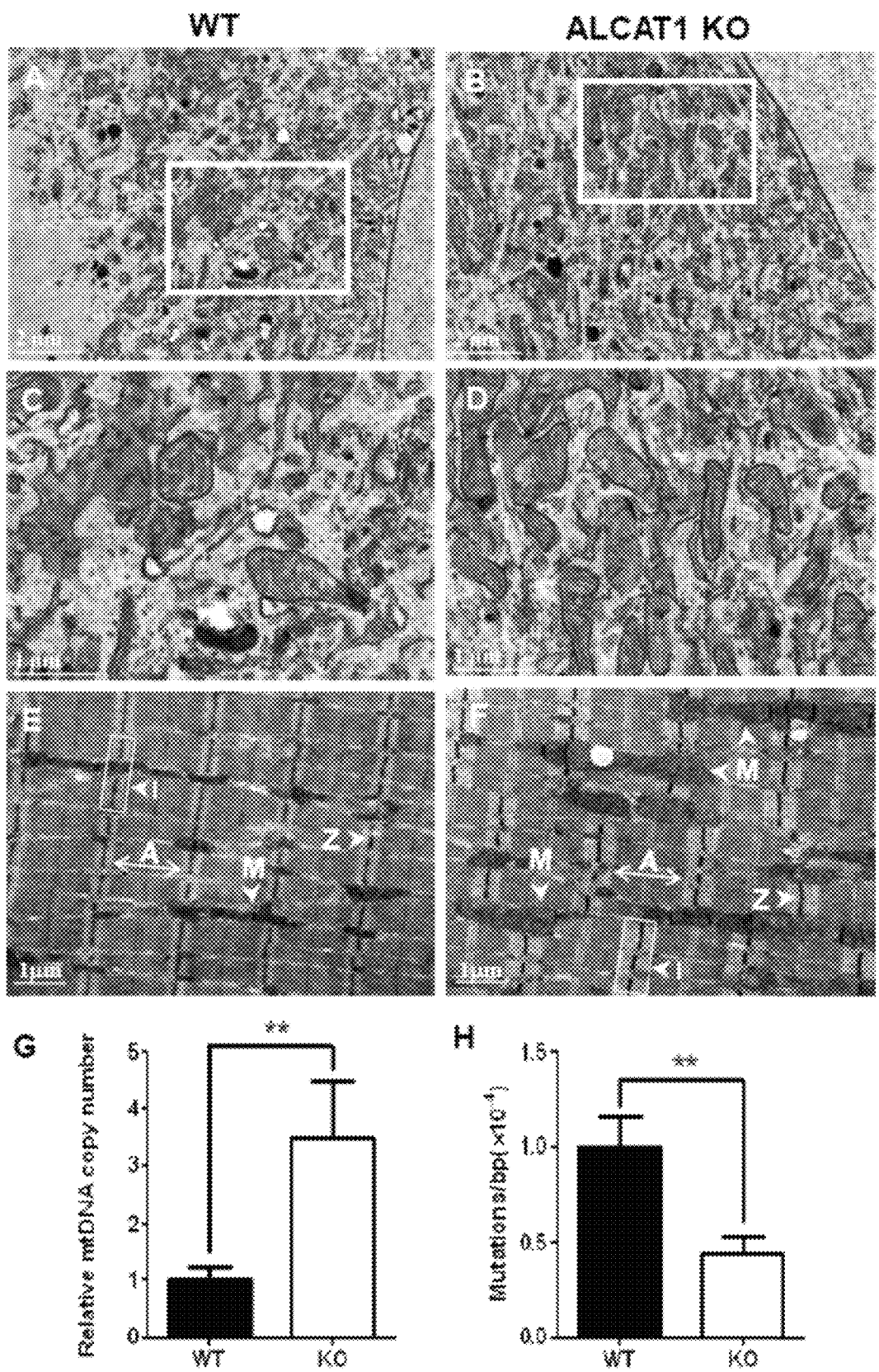
FIGS. 2A-2H show that ALCAT1 deficiency significantly increases mitochondrial mass and improves mtDNA fidelity.

Ablation of ALCAT1 Increases Mitochondrial Mass and mtDNA Fidelity in Mice. Using ALCAT1 knockout mice the effect of ALCAT1 deficiency the effect on mitochondrial morphology, mtDNA mass, and mtDNA mutation rate was investigated in isolated mouse embryonic fibroblasts (MEFs) and skeletal muscles by EM analysis. In support of the findings in the C2C12 cells, ALCAT1 deficiency significantly increased mitochondrial density in cultured MEFs (FIG. 2B, highlighted in FIG. 2D). Ablation of ALCAT1 significantly increased thickness of the muscle fiber in tibialis anterior longitudinal sections, as evidenced by the enlarged dark A bands and light I bands which represent myosin filaments and actin filaments, respectively (FIG. 2F). These results are supported by the data showing that ALCAT1 deficiency significantly increased lean mass in ALCAT1 knockout mice. Furthermore, ablation of ALCAT1 significantly increased mtDNA copy number (FIG. 2G). Strikingly, ALCAT1 deficiency also significantly improved mtDNA fidelity, as evidenced by significantly lower mtDNA mutation rate in the isolated MEFs from ALCAT1 knockout mice (FIG. 2H).

Figures 3A, 3B, 3C, 3D, 3E:
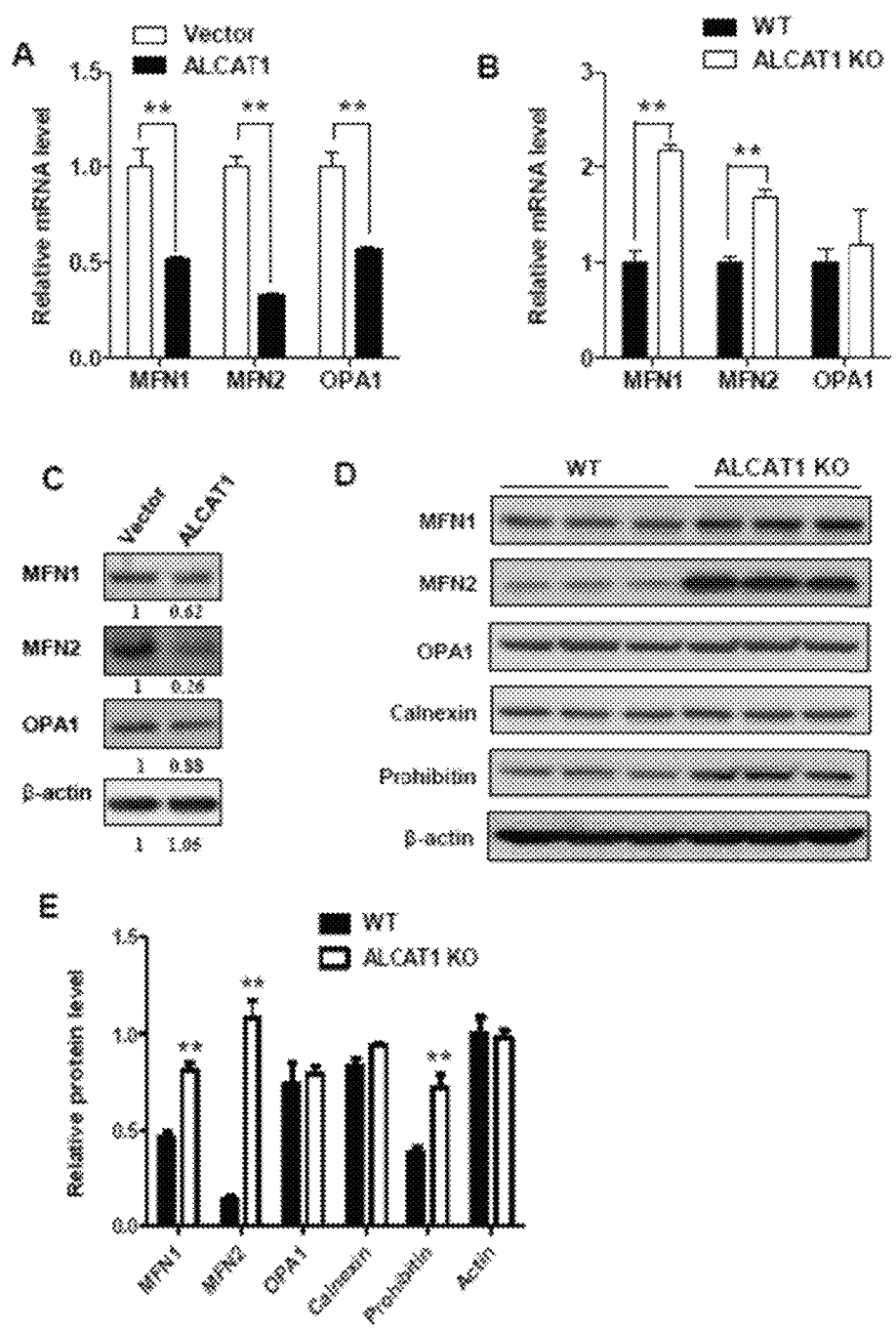
FIGS. 3A-3E show that ALCAT1 regulates biogenesis of MFN1 and MFN2.

A Key Role of ALCAT1 in Regulating MFN2 Expression: MFN2 is required for mitochondrial and endoplasmic reticulum morphology and tethering as a functional bridge. MEFs from MFN2$^{-/-}$ mice display fragmented mitochondria and dilated ER cisternae that resemble the defects caused by in ALCAT1 overexpression. The next question was whether ALCAT1 overexpression and deficiency would reciprocally affect the expression MFN2 and other regulators of the mitochondrial fusion process. As shown in FIG. 3A, ALCAT1 overexpression caused more than 70% depletion of MFN2 mRNA and 50% reduction of both MFN1 and OPA1 mRNAs in the C2C12-A1 stable cell line when compared with vector control. Conversely, ALCAT1 deficiency dramatically increased transcription of MFN2 mRNA concurrently with a significant increase in MFN1 mRNA level in isolated MEFs from ALCAT1 knockout mice (FIG. 3B). However, ALCAT1 deficiency did not have any effect on mRNA expression of OPA1 which is required for the fusion of inner mitochondrial membrane.

Consistent with decreased mRNA levels, expression all the three proteins were also significantly down-regulated by ALCAT1 overexpression. Specifically, MFN2 shows a dramatic reduction by 74.6%, followed by MFN1 (38.0%) and OPA1 (12%), when compared with vector control (FIG. 3C). Conversely, MFN2 protein level was up-regulated by more than 600% in MEFs isolated from the ALCAT1 knockout mice (FIG. 3D, quantified in FIG. 3E). ALCAT1 deficiency also significantly increased the expression of MFN1 and prohibitin, a mitochondrial membrane chaperone protein required for optimal mitochondrial morphology and respiration. In contrast, ALCAT1 deficiency did not affect the expression of OPA1 or calnexin, an ER resident protein (FIG. 3E).

Figures 4A, 4B, 4C, 4D, 4E, 4F, 4G, 4H, 4I, 4J, 4K, 4L:
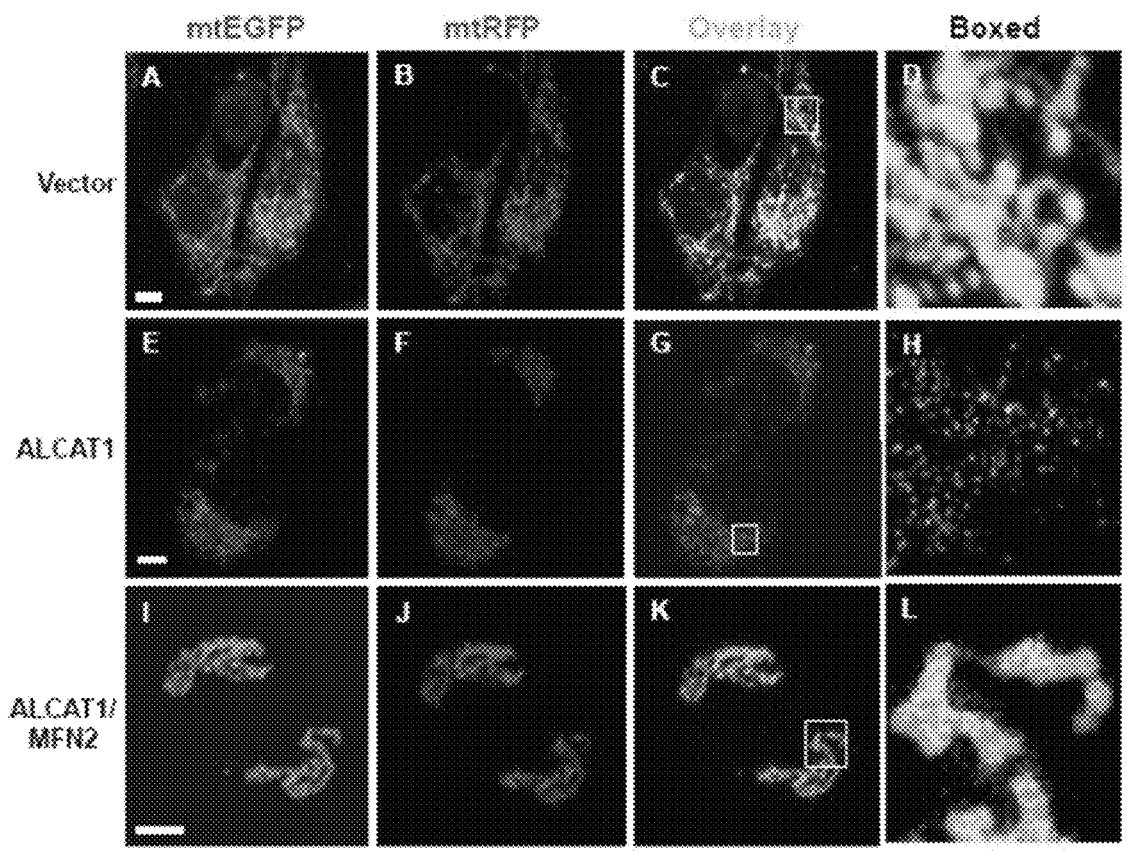
FIGS. 4A-4L show that ALCAT1 impairs mitochondrial fusion, which can be rescued by MFN2 expression in C2C12 cells. C2C12 cells stably expressing ALCAT1 or vector control were transiently transfected with expression plasmid for mitochondrial-targeted GFP or DsRed (mtRFP), coplated, and fused with PEG-1500, followed by confocal microscopic imaging.

ALCAT1 Impairs Mitochondrial Fusion through MFN2 Depletion: The findings that ALCAT1 causes MFN2 depletion and mitochondrial fragmentation prompted an investigation into a role of ALCAT1 in regulating mitochondrial fusion. Mitochondrial matrix-targeted EGFP (mtEGFP) or red fluorescent protein (mtRFP) was individually transfected in C2C12-A1 and C2C12-V2 cells, followed by fusion analysis by measuring overlay of the EGFP and RFP under a confocal microscope. As shown in FIGS. 4A-4C, mitochondria in the vector control C2C12 cells demonstrated normal mitochondrial fusion, as evidenced by the yellow color of the merged image in FIG. 4C (highlighted in FIG. 4D) which evidences a complete fusion. In contrast, ALCAT1 overexpression in C2C12 cells caused a severe fusion defect (FIGS. 4E-4H), as evidenced by well separated green and red colors of the merged image in FIG. 4G (highlighted in FIG. 4H). In direct support of a causative role of MFN2 deficiency in the fusion defect, transient expression of MFN2 in C2C12-A1 cells completely rescued the fusion defect, as supported by the yellow color of the merged image in FIG. 4K (highlighted in FIG. 4L). MFN2 expression also caused super fusion of mitochondria, which is supported by thicker mitochondrial tubular network in C2C12-A cells overexpressing MFN2 (FIGS. 4I-4K).

Figures 5A, 5B, 5C, 5D, 5E, 5F, 5G, 5H, 5I, 5J:
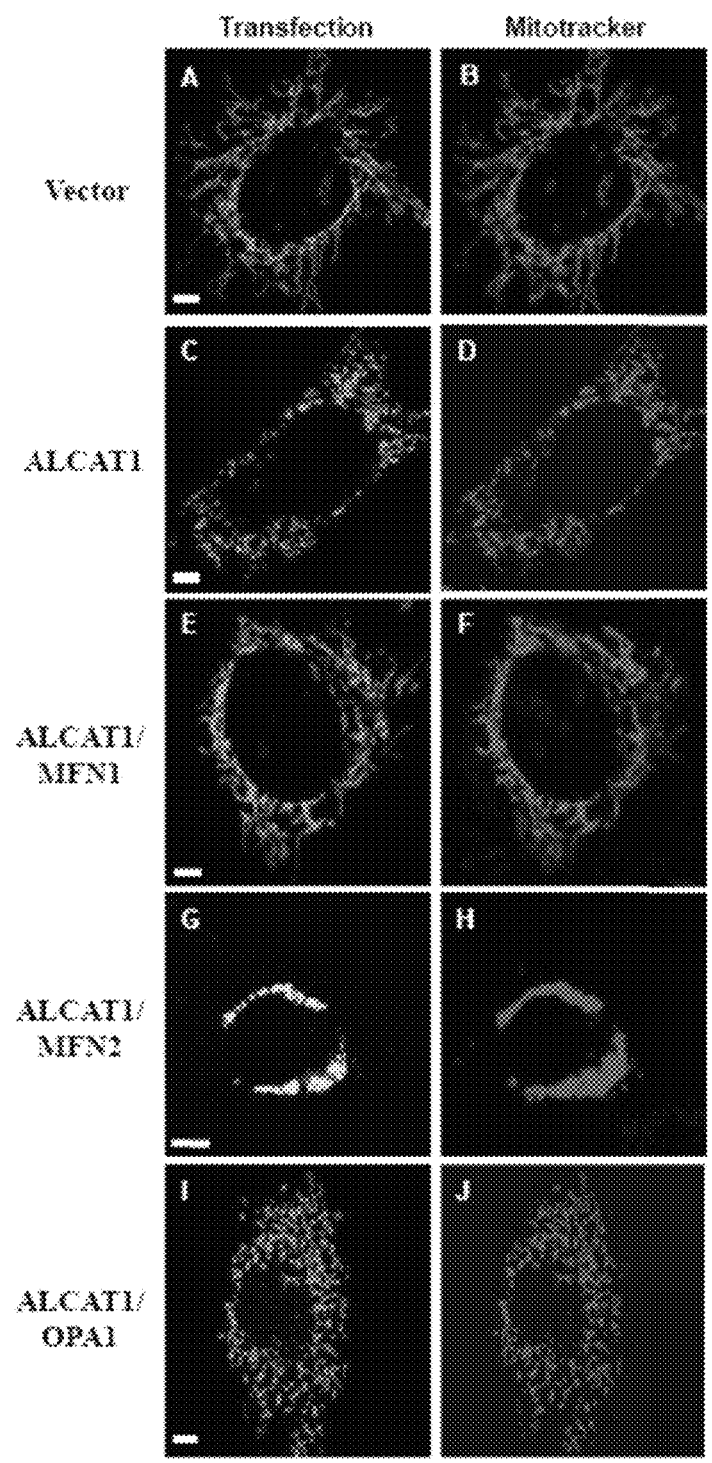
FIGS. 5A-5J show that overexpression of MFN1 and MFN2, but not OPA1, restores mitochondrial network in C2C12-Al cells.

MFN1/2, but not OPA1, Rescues Mitochondrial Fragmentation Caused by ALCAT1: Since MFN2 can rescue the fusion defect caused by ALCAT1, it was questioned whether other members of the dynamin-related family, such as MFN1 and OPA1, could also rescue fusion defect by restoring mitochondrial network in the C2C12-A1 cells. As shown above, ALCAT1 overexpression caused mitochondrial fragmentation in C2C12-A1 cells (FIGS. 5C & 5D) when compared with vector control (FIGS. 5A & 5B). In contrast, transient expression of MFN1 in C2C12-A1 cells almost completely rescued the fusion defect, as shown by the recovery of the tubular mitochondria (FIGS. 5E & 5F). Again, transient expression of MFN2 completely rescued the fusion defect, leading to super fusion of mitochondria (FIGS. 5G & 5H).

In contrast, transient expression of OPA1 failed to rescue any of the fusion defect (FIGS. 5I & 5J), which is consistent with a lack of any effect of ALCAT1 deficiency on OPA1 expression in MEFs (FIGS. 3B & 3E). The results evidence that the ALCAT1-mediated fusion defect is limited to the out mitochondrial membrane where ALCAT1 is localized.

Figures 6A, 6B, 6C, 6D:
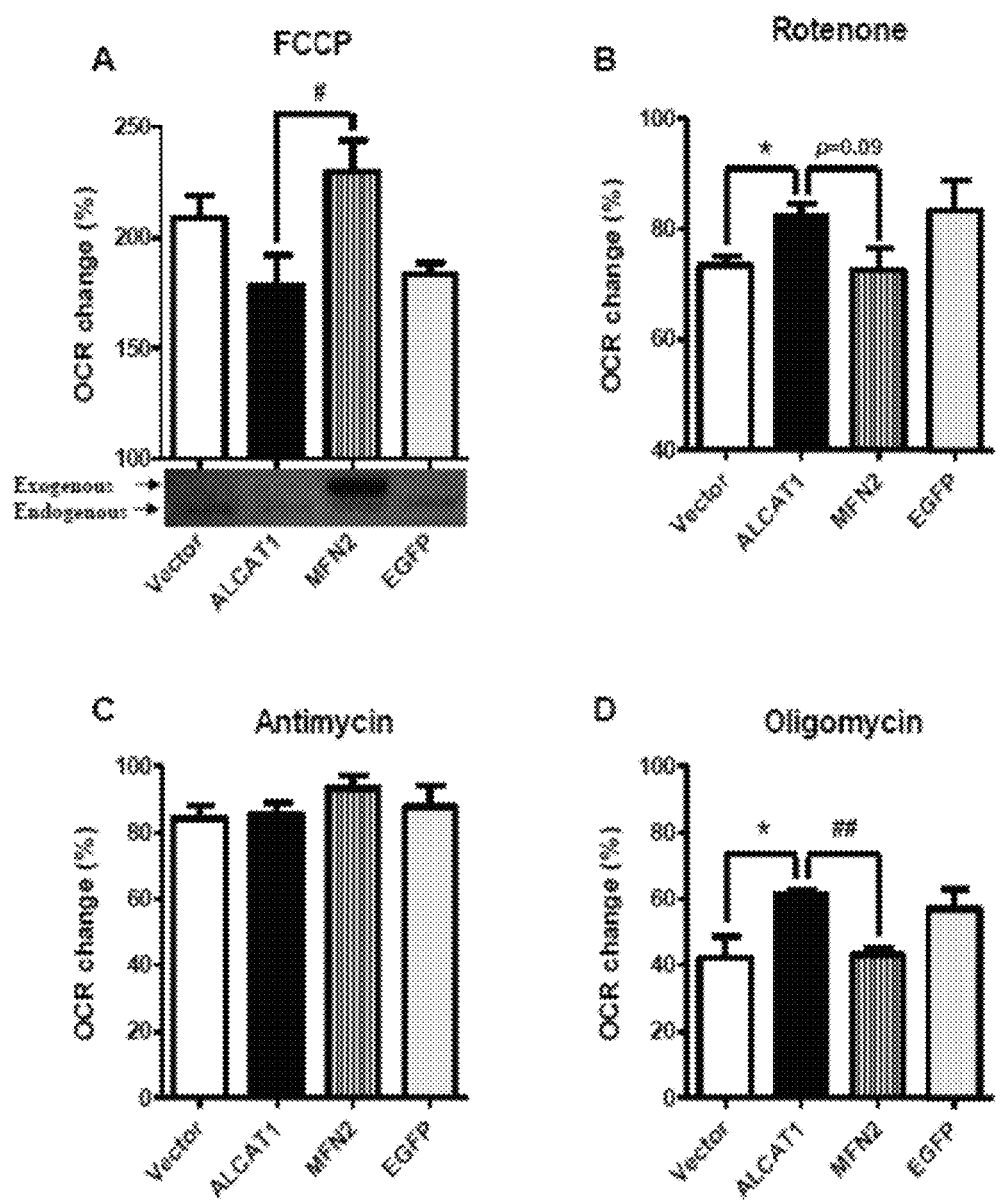
FIGS. 6A-6D shows that MFN2 restores the mitochondrial respiratory capacity in C2C12 cells stably expressing ALCAT1. C2C12 cells stably expressing ALCAT1 were transiently transfected with expression vectors for MFN2 or EGFP, and were compared with vector control for changes in oxygen consumption rate (OCR) in response to treatment with various mitochondrial inhibitors, including.

MFN2 Rescues Mitochondrial Respiratory Defects Caused by ALCAT1 Overexpression: It was next investigated whether MFN2 expression could also restore mitochondrial respiratory function in C2C12-A1 cells. ALCAT1 causes mitochondrial dysfunction by increasing mitochondrial proton leakage. A role of MFN2 expression on proton leakage was interrogated in C2C12-A1 cells by analyzing changes in $O_2$ consumption rate (OCR) in response to treatments with different mitochondrial inhibitors. Using the Seahorse Extracellular Flux (XF-24) analyzer, it was shown that ALCAT1 overexpression significantly decreased mitochondrial maximum capacity, as indicated by decreased OCR in response to treatment with FCCP, a mitochondrial uncoupler (FIG. 6A). Transient expression of MFN2, but not EGFP vector control, completely restored mitochondrial respiratory capacity, as evidenced by the recovery of OCR relative to vector control (FIG. 6A). Consistent with complex I as the major site for ROS production, ALCAT1 overexpression significantly increased OCR in response to treatment with rotenone, an inhibitor of complex I (NADH CoQ1 reductase), providing evidence for mitochondrial proton leakage. In support of a causative role of MFN2 deficiency in oxidative stress, transient expression of MFN2 in C2C12-A1 cells completely normalized OCR (FIG. 6B). Furthermore, ALCAT1 overexpression also significantly increased OCR in response to treatment with oligomycin, a mitochondrial ATPase inhibitor, further indicating a proton leakage. The defect is also completely normalized by transient expression of MFN2 (FIG. 6D). In contrast, neither ALCAT1 nor MFN expression had any effect on OCR from complex III in response to treatment with antimycin, a complex III inhibitor.

Figures 7A, 7B, 7C, 7D, 7E, 7F, 7G, 7H:
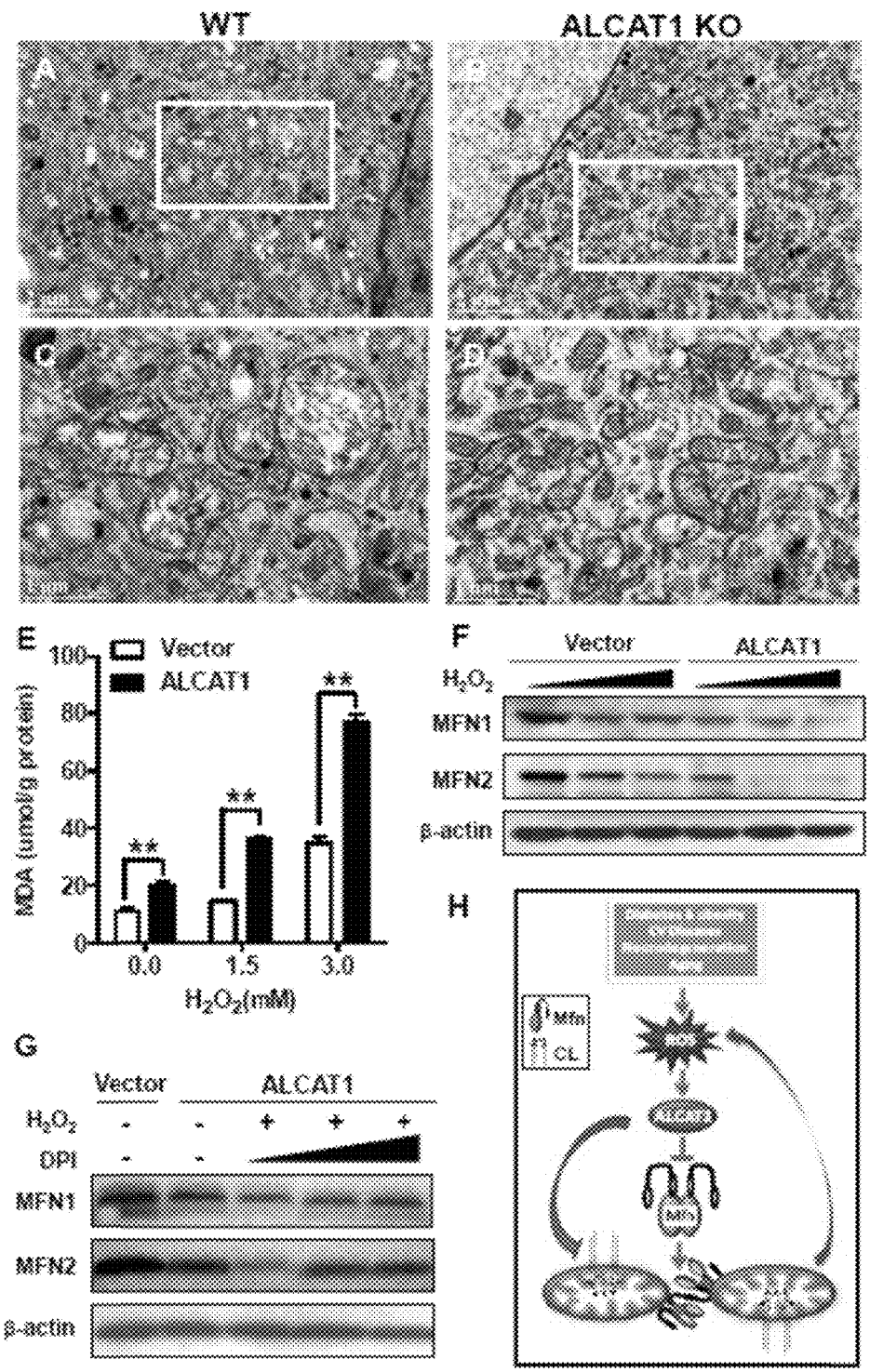
FIGS. 7A-7H show that oxidative stress by ALCAT1 links ROS production to MFN2 deficiency.
Figure 10:
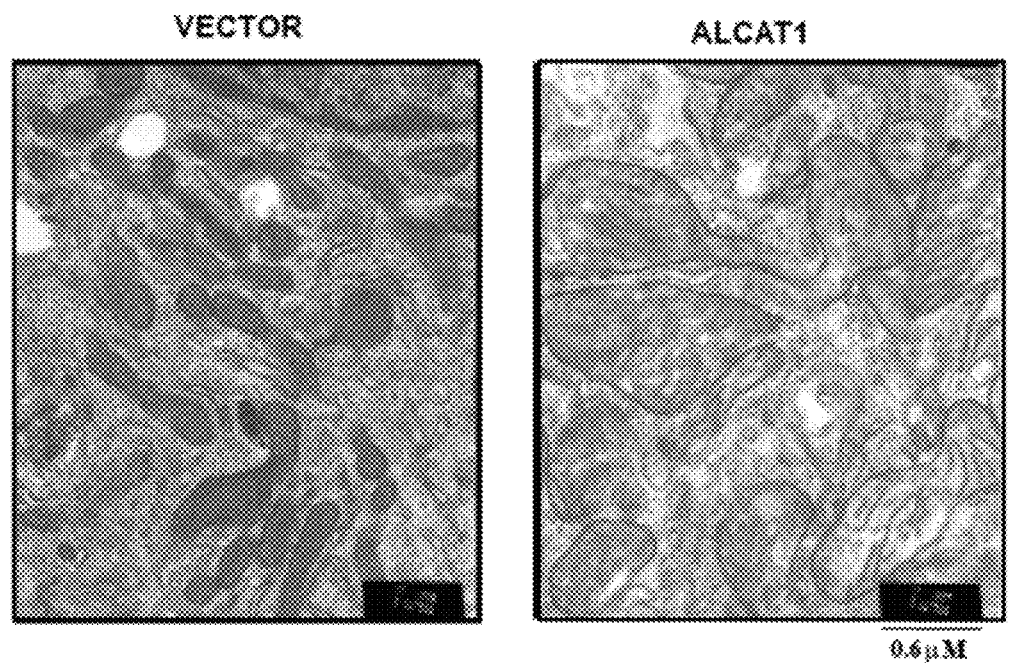
FIG. 10 shows that overexpression of ALCAT1 in C2C12 cells caused mitochondrial swelling. C2C12 cells stably transfected with ALCAT1 expression vector or an empty vector were selected for individual clones. The C2C12 cell lines stably expressing ALCAT1 or vector control were analyzed for mitochondrial morphology by electron microscopy. ALCAT1 overexpression caused severe mitochondrial swelling, as evidenced by enlarged mitochondria and damaged cristae.

ALCAT1 Links Oxidative Stress to Mitochondrial Fragmentation and MFN2 Deficiency: Impaired mitochondrial fusion from oxidative stress causes mitochondrial swelling by opening the mitochondrial permeability transition pore. Damaged mitochondria often generate more ROS which further exacerbate mitochondrial dysfunction, leading to a vicious cycle. Since CL remodeling by ALCAT1 causes oxidative stress, it was questioned whether ALCAT1 played a role in the vicious cycle, which was tested in isolated MEFs from ALCAT1 knockout and control mice. As shown in FIG. 7A (highlighted in FIG. 7C), MEFs from control mice exhibit severe mitochondrial swelling in response to treatment with $H_2O_2$, as evidenced by enlarged mitochondria and damaged cristae. ALCAT1 overexpression caused severe mitochondrial swelling in one of the C2C12 stable cell lines that exhibits the highest expression of ALCAT1 relative to the vector controls (FIG. 10). Due to this extreme feature, this C2C12 cell line was not used for the current studies. In contrast, ALCAT1 deficiency completely prevented mitochondrial swelling (FIG. 7B, highlighted in FIG. 7D) and mitochondrial fragmentation in isolated MEFs in response to treatment of $H_2O_2$ (FIGS. 9A-9D).

In support of CL remodeling by ALCAT1 as a major cause of oxidative stress, ALCAT1 overexpression significantly increased lipid peroxidation in C2C12-A1 cells, which was dose-dependently exacerbated by the treatment with $H_2O_2$, as shown by elevated level of malondialdehyde (MDA), an end product of lipid peroxidation (FIG. 7E). Mitochondria undergo rapid fragmentation with a concomitant increase in ROS production. The next question was whether ALCAT1 would cause MFN2 deficiency through ROS production. The C2C12-A1 cells and vector control were treated with increasing doses of $H_2O_2$ as used in FIG. 7E, followed by analysis of MFN2 expression by western blot analysis. As shown in FIG. 7F, $H_2O_2$ dose-dependently depleted MFN1 and MFN2 expression in vector control cells. The treatment also further exacerbated the effect of ALCAT1 on MFN1 and MFN2 depletion, leading to a complete loss of MFN2 expression in C2C12-A1. Finally, in direct support of oxidative stress by ALCAT1 as the primary cause of MFN depletion, pre-incubation of the C2C12-A1 cells with diphenyleneiodonium (DPI), an antioxidant, dose-dependently prevented the loss of MFN expression in response to the same treatment with $H_2O_2$ as used in FIG. 7F (FIG. 7G).

Discussion:

Dynamic networks are formed when mitochondria undergo a fusion event that causes the compartments of participating mitochondria to become continuous. The fusion event allows the constituents of each network to share solutes, metabolites, and proteins. Consequently, disruption of such networks causes oxidative stress and mitochondrial fragmentation, which has been implicated in the etiology of aging and age-related diseases. However, little is known about the underlying mechanisms. The current studies investigated a role of ALCAT1 in regulating oxidative stress and mitochondrial fragmentation commonly associated with age-related metabolic diseases. A critical role of ALCAT1 in regulating mitochondrial biogenesis and mtDNA fidelity was demonstrated for the first time. Accordingly, ALCAT1 overexpression severely impairs mitochondrial fusion, leading to mitochondrial fragmentation and mtDNA depletion. Conversely, targeted inactivation of ALCAT1 in mice significantly increases mitochondrial mass and protects mitochondria from ROS-induced mitochondrial swelling and fragmentation. Strikingly, a role of ALCAT1 in regulating mtDNA fidelity it was demonstrated, which is corroborated by previous studies that mitochondrial fusion is required to safeguard mtDNA integrity (Chen H, et al. (2010) *Cell* 141(2):280-289).

In support of a role of ALCAT1 in mitochondrial fusion, the current studies identified MFN2 as a downstream target of ALCAT1-mediated mitochondrial dysfunction. MFN2 is required for mitochondrial fusion, tethering with ER, energy metabolism, and mtDNA fidelity in mammals (Chen H, et al. (2010) *Cell* 141(2):280-289, 22; de Brito O M & Scorrano L (2008). *Nature* 456:605-610). ALCAT1 overexpression severely depleted MFN2 expression in C2C12 cells, whereas ALCAT1 deficiency dramatically increased MFN2 expression in isolated MEFs from ALCAT1 knockout mice. In contrast, ALCAT1 deficiency did not have any effect on expression of OPA1 which is required for fusion of the inner mitochondrial membrane. The results provide evidence that ALCAT1 only affects the fusion of the outer mitochondrial membrane where ALCAT1 is localized (Li J, et al. (2010) *Cell Metab* 12(2):154-165), which is further corroborated by a previous report that 25% CL is localized in the outer membrane where active CL remodeling takes place (Gebert N, et al. (2009) *Curr Biol* 19(24):2133-2139). Consistent with MFN2 as the downstream target of ALCAT1-mediated fusion defect, targeted inactivation of MFN2 in mice causes multiple mitochondrial defects that are reminiscent of ALCAT1 overexpression, including high mtDNA mutation rate, mtDNA depletion, fragmented mitochondria, and a profound loss of tethering between mitochondria and ER. MFN2 deficiency also caused skeletal muscle atrophy, which is consistent with the findings that ALCAT1 deficiency significantly increased skeletal mass in ALCAT1 knockout mice (Li J, et al. (2010) *Cell Metab* 12(2):154-165, Chen H, et al. (2010) *Cell* 141(2):280-289). In direct support of MFN2 as downstream target of ALCAT1, the fusion defect caused by ALCAT1 can be rescued by expression of either MFN1 or MFN2, but not by OPA1. Furthermore, MFN2 expression also restored the mitochondrial respiratory capacity and prevented proton leakage caused by ALCAT1 overexpression in C2C12 cells. These results are consistent with the observation that MFN2 deficiency significantly increases proton leakage (Bach D, et al. (2003) *J Biol Chem* 278(19):17190-17197), whereas overexpression of MFN2 blocks hyperglycemia-induced ROS production (Yu T, Robotham J L, & Yoon Y (2006) *Proc Natl Acad Sci U S A* 103(8):2653-2658).

Mitochondrial fission/fusion machinery controls acute and chronic production of ROS in hyperglycemia-associated disorders (Yu T, Robotham J L, & Yoon Y (2006) *Proc Natl Acad Sci U S A* 103(8):2653-2658). Mitochondria undergo rapid fragmentation concomitantly with an increased ROS production in response to oxidative stress, which can be mitigated through inhibition of fission or stimulation of the fusion process. The current studies identified ALCAT1 as a missing link between mitochondrial fusion defect and ROS production in metabolic diseases. First, CL remodeling by ALCAT1 significantly increased DHA content in CL, leading to proton leakage and oxidative stress. DHA content in mitochondrial membrane inversely correlates with lifespan and positively correlated with ROS production and lipid peroxidation index in mammals. Hence, increased DHA content in CL increase lipid peroxidation index, has been implicated in mitochondrial dysfunction in aging and age-related diseases (Han X, et al. (2007) *Biochemistry* 46(21): 6417-6428; Sparagna G C & Lesnefsky E J (2009) *J Cardiovasc Pharmacol* 53(4):290-301; Lee H-J, (2006) *Lipids Health & Dis.* 5:2; Paradies G, et al., (2010) *Free Radic Biol Med* 48(10):1286-1295; Shi Y (2010) *J Biomed Res* 24(1):6-15). Second, ALCAT1 overexpression caused severe lipid peroxidation in C2C12 cells, which was further exacerbated by oxidative stress. Finally, in direct support of oxidative stress by ALCAT1 as the primary cause of the fusion defect, ALCAT1 overexpression significantly depleted MFN2 expression, which can be mitigated by pretreatment of C2C12 cells with an antioxidant. Together, these findings support a key role of ALCAT1 in linking ROS production to mitochondrial fragmentation through depletion of MFN2 in age-related diseases, as depicted in FIG. 7H.

A regulatory role of ALCAT1 in mitochondrial fusion is further underscored by recent studies on MitoPLD, a mitochondrial PLD involved in CL metabolism (Choi S Y, et al. (2006) *Nat Cell Biol* 8(11):1255-1262). Mito-PLD is localized on mitochondrial outer membrane where it catalyzes the hydrolysis of CL to produce phosphatidic acid, a fusiongenic lipid required for mitochondrial fusion. Strikingly, MitoPLD deficiency causes mitochondrial dysfunction that is reminiscent of that by ALCAT I overexpression, including impaired fusion and mitochondrial fragmentation. However, there are significant differences in underlying mechanisms. For example, MitoPLD functions downstream of MFN2, and MitoPLD expression can rescue fusion defects caused by MFN deficiency. Additionally, in contrast to ALCAT1, levels of MFN1 and MFN2 protein expression are not altered by MitoPLD overexpression or deficiency. Furthermore, overexpression of MitoPLD causes super fusion concurrently with mild CL deficiency. Finally, MitoPLD has recently been demonstrated a role in regulating piRNA stability and male sterility in mice (Huang H, et al. (2011) *Dev Cell* 20(3):376-387). The findings herein, evidence that CL remodeling by ALCAT1 regulates mitochondrial fusion independent of phosphatidic acid production.

The onset of aging and age-related diseases is associated with oxidative stress and increased mtDNA mutation rate, which have been proposed as the primary causes of aging and age-related diseases. Additionally, MFN2 deficiency has been implicated in age-related metabolic diseases. Importantly, the current studies have identified an important role of ALCAT1 in controlling mtDNA fidelity and MFN2 expression. The findings herein, will have important implications in future studies to decipher molecular mechanisms underlying the onset of aging and age-related diseases. In support of a role of ALCAT1 in the onset of age-related diseases, ALCAT1 expression is up-regulated by oxidative stress and by the onset of age-related metabolic diseases. Targeted inactivation of ALCAT1 prevents the onset of obesity and its related mitochondrial dysfunction. Therefore, it can be envisaged that development of chemical inhibitors for ALCAT1 will provide a potential treatment for aging and age-related diseases in the future.

Example 2

Cardiolipin Remodeling by ALCAT1 Regulates Cardiomyopathy through Effects on Oxidative Stress and Mitophagy Using mice with hyperthyroidism as a rodent model of oxidative stress and mitochondrial dysfunction, the present study investigates a role of ALCAT1 in cardiomyopathy associated with hyperthyroidism. The results demonstrate for the first time a key role of ALCAT1 in regulating the onset of thyroid hormone-induced cardiac hypertrophy through oxidative stress and mitophagy.

Materials and Methods

Reagents: Antibodies used in the present studies include polyclonal antibodies to phospho-AKT (Thr308), AKT, Phospho-S6K1 (Thr389), S6K1, phospho-S6 (Ser240/244), S6, phospho-4E-BP1 (Thr37/46), 4E-BP1, all of which were purchased from Cell Signaling Technology (Danvers, Mass.). Anti-LC3 antibody was purchased from Novus Biologicals, and anti-p62 antibody was from American Research Products Inc (Belmont, Mass.). The PINK1 polyclonal antibody (A01) was purchased from Abnova. Donkey anti-Rabbit IgG horseradish peroxidase-conjugated antibodies were purchased from GE Healthcare (Piscataway, N.J.). L-thyroxine (T4) and 3,3',5-triiodo-L-thyronine sodium salt (T3) were from Sigma.

Generation of H9c2 Stable Cell Lines: H9C2 cells were stably transfected with FLAG-tagged ALCAT1 expression vector or empty vector as control. The stable transfectants were screened by G418 (1 mg/ml) and cultured in Dulbecco's modified Eagle's medium (Gibco), supplemented with 10% heat-inactivated fetal calf serum 1% penicillin and streptomycin, maintained in 95% air and 5% $CO_2$ at 37° C.

Animal Care: Mice with targeted deletion of the ALCAT1 gene was generated as previously described (Li J, et al. (2010) *Cell Metab* 12(2):154-165). For induction of hyperthyroid cardiomyopathy, male ALCAT1 knockout mice age-matched WT mice (8-9 weeks old) were divided into two groups. One group was treated with thyroid hormone (levothyroxine, Sigma CAS 51-48-9, 1 mg/kg body weight daily by i.p. injection) in the vehicle of 0.01N NaOH and 0.9% NaCl for 2 days or 4 weeks. Control group of mice were injected with the same vehicle for the same duration. All animals were maintained in an environmentally controlled facility with diurnal light cycle and free access to water and either a standard rodent chow (Harland Teklad 2018, Madison, Wis.). All experiments involving animals were performed in compliance with approved institutional animal care and use protocols according to NIH guidelines (NIH publication No. 86-23, 1985).

Echocardiography: After 4 weeks of thyroid hormone treatment, mice were lightly anesthetized with Intraperitoneal injection of sodium pentobarbital (75 µg/g body weight). Transthoracic echocardiography studies were performed using an acuson sequoia model 512 echocardiography system (Siemens, Malvern, Pa.) with a 14-MHz linear transducer. The following parameters were measured: interventricular septal wall thickness at the end of diastole (IVSD), end-diastolic dimension of left ventricular (LVEDD), posterior wall thickness at the end of diastole (LVPWD).

Quantitative PCR Analysis: Quantitative PCR analyses were carried out as previously described (Li J, et al. (2010) *Cell Metab* 12(2):154-165). Analysis of mitochondrial copy number in vector and ALCAT1 overexpression H9c2 cells were carried out using mitochondria-encoded NADH dehydrogenase 1 (ND1) as the mtDNA marker and cyclophilin-A as genomic marker. The H9c2 cells were pretreated with $H_2O_2$ at 0.1, 0.25, 0.5 mM for 2h, followed by RT-PCR analysis using primer pair for ND1 (forward: 5'-TGAC-CCATAGCCATAATATGATTT-3' (SEQ ID NO: 1) and reverse: 5'-TTCTACGTTAAACCCTGATACTAA-3' (SEQ ID NO: 2)) and cyclophilin-A (forward: 5'-ACACGC-CATAATGGCACTCC-3'(SEQ ID NO: 3)) and reverse: 5'-CAGTCTTGGCAGTGCAGAT-3' (SEQ ID NO: 4)). Quantitative PCR analysis of biomarkers were carried out using primer pairs for β-MHC (forward: 5'-AGGGCGAC-CTCAACGAGAT-3' (SEQ ID NO: 5), reverse: 5'-CAGCA-GACTCTGGAGGCTCTT-3' (SEQ ID NO: 6)), BNP (forward: 5'-GCTGCTTTGGGCACAAGATAG-3' (SEQ ID NO: 7), reverse: 5'-GGAGCTCTTCCTACAACAACTT-3' (SEQ ID NO: 8)), ANF (forward: 5'-GTGTACAGTGCG-GTGTCCAA-3' (SEQ ID NO: 9), reverse: 5'-ACCTCATCT-TCTACCGGATC-3' (SEQ ID NO: 10)), ACTA1 (forward: 5'-GTTCGCGCTCTCTCTCCTCA-3' (SEQ ID NO: 11), reverse: 5'-GCAACCACAGCACGATTGTC-3' (SEQ ID NO: 12)), collagen I (forward: 5'-GAGCGGAGAGTACTG-GATCG-3' (SEQ ID NO: 13), reverse: 5'-GTTCGGGCT-GATGTACCAGT-3' (SEQ ID NO: 14)), collagen III (forward: 5'-ACCAAAAGGTGATGCTGGAC-3' (SEQ ID NO: 15), reverse: 5'-GACCTCGTGCTCCAGTTAGC-3' (SEQ ID NO: 16)), and GAPDH (forward: 5'-AATGGT-GAAGGTCGGTGTG-3' (SEQ ID NO: 17), reverse: 5'-GTGGAGTCATACTGGAACATGTAG-3' (SEQ ID NO: 18)).

Lipid Peroxidation Assay: Lipid peroxidation products in the cardiac ventricular tissue and H9c2 cells were quantified by measuring the level of thiobarbituric acid reactive-substances (TBARS) using a TBARS kit (Cayman Chemical Company, Cat No. 10009055) according to manufacturer's instruction.

Reactive oxygen species (ROS) measurements: The intracellular reactive oxygen species (ROS) generation from mitochondria was detected indirectly by quantitatively measuring Hydrogen Peroxide ($H_2O_2$).

EM Analysis of Mitochondria: Mitochondria ultrastructure in mice cardiomyocytes was evaluated using Electron photomicrographs. Heart samples were taken at the same site of left ventricle from three mice in each group to prepare slides. Fragments of heart left ventricle were fixed in 5% glutaraldehyde and 4% paraformaldehyde in 0.1M sodium cacodylate buffer (pH 7.4) with 0.05% $CaCl_2$ for 24 h. After washing in 0.1M sodium cacodylate buffer, tissues were post-fixed in 1% $OsO_4$ and 0.1M cacodylate buffer overnight, dehydrated and embedded in Embed 812. The Sections were stained with 2% uranyl acetate followed by 0.4% lead citrate, and viewed with a Philips 400 electron microscope.

Statistical Analysis: Data was expressed as a mean±SEM. Statistical comparisons were done using two-tailed non-paired t-tests to evaluate the difference between the two H9c2 cell lines and between ALCAT1 knockout and wild-type mice. For comparisons among more groups, one-way analysis of variance was used, and statistical significance was considered at p<0.05.

Results

Figures 11A, 11B, 11C, 11D, 11E, 11F:
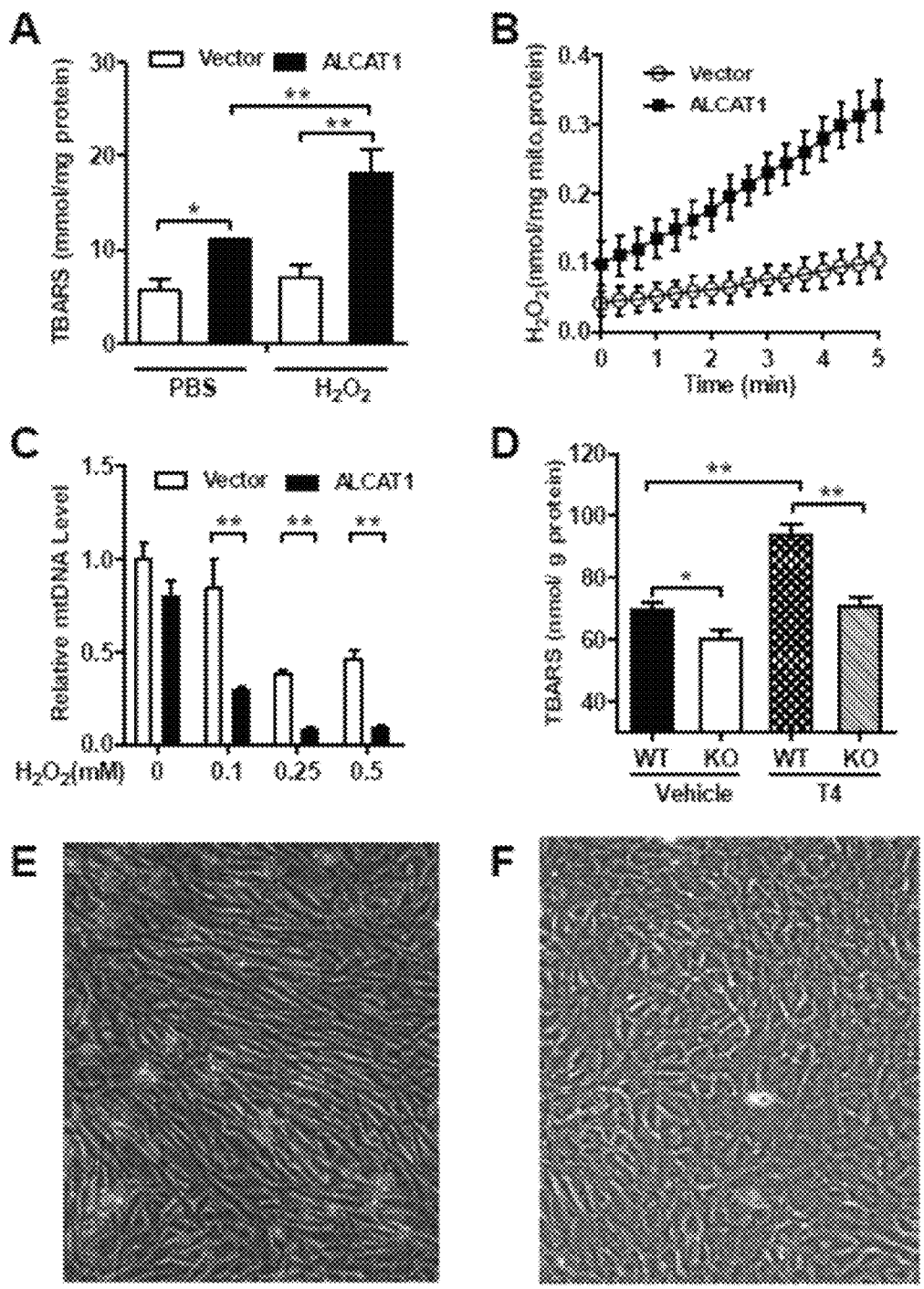
FIGS. 11A-11F show that ALCAT1 regulates oxidative stress and lipid peroxidation in cardiomyopathy. The H9c2 cells stably overexpressing ALCAT1 or vector control were analyzed for (FIG. 11A) intracellular level of thiobarbituric acid reactive substances (TBARS), a byproduct of lipid peroxidation, in response to treatment with saline (PBS) or saline plus 2 mM $H_2O_2$ for two hours.

ALCAT1 Regulates Cardiac Lipid Peroxidation and mtDNA Biogenesis: ALCAT1 expression in the heart is up-regulated by oxidative stress and by onset of hyperthyroid cardiomyopathy. The studies here, show that abnormal expression of ALCAT1 plays a causative role in the onset of cardiomyopathy. First the role of ALCAT1 overexpression in H9c2 cardiac cell line on cellular morphology and mitochondrial function was investigated. To do so, H9c2 cardiac cell lines stably transfected with flag-tagged ALCAT1 cDNA (ALCAT1) or vector control were generated. The mRNA expression level of ALCAT1 in the stable H9c2 cell line is only three fold higher than vector control, which mimics the up-regulated level of endogenous ALCAT1 induced by oxidative stress in isolated cardiomyocytes (Li J, et al. (2010) *Cell Metab* 12(2):154-165). Using these two stable H9c2 cell lines as a cell-based model, the effect of ALCAT1 on lipid peroxidation and mtDNA copy number was first analyzed. As shown in FIG. 11A, compared with vector control, ALCAT1 overexpression significantly increased the intracellular level of thiobarbituric acid reactive substances (TBARS), a byproduct of lipid peroxidation. The production of TBARS was further exacerbated in response to treatment with $H_2O_2$, evidencing a causative role of ALCAT1 in oxidative stress in cardiomyopathy.

Figure 18A:
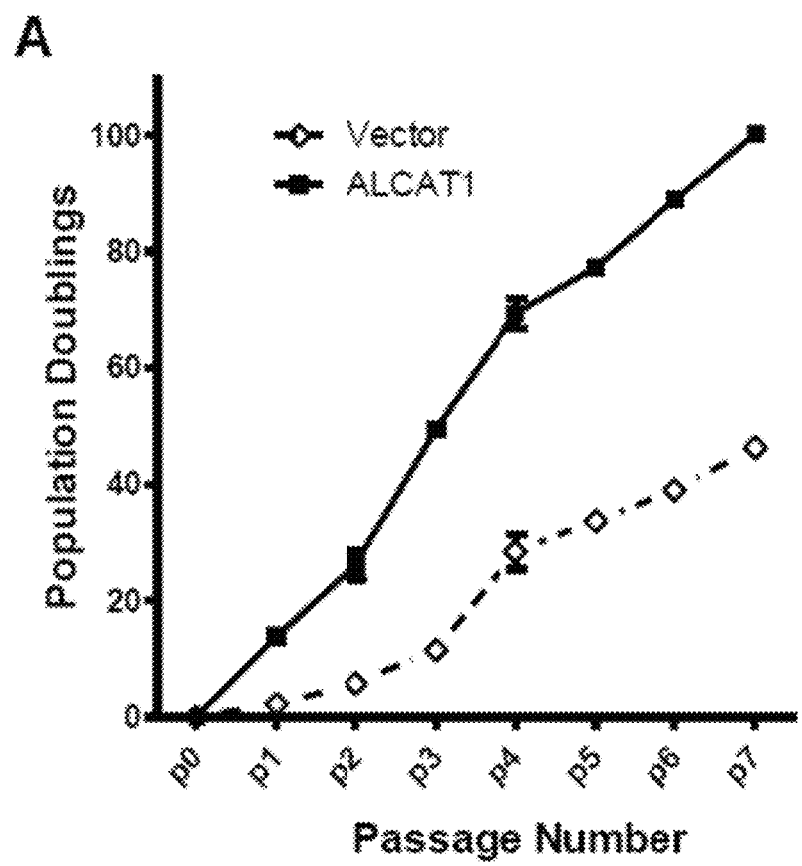
FIGS. 18A-18B show that stable overexpression of ALCAT1 in H9c2 cells leads to hypertrophic growth and impairment in differentiation to cardiomyocytes.
Figure 18B:
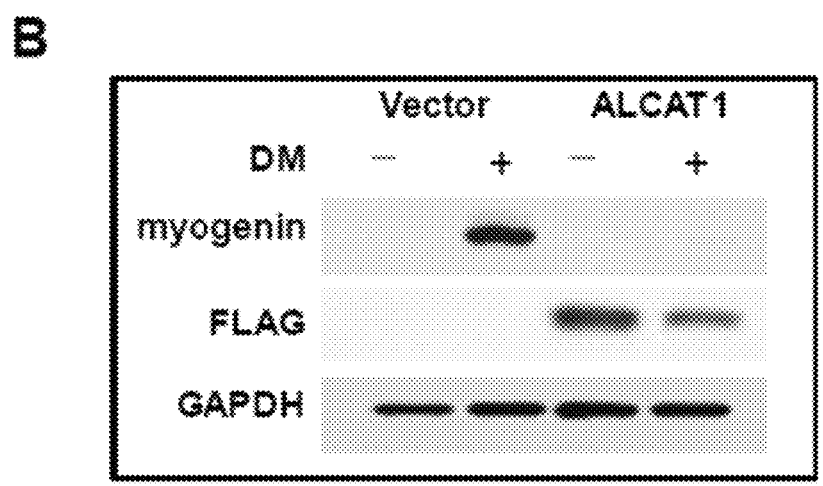
Figures 19A, 19B, 19C, 19D, 19E, 19F:
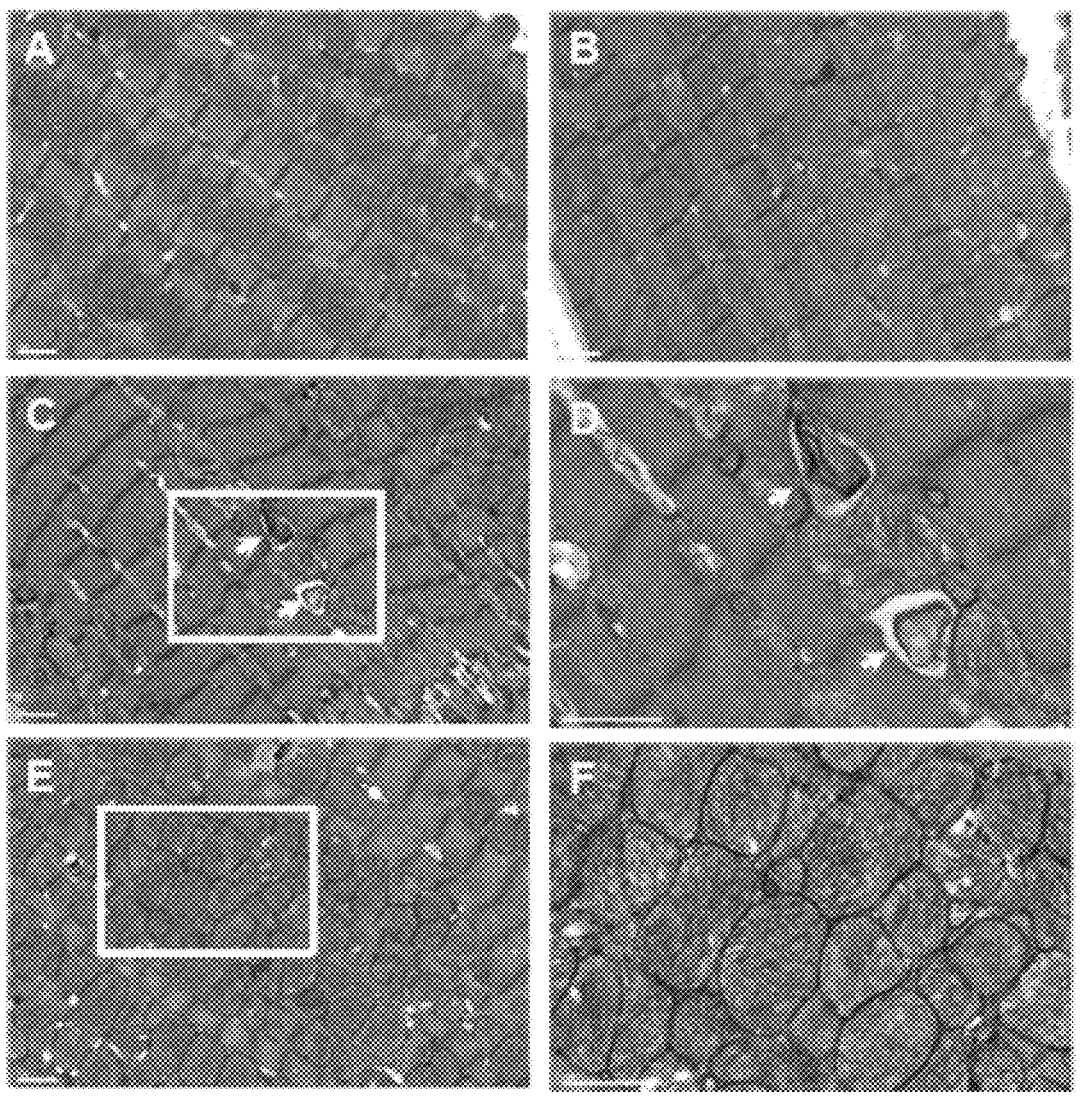
FIGS. 19A-19F show that ablation of ALCAT1 prevents mitochondrial damage and mitophagy associated with cardiomyopathy. The ALCAT1 knockout mice and WT controls were treated with vehicle or T4 treatment for 28 days, followed by electron micrographic analysis of longitudinal sections of cardiac ventricular muscle.

In order to uncover the direct effect of ALCAT1 on mitochondria ROS release, mitochondrial ROS production rate was profiled in the ALCAT1-expressing H9c2 cell line and the vector control. $H_2O_2$ production rate was analyzed in isolated mitochondria isolated from the H9c2 cells at fixed time points after the initiation of the assay. The results show ALCAT1 overexpression significantly increased the relative ROS release rates by 3.77 fold (P<0.01) (FIG. 11B). Oxidative stress causes mtDNA instability, which has been implicated in mitochondrial dysfunction in age-related metabolic diseases. In further support of ALCAT1 as the primary source of oxidative stress, ALCAT1 overexpression led to mtDNA depletion in H9c2 cells in response to treatment with increasing doses of $H_2O_2$ (FIG. 11C). Additionally, ALCAT1 overexpression also caused hypertrophic growth of H9c2 cells (FIG. 18A). Furthermore, ALCAT1 overexpression caused defective differentiation of H9c2 cells to cardiomyocytes (FIGS. 11E & 11F), as evidenced by a lack of expression of myogenin, a key indicator of differentiated H9c2 cells (FIG. 18B).

Hyperthyroidism causes oxidative stress and lipid peroxidation. Using ALCAT1 knockout mice, the effect of ALCAT1 deficiency on lipid peroxidation in the heart under conditions associated with the onset of cardiomyopathy, was analyzed. Consistent with reported effect of hyperthyroidism on oxidative stress, hyperthyroidism significantly increased the level of lipid peroxidation in the heart (FIG. 11D). In contrast, targeted inactivation of ALCAT1 completely prevented cardiac lipid peroxidation in response to the onset of hyperthyroid cardiomyopathy, further confirming a causative role of ALCAT1 in oxidative stress associated with cardiomyopathy.

Figures 12A, 12B, 12C, 12D, 12E:
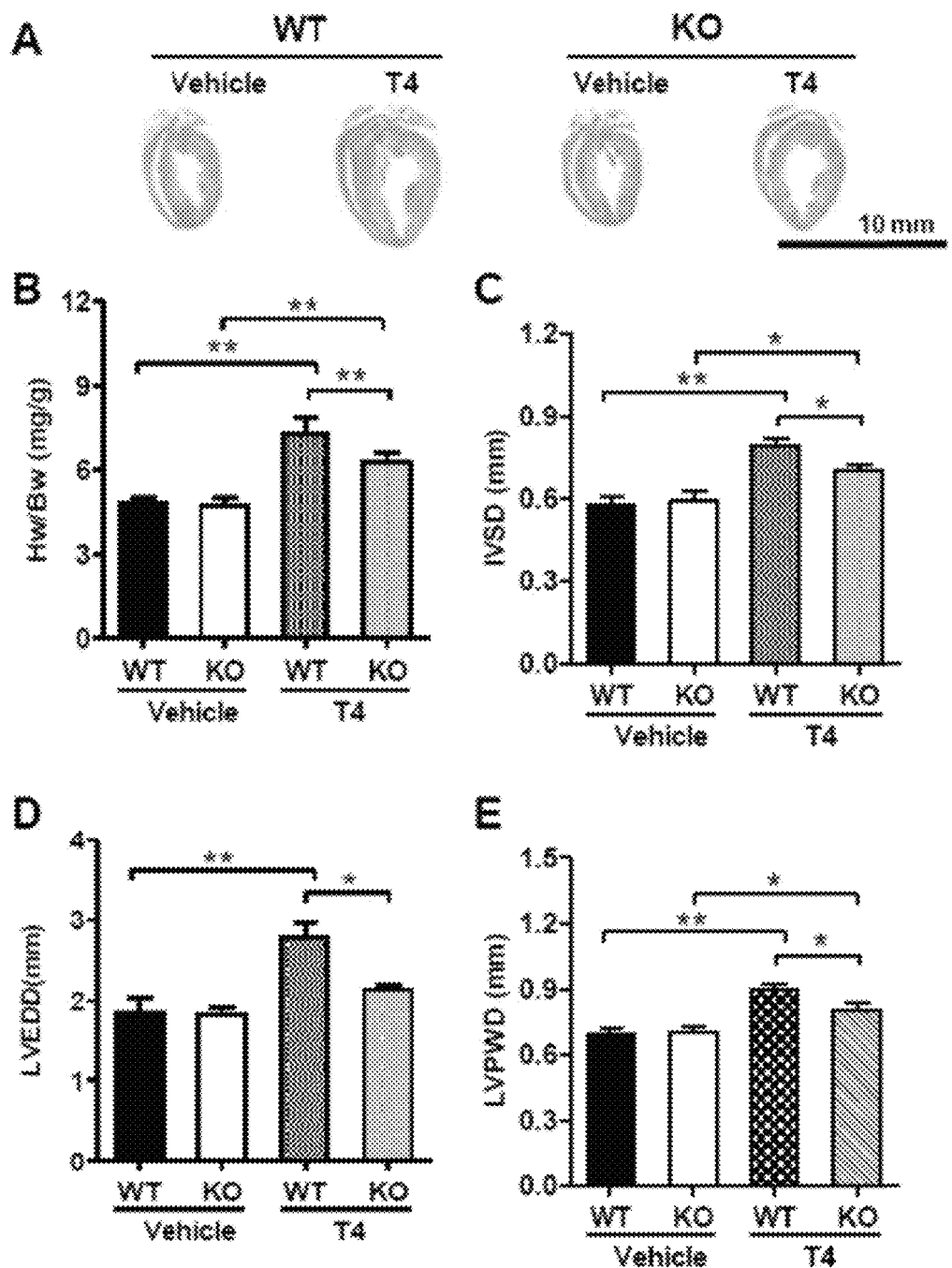
FIGS. 12A-12E show the targeted inactivation of ALCAT1 prevents the onset of hyperthyroid cardiomyopathy. WT and KO mice were treated with vehicle or T4 for 28 days, and were analyzed for FIG. 12A, morphology of the whole heart sections by H&E staining.

Targeted Inactivation of ALCAT1 Prevents the Onset of Hyperthyroid Cardiomyopathy: Oxidative stress and mitochondrial dysfunction have been implicated in cardiomyopathy. Using the knockout mice, a role of ALCAT1 in the onset of hyperthyroid cardiomyopathy was investigated next. ALCAT1 knockout mice and WT (WT) mice were treated with thyroid hormone (T4) for 2 or 28 consecutive days to observe the effects of acute and chronic hyperthyroidism on cardiac function, mitochondrial dysfunction, and signaling pathways associated with cardiac hypertrophy. Cardiac function was assessed by echocardiography performed at the end chronic treatment. In the vehicle group, there was no significant difference between the ALCAT1 knockout mice and WT mice in heart morphology and echocardiographic parameters, including interventricular septal defect (IVSD), left ventricular end diastolic diameter (LVEDD), and left ventricular posterior wall dimensions (LVPWD). The results evidence that ALCAT1 is not required for heart development or normal cardiac function (FIGS. 12A-12E). However, cardiac hypertrophy developed in WT mice after 4-weeks T4 treatment (FIG. 12A), as evidenced by marked increases in heart weight to body weight ratio (FIG. 12B), IVSD (FIG. 12C), LVEDD (FIG. 12D), and LVPWD (FIG. 12E). In contrast, ALCAT1 deficiency prevented the T4-induced cardiac hypertrophy and its related changes in echocardiographic parameters. The results provide evidence that up-regulated ALCAT1 expression contributes to the onset of cardiomyopathy induced by hyperthyroidism.

Figures 13A, 13B, 13C, 13D, 13E, 13F, 13G:
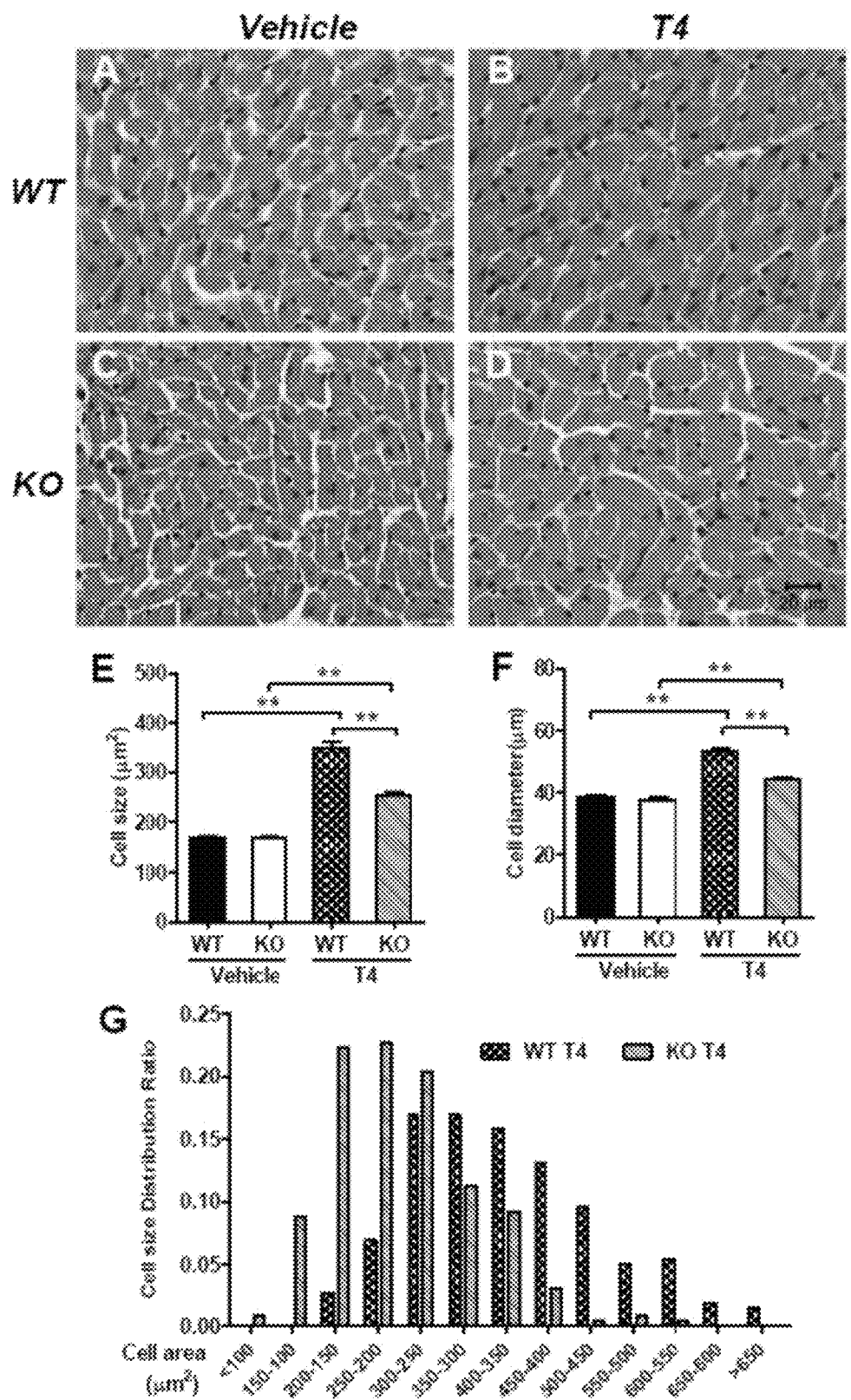
FIGS. 13A-13G show that the ablation of ALCAT1 mitigates T4-induced hypertrophic growth of cardiomyocytes.

Ablation of ALCAT1 Mitigates T4-induced Hypertrophic Growth of Cardiomyocytes: Cardiac hypertrophy is characterized by the increased size of terminally differentiated cardiomyocytes as an adaptive response to various physiological and pathophysiological stimuli. Since ALCAT1 overexpression caused hypertrophic growth of H9c2 cells, it was next determined whether ALCAT1 deficiency would prevent T4-induced hypertrophic growth of cardiomyocytes. As shown in FIGS. 13A-13G, there was no significant difference between ALCAT1 knockout mice and WT mice in cardiomyocyte size under euthyroid conditions. Consistent with hypertrophy growth, the onset of cardiomyopathy significantly increased the size of cardiomyocytes in WT mice (FIG. 13B). In contrast, the hypertrophic growth of cardiomyocytes was significantly attenuated in ALCAT1 knockout mice when compared with WT mice with hyperthyroidism (FIG. 13D). These observations are further supported by results from quantitative analysis of cell area (FIG. 13E), diameter (FIG. 13F), and size distribution of cardiomyocytes (FIG. 13G).

Figures 14A, 14B, 14C, 14D, 14E, 14F:
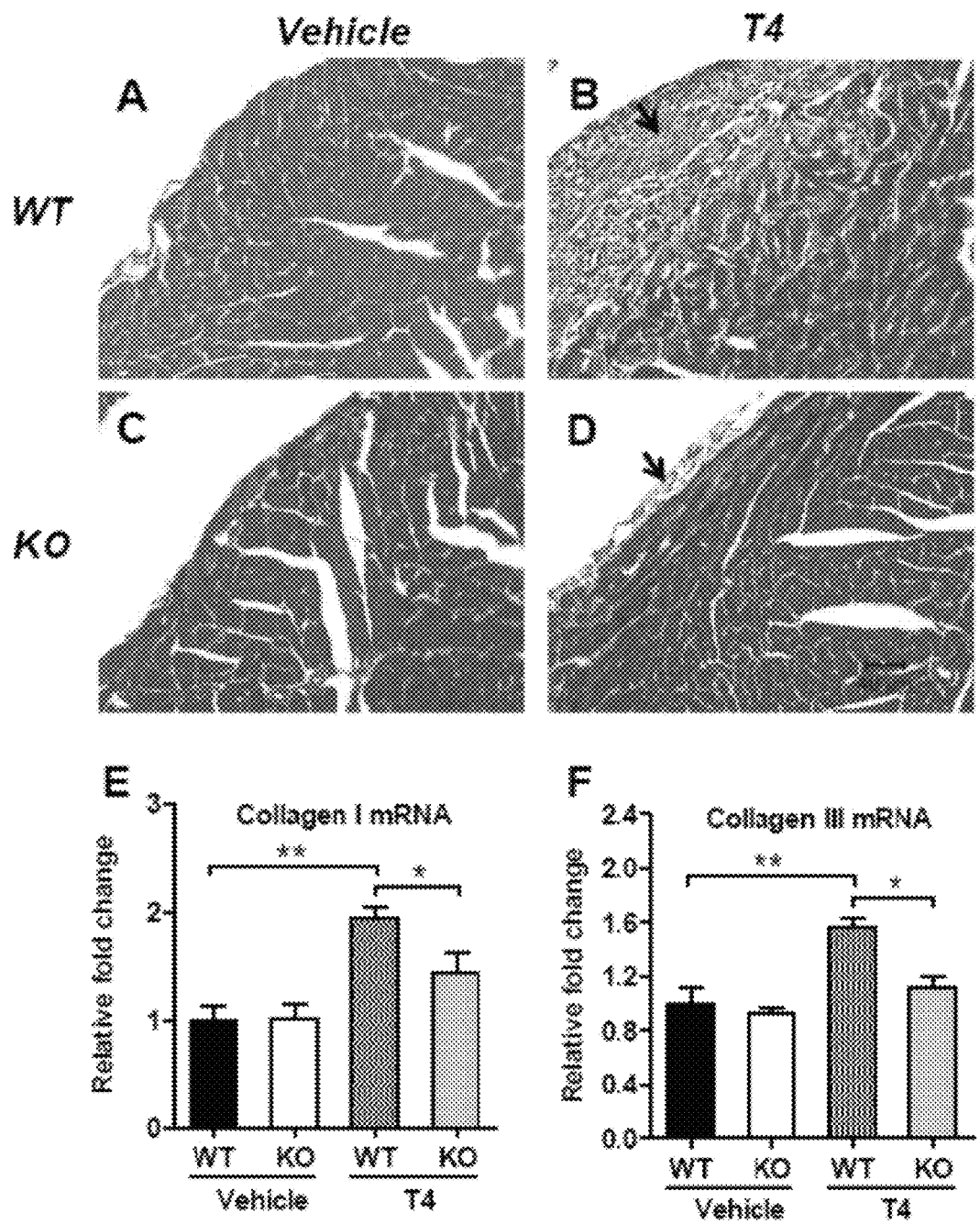
FIGS. 14A-14F show that ALCAT1 deficiency prevents the onset of T4-induced ventricular fibrosis. WT and KO mice were treated with vehicle or T4 treatment for 28 days, and then analyzed for ventricular fibrosis.
Figures 15A, 15B, 15C, 15D:
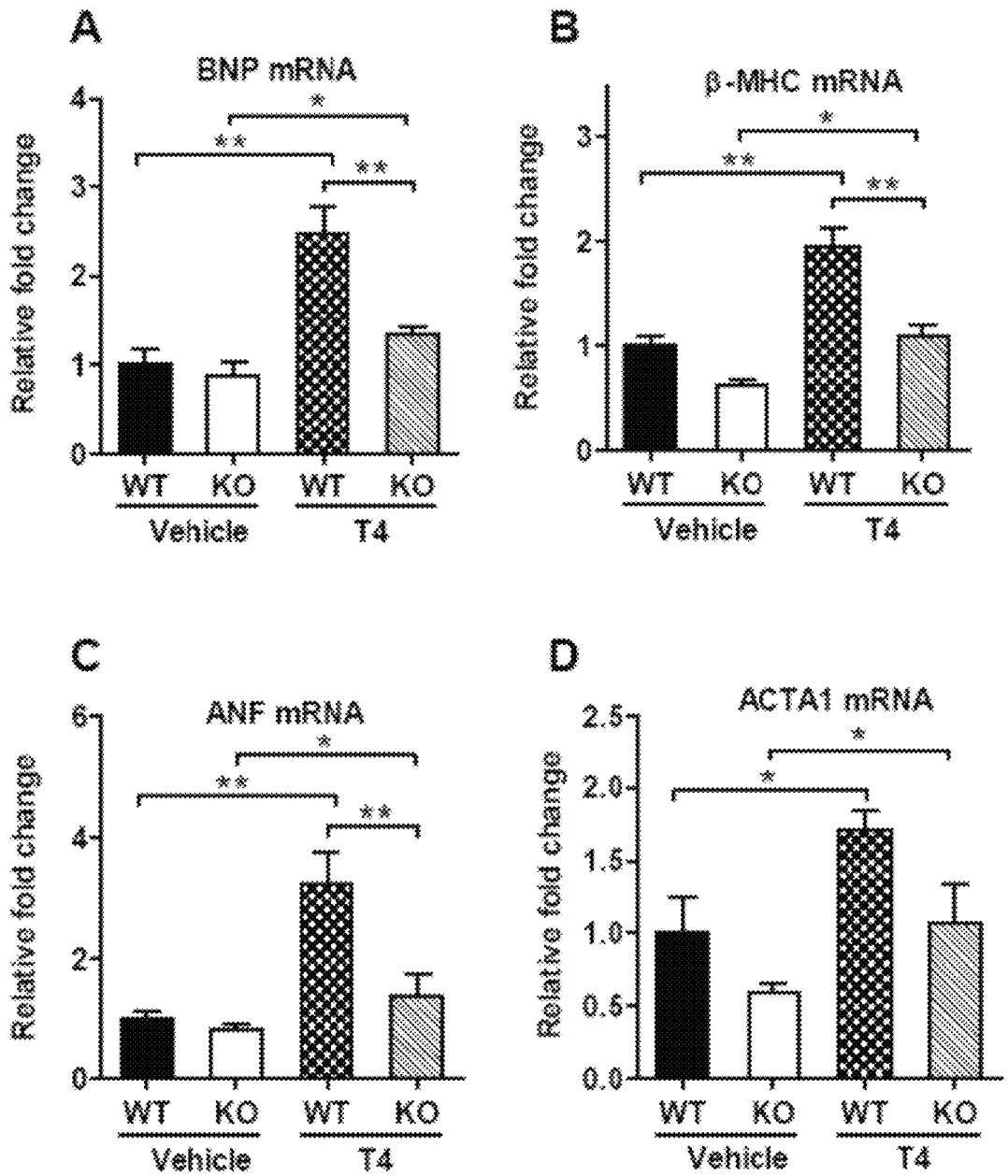
FIGS. 15A-15D show that the expression of biomarkers associated with cardiomyopathy is normalized by ALCAT1 deficiency.

ALCAT1 Deficiency Prevents T4-induced Ventricular Fibrosis: The development of cardiac hypertrophy causes structural remodeling of the myocardium, leading to excessive accumulation of collagen types I and III fibers. Ventricular fibrosis is also a major risk factor for the development of heart failure and other cardiac complications. To provide further evidence of ALCAT1 as a mediator of cardiomyopathy, a role of ALCAT1 in regulating deposition of collagen type I and III in the left ventricle was determined. Cardiac fibrosis was analyzed by Masson's trichrome staining of left ventricular sections from ALCAT1 knockout mice and the WT mice. As shown in FIG. 14B, treatment of WT mice with thyroid hormone for 28 days caused severe ventricular fibrosis, as indicated by large areas of blue staining, as a consequence of cardiomyopathy when compared with vehicle control (FIG. 14A). In contrast, ALCAT1 deficiency significantly decreased the fibrosis caused by hyperthyroidism (FIG. 14D), again implicating a role of ALCAT1 expression in cardiac dysfunction in hyperthyroid cardiomyopathy. Consistent with findings on collagen deposition, hyperthyroidism significantly increased mRNA expression of both collagen I and III in the WT mice, but not in the ALCAT1 knockout mice (FIGS. 14E & 14F).

ALCAT1 Deletion Normalizes the Expression of Biomarkers Associated with Cardiomyopathy: Persistent hypertrophy induced by pathological conditions, such as hyperthyroidism, eventually leads to heart failure, a major cause of death in industrialized nations. An elevated brain natriuretic peptide (BNP) is a specific test indicative of heart failure. BNP is a cardiac neurohormone specifically secreted from the cardiac ventricles in response to ventricular volume expansion, pressure overload, and the resultant increased wall tension. The onset of hypertrophic cardiomyopathy is also associated with induction of a subset of fetal genes, including atrial natriureticfactor (ANF), $\beta$-myosin heavy chain ($\beta$-MHC), and skeletal muscle $\alpha$-actin (ACTA1). To identify a role of ALCAT1 in the progression of cardiac hypertrophy, RNA expression of these hallmarks of cardiac hypertrophy and heart failure was analyzed. Persistent hyperthyroidism significantly increased RNA expression of all hypertrophic biomarkers in WT mice (FIGS. 15A-15D). Although hyperthyroidism also increased expression of the biomarkers in ALCAT1 knockout mice, the effect was attenuated when compared with the control group. In contrast, there was no significant difference in expression of the biomarkers between WT and ALCAT1 knockout mice when treated with vehicle, further confirming a role of ALCAT1 in the etiology of hyperthyroid cardiomyopathy.

Figures 16A, 16B, 16C, 16D, 16E, 16F, 16G:
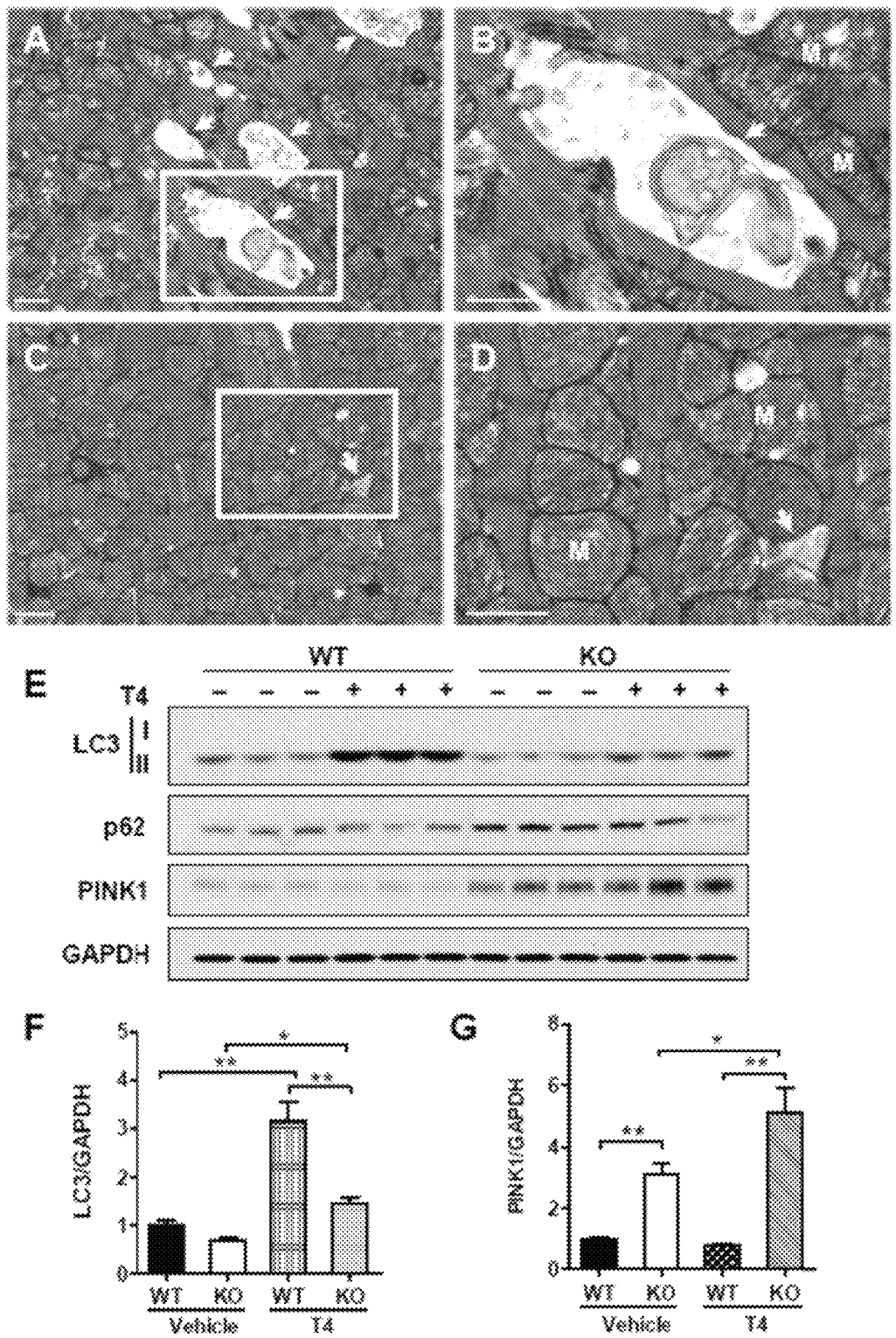
FIGS. 16A-16G show that T4-induced mitochondrial swelling and mitophagy are attenuated by ALCAT1 deficiency.
Figure 20:
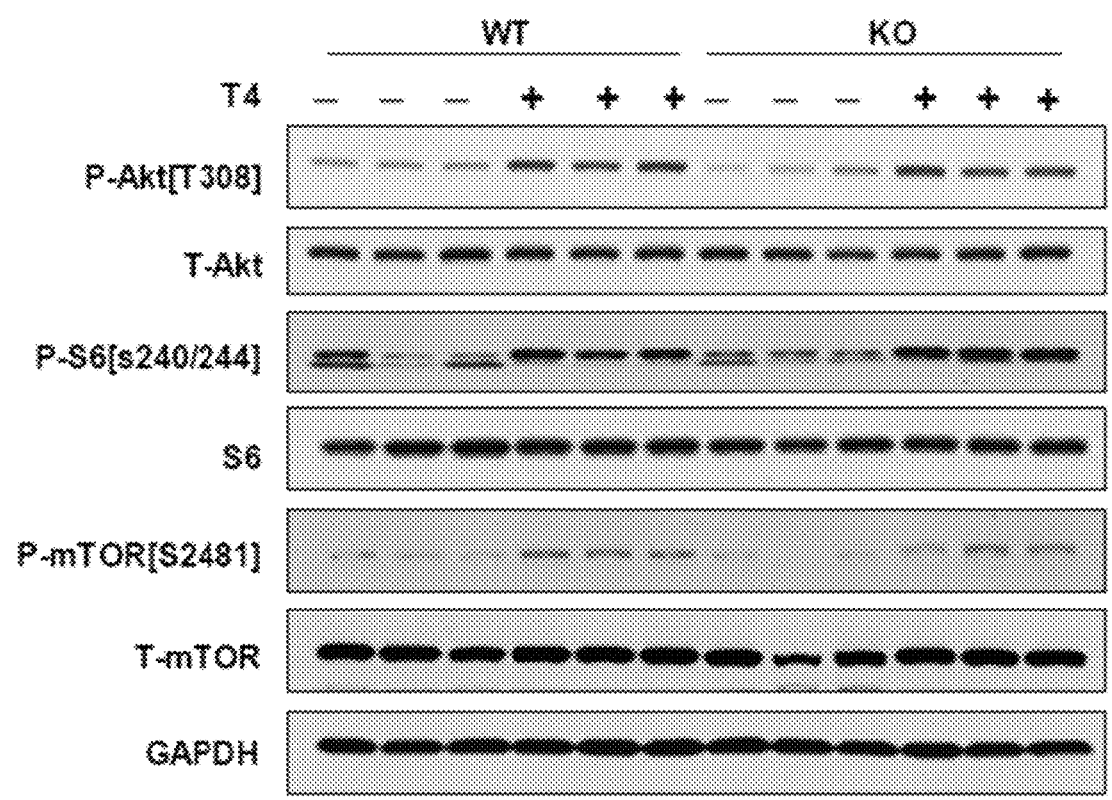
FIG. 20 shows the analysis of Akt-mTOR signal transduction pathways in cardiomyocytes in response to acute treatment of thyroid hormone. The ALCAT1 knockout (KO) and wild type control mice (WT) were treated with vehicle or T4 for 2 days, followed by Western blot analysis of phosphorylation of Akt, S6K, and mTOR by Western blot analysis using GAPDH as an internal control for protein loading.
Figures 21A, 21B, 21C, 21D:
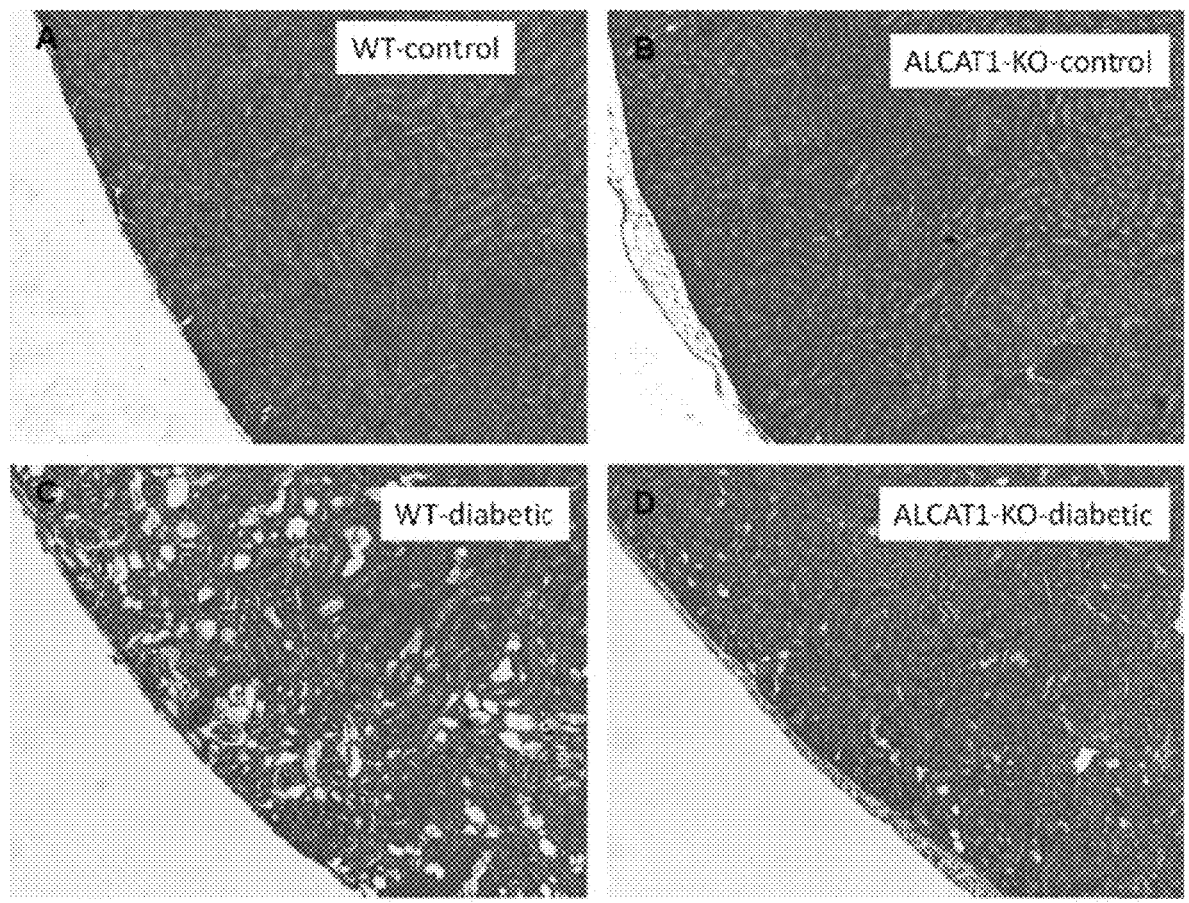
FIGS. 21A-21D show that ALCAT1 deletion prevented the onset of diabetic nephropathy. ALCAT1 knockout (KO) mice and wild type (WT) controls were intraperitoneally injected with streptozotocin (STZ) at 150 mg/kg body weight. STZ is a reagent that causes type 1 diabetes by depleting islet β-cells. Both ALCAT1 KO and WT mice developed hyperglycemia three days after the injection. After 12-weeks post-injection, renal samples were obtained, sectioned, and stained by hematoxylin and eosin (H&E) to examine diabetes-induced nephropathy. Kidneys from non-diabetic WT and KO mice were normal (FIGS. 21A and 21B). However, the WT control mice developed diabetic renal failure, as evidenced by tubular dilation, atrophy, and degeneration with cytoplasmic vacuolations in the cortex of diabetic kidneys (FIG. 21C). In contrast, these pathological changes were prevented in diabetic ALCAT1 KO mice kidneys (FIG. 21D).
Figures 22A, 22B, 22C, 22D:
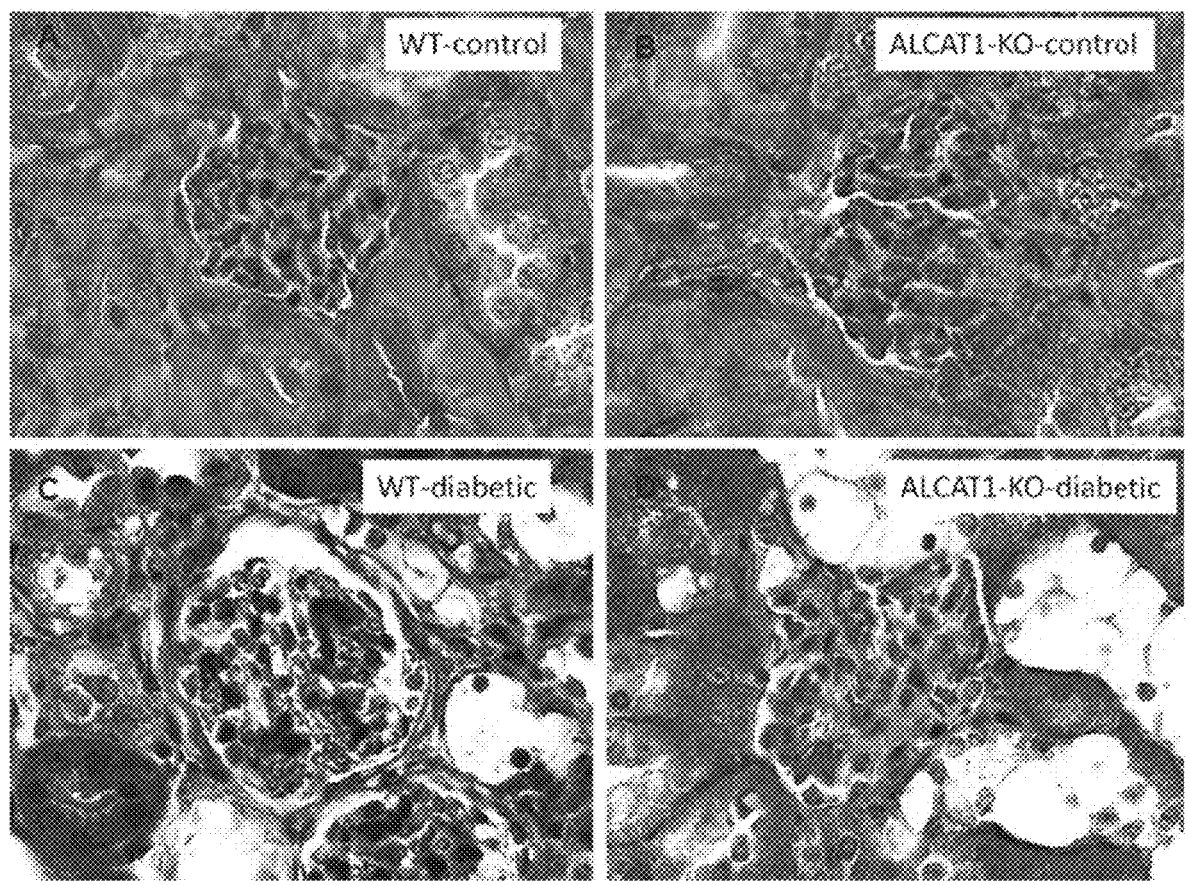
FIGS. 22A-22D show that ALCAT1 deletion prevented renal fibrosis associated with diabetic nephropathy. ALCAT1 knockout (KO) mice and wild type (WT) controls were intraperitoneally injected with streptozotocin (STZ) at 150 mg/kg body weight. Both ALCAT1 KO and WT mice developed hyperglycemia three days after the injection. After 12-weeks post-injection, renal samples were obtained, sectioned, and examined by Masson's trichrome staining to analyze changes in level of renal fibrosis, a major indicator of diabetic nephropathy.
Figures 23A, 23B, 23C, 23D, 23E, 23F:
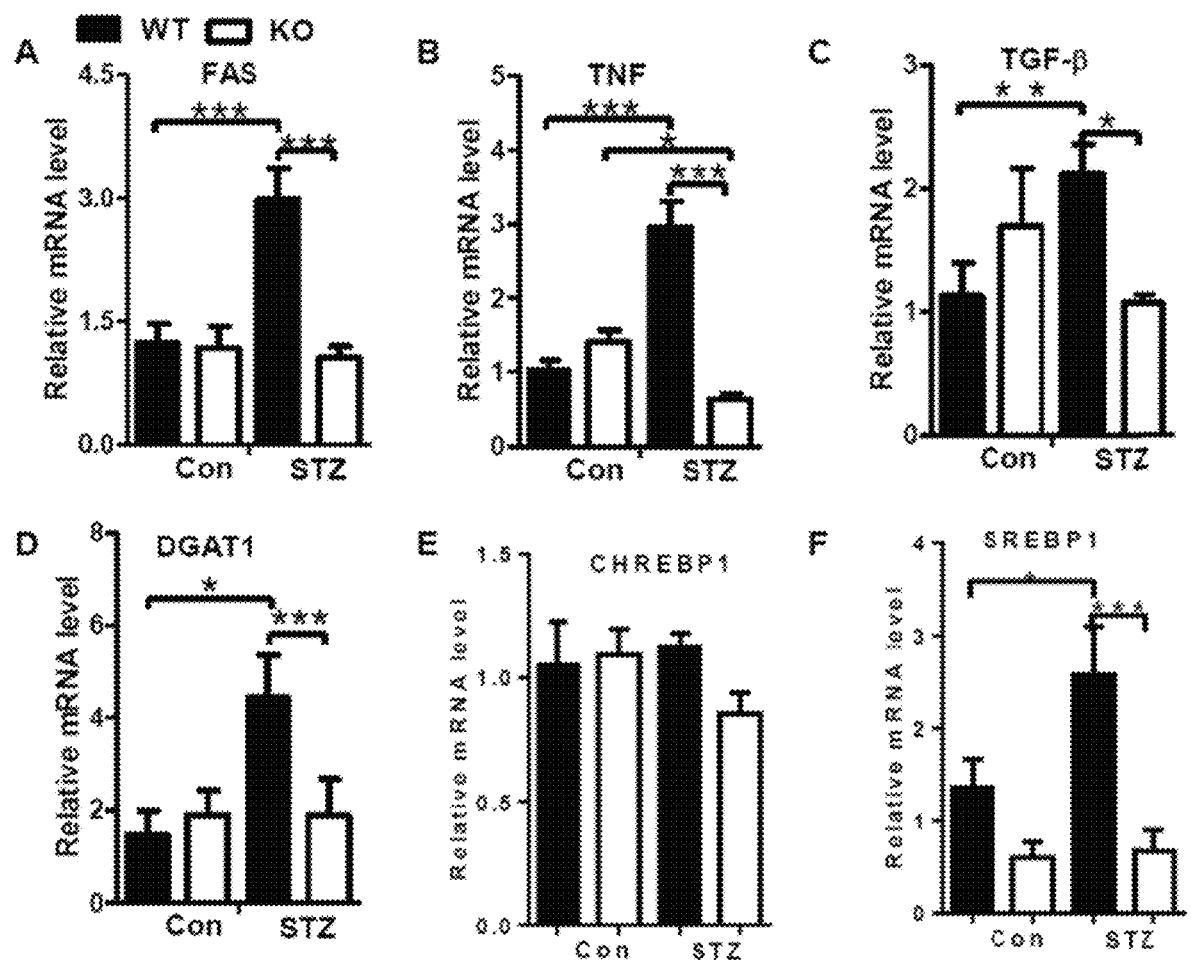
FIGS. 23A-23F show that ALCAT1 deletion suppressed mRNA expression of biomarkers associated with diabetic nephropathy. ALCAT1 knockout (KO) mice and wild type (WT) controls were intraperitoneally injected with streptozotocin (STZ) at 150 mg/kg body weight. Both ALCAT1 KO and WT mice developed hyperglycemia three days after the injection. After 12-weeks post-injection, renal samples were extracted for total RNAs, followed by RT-PCR analysis of mRNA level of biomarkers indicative of diabetic nephropathy, including FAS (FIG. 23A), TNF (FIG. 23B), TGF-β (FIG. 23C), DGAT1 (FIG. 23D), CHREBP1 (FIG. 23E), and SREBP1 (FIG. 23F). The onset of diabetic nephropathy increased mRNA expression of all the biomarkers, except CHREBP1, in the kidney of WT diabetic mice. In contrast, these pathological changes were mitigated in the kidney of diabetic ALCAT1 KO mice. N=3-6, *P<0.05, P<0.01, *P<0.001. The results evidence that an ALCAT1 inhibitor will provide a novel treatment for diabetic nephropathy, the most common cause of kidney failure in diabetic patients.
Figures 24A, 24B, 24C, 24D, 24E, 24F:
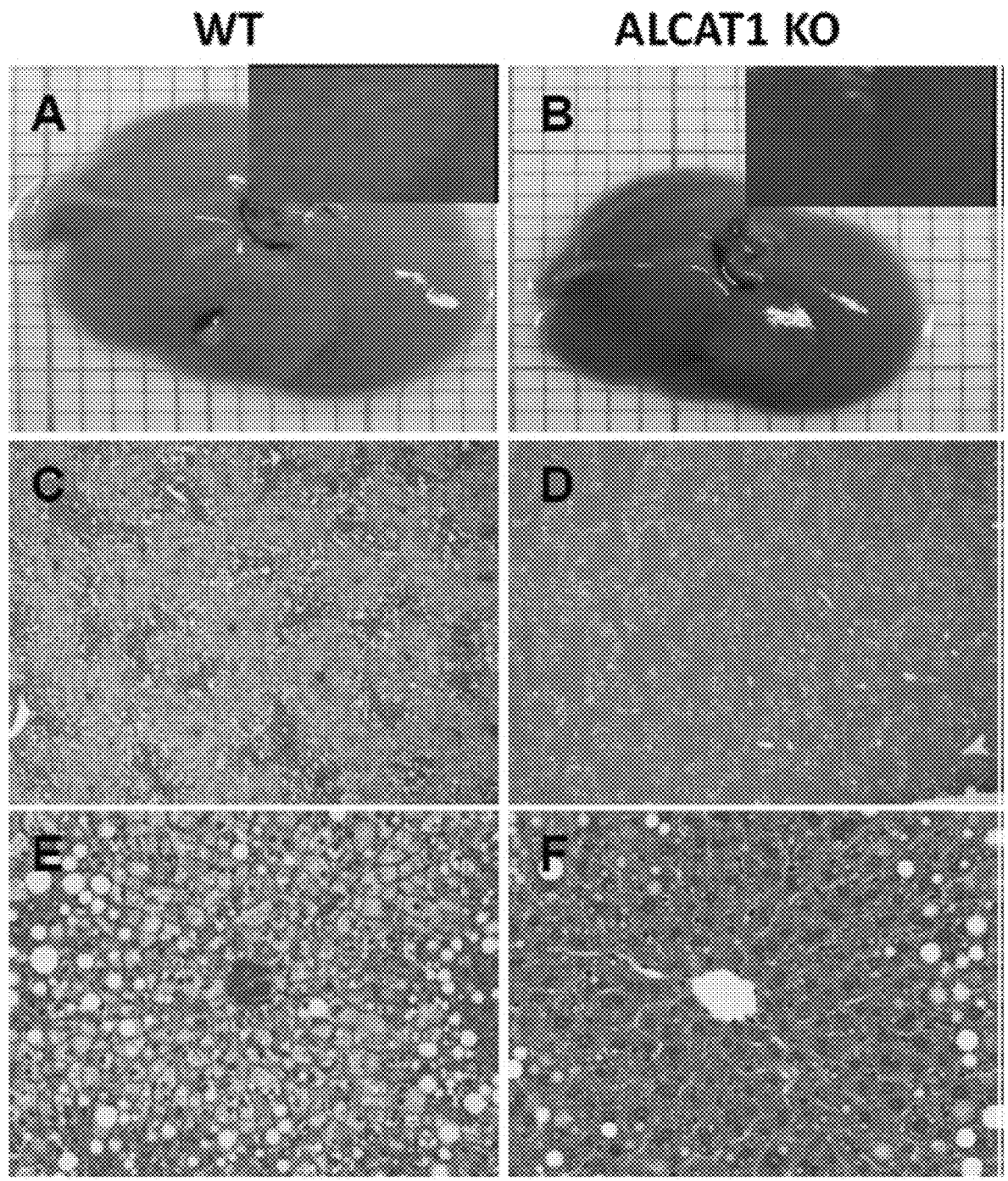
FIGS. 24A-24F show that ALCAT1 deletion prevented the onset of fatty liver diseases induced by high-fat diet. ALCAT1 knockout (KO) mice wild type (WT) controls were fed with a high-fat diet (HFD) for 18 consecutive weeks to induce the onset of obesity and its related fatty liver diseases. At the end of the feeding studies, the mice were analyzed for pathological changes in the liver associated with diet-induced obesity by H&E staining. In response to the onset of diet-induced obesity, the WT mice developed typical fatty liver diseases, as evidenced by enlarged and pale liver (FIG. 24A). Additionally, H&E staining revealed the presence of intracellular vacillations and severe hepatic intracellular vacuolation in WT mice (FIG. 24C, enlarged in FIG. 24E). In contrast, these pathological defects were completely ablated in ALCAT1 KO mice fed with HFD (FIGS. 24B, 24D, enlarged in 24F).
Figures 25A, 25B, 25C, 25D, 25E, 25F:
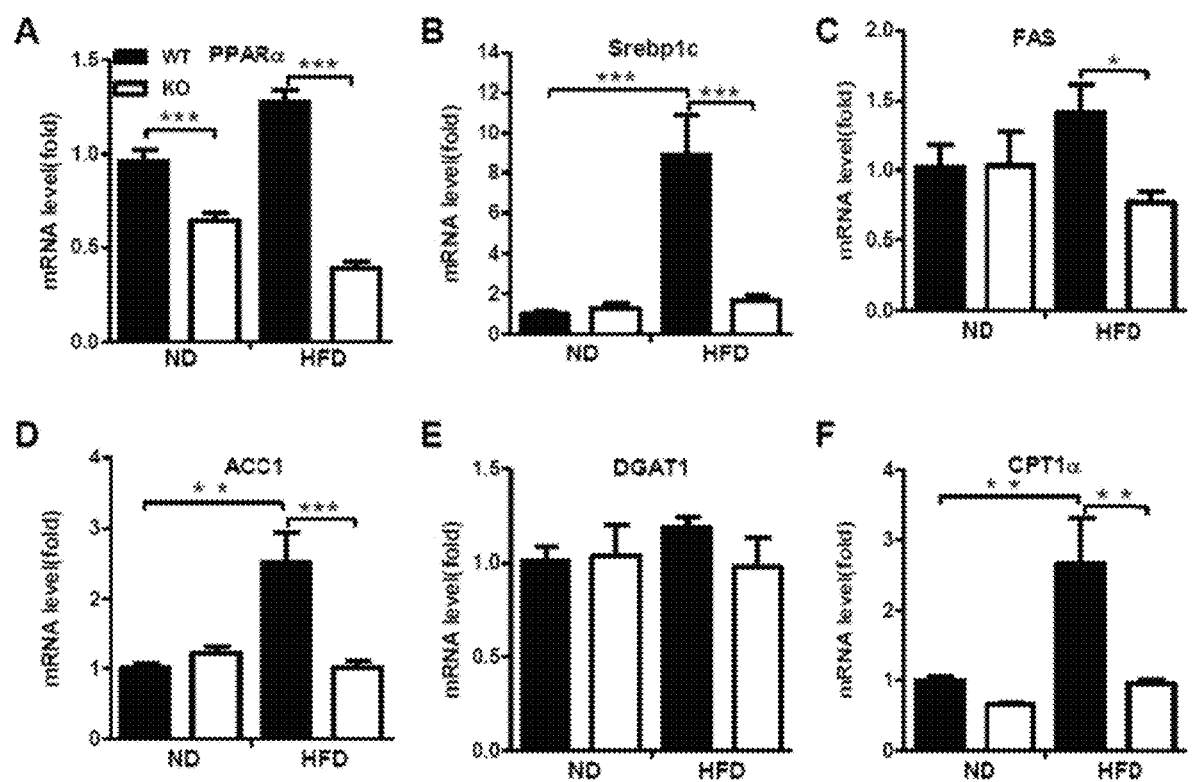
FIGS. 25A-25F show that ALCAT1 deletion suppressed mRNA expression of biomarkers associated with fatty liver diseases. ALCAT1 knockout (KO) mice and wild type (WT) controls were fed a high-fat diet (HFD) for 18 consecutive weeks to induce the onset of obesity and its related fatty liver diseases. At the end of the feeding studies, the mice were analyzed for changes in mRNA expression of lipogenic genes in the liver associated with heptosteatosis, including PPARα (FIG. 25A), Srebp1c (FIG. 25B), FAS (FIG. 25C), ACC1 (FIG. 25D), DGAT1 (FIG. 25E), and CPT1α (FIG. 25F). The onset of hepatosteatosis significantly increased mRNA expression of PPARα, Srebp1c, FAS, ACC1, and CPT1α in the liver of WT control mice. In contrast, these pathological changes were completely mitigated in the liver of ALCAT1 KO mice. N=3-6, *$P<0.05$, $P<0.01$, *$P<0.001$. The results evidence that an ALCAT 1 inhibitor will provide a novel treatment for hepatic steatosis, the most common defect in obesity and type 2 diabetes.
Figures 26A, 26B, 26C, 26D:
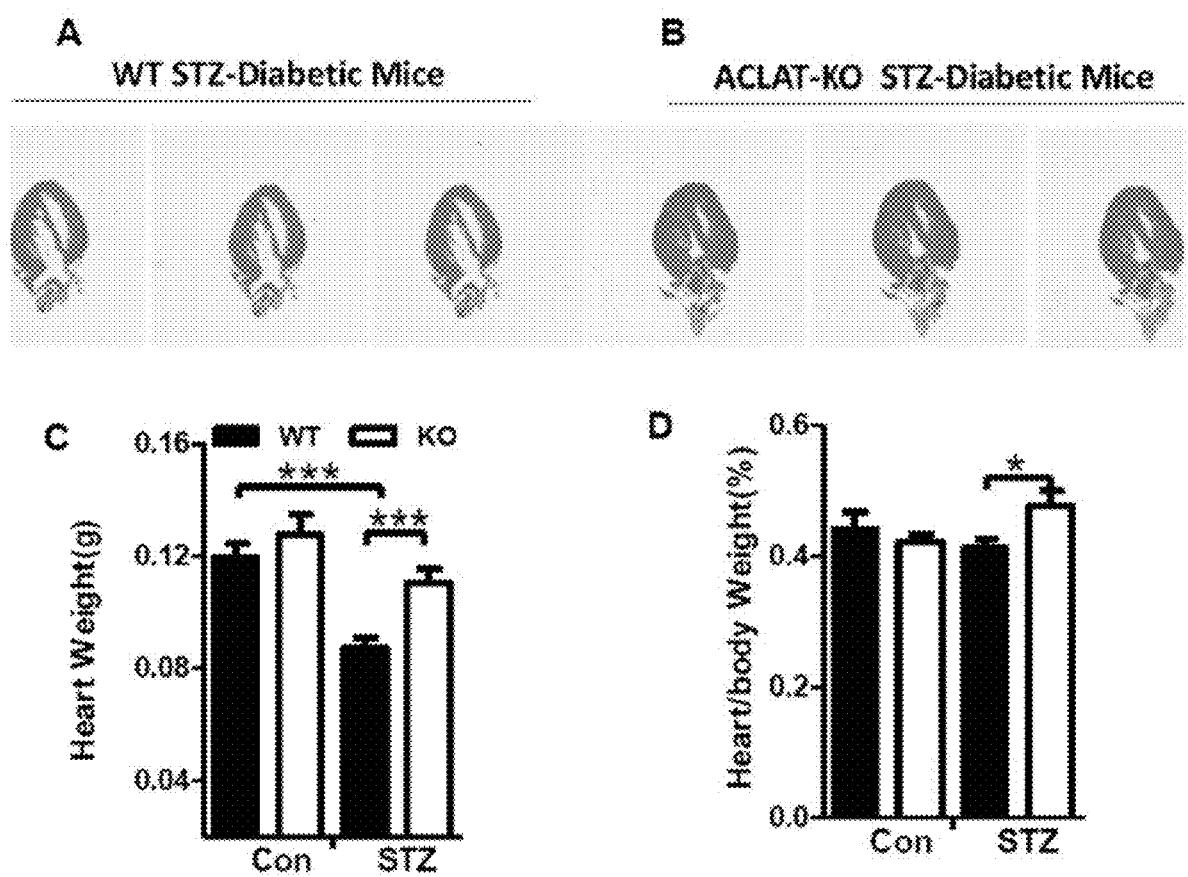
FIGS. 26A-26D show that ALCAT1 knockout mice are protected from diabetes-induced cardiac atrophy. ALCAT1 knockout (KO) mice and wild type (WT) controls were intraperitoneally injected with streptozotocin (STZ) at 150 mg/kg body weight. Both ALCAT1 KO and WT mice developed hyperglycemia three days after the injection. After 12-weeks post-injection, the mice were analyzed for changes in heart atrophy and morphology by H&E staining. The onset of type 1 diabetes caused severe cardiac dilation and atrophy in WT control mice (FIG. 26A), as evidenced by a significant reduction in heart weight (FIG. 26C) and heart/body weight ratio (FIG. 26D). In contrast, these pathological defects were mitigated in ALCAT1 KO diabetic mice which exhibited normal cardiac morphology (FIG. 26B) and heart weight (FIG. 26C and FIG. 26D). N=3-6, *$P<0.05$, $P<0.01$, *$P<0.001$.
Figures 27A, 27B, 27C, 27D:
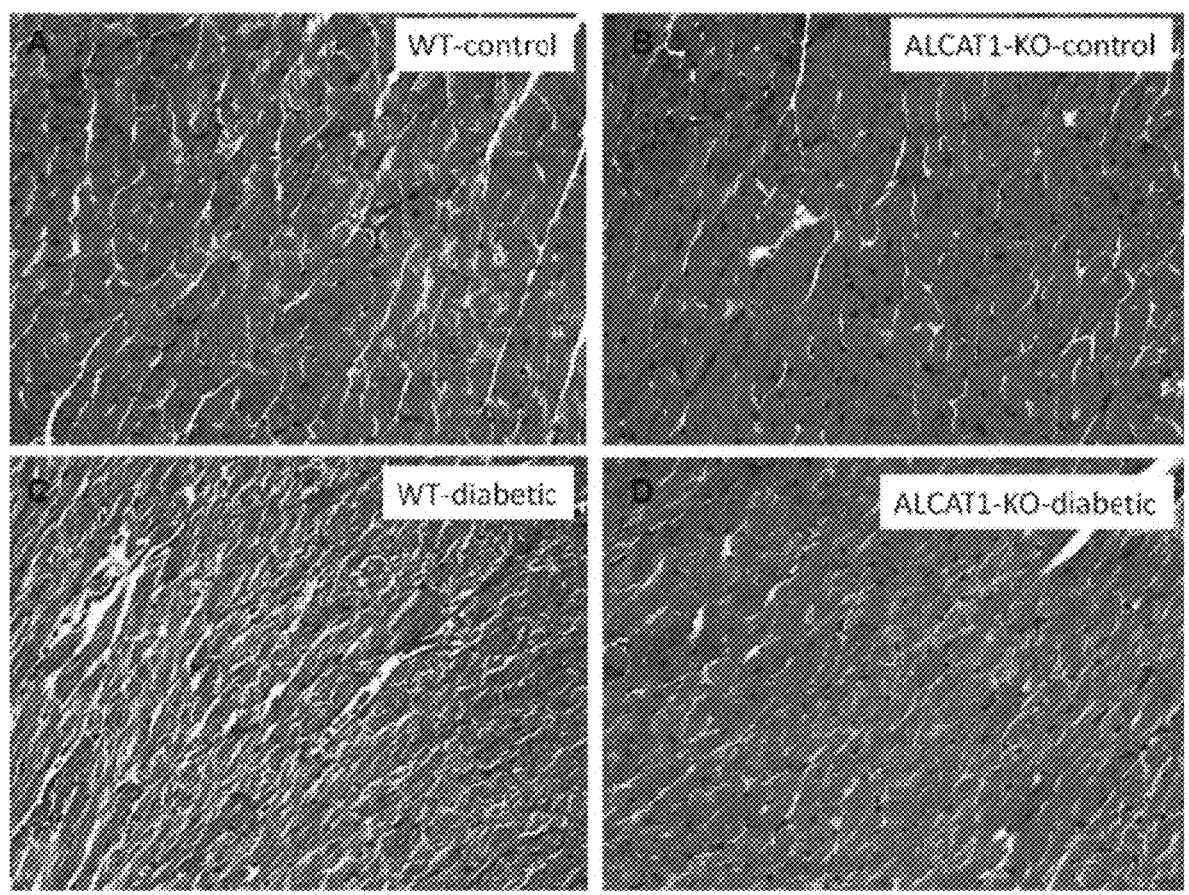
FIGS. 27A-27D show that ALCAT1 deletion prevents the onset of diabetic cardiac fibrosis. ALCAT1 knockout (KO) mice and wild type (WT) controls were intraperitoneally injected with streptozotocin (STZ) at 150 mg/kg body weight. Both ALCAT1 KO and WT mice developed hyperglycemia three days after the injection. After 12-weeks post-injection, heart samples were sectioned and analyzed by Masson's trichrome staining to examine the effect of ALCAT1 deficiency on cardiac fibrosis, a major marker for diabetic heart failure. Both WT control mice and ALCAT1 KO mice exhibited normal cardiac structure under non-diabetic condition (FIG. 27A & FIG. 27B). However, the onset of diabetes in WT control mice caused severe cardiac fibrosis (FIG. 27C), as evidenced by heavy staining of blue color. In contrast, ALCAT1 deficiency prevented the hyperglycemia-induced deposition of collagen fibers in cardiac tissue in ALCAT1 KO mice (FIG. 27D). The results suggest that an ALCAT1 inhibitor will provide a novel treatment for diabetic heart failure, the most common cause of fatality in diabetic patients.
Figures 28A, 28B, 28C, 28D, 28E, 28F:
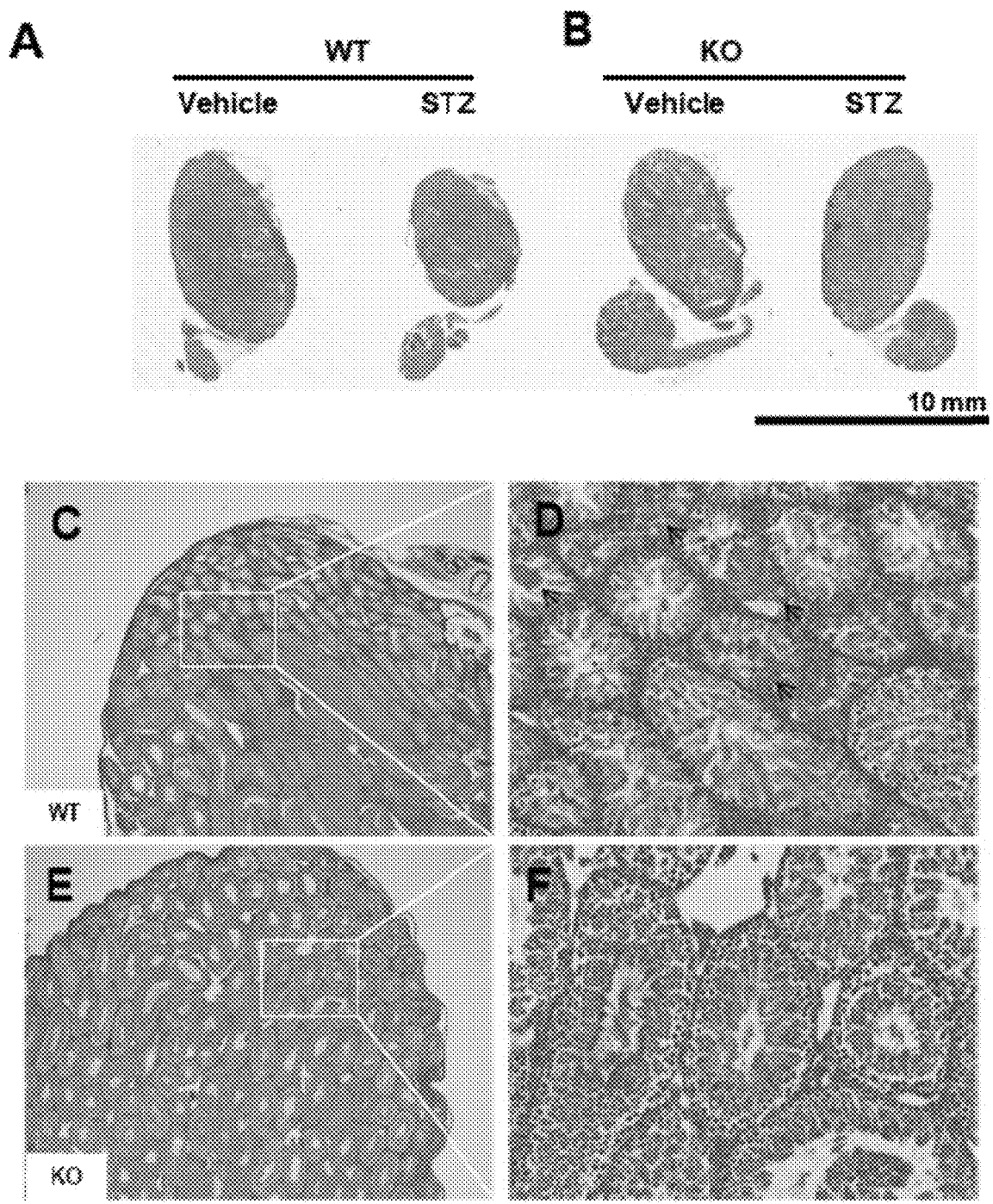
FIGS. 28A-28F show that ALCAT1 knockout mice are protected from diabetes-induced atrophy of testis. ALCAT1 knockout (KO) mice and wild type (WT) controls were intraperitoneally injected with streptozotocin (STZ) at 150 mg/kg body weight. STZ is a reagent that causes type 1 diabetes by depleting islet β-cells. Both ALCAT1 KO and WT mice developed hyperglycemia three days after the injection. After 12-weeks post-injection, testis samples were sectioned and analyzed by H&E staining to examine a role of ALCAT1 in regulating diabetes-induced testis atrophy.
Figures 29A, 29B, 29C, 29D:
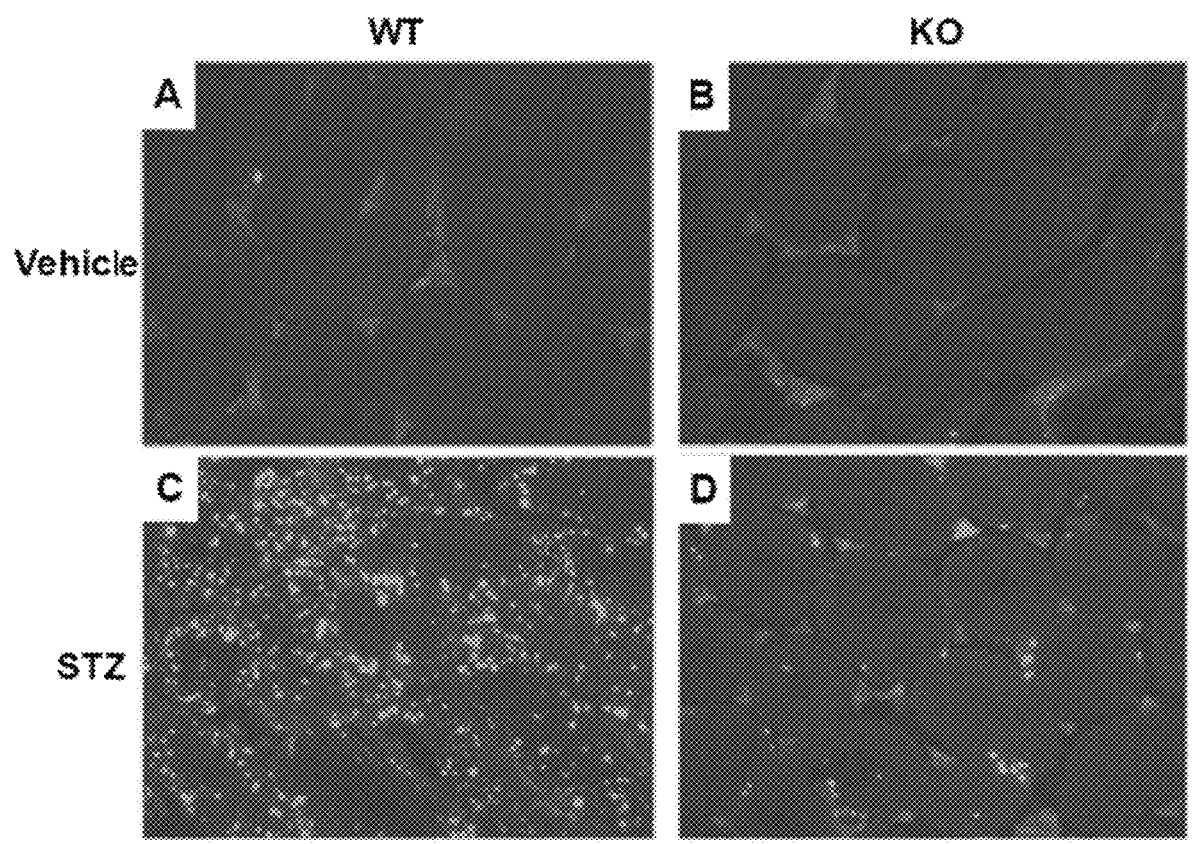
FIGS. 29A-29D show that ALCAT1 knockout mice are protected from diabetes-induced apoptosis in testis. ALCAT1 knockout (KO) mice and wild type (WT) controls were intraperitoneally injected with streptozotocin (STZ) at 150 mg/kg body weight. After 12-weeks post-injection, testis samples were sectioned and analyzed for hyperglycemia-induced apoptosis by TUNEL staining. The ALCAT1 KO mice and WT controls are indistinguishable at the level of apoptosis in testis under euglycemic condition (FIGS. 29A and 29B). However, the onset of diabetes triggered dramatic cell death in testis of WT control mice, as evidenced by the increased number of cells that were positive for TUNEL staining (FIG. 29C). In contrast, ALCAT1 deficiency prevented the onset of apoptosis associated with diabetes in testis of ALCAT1 KO mice (FIG. 29D).
Figures 30A, 30B, 30C, 30D, 30E, 30F:
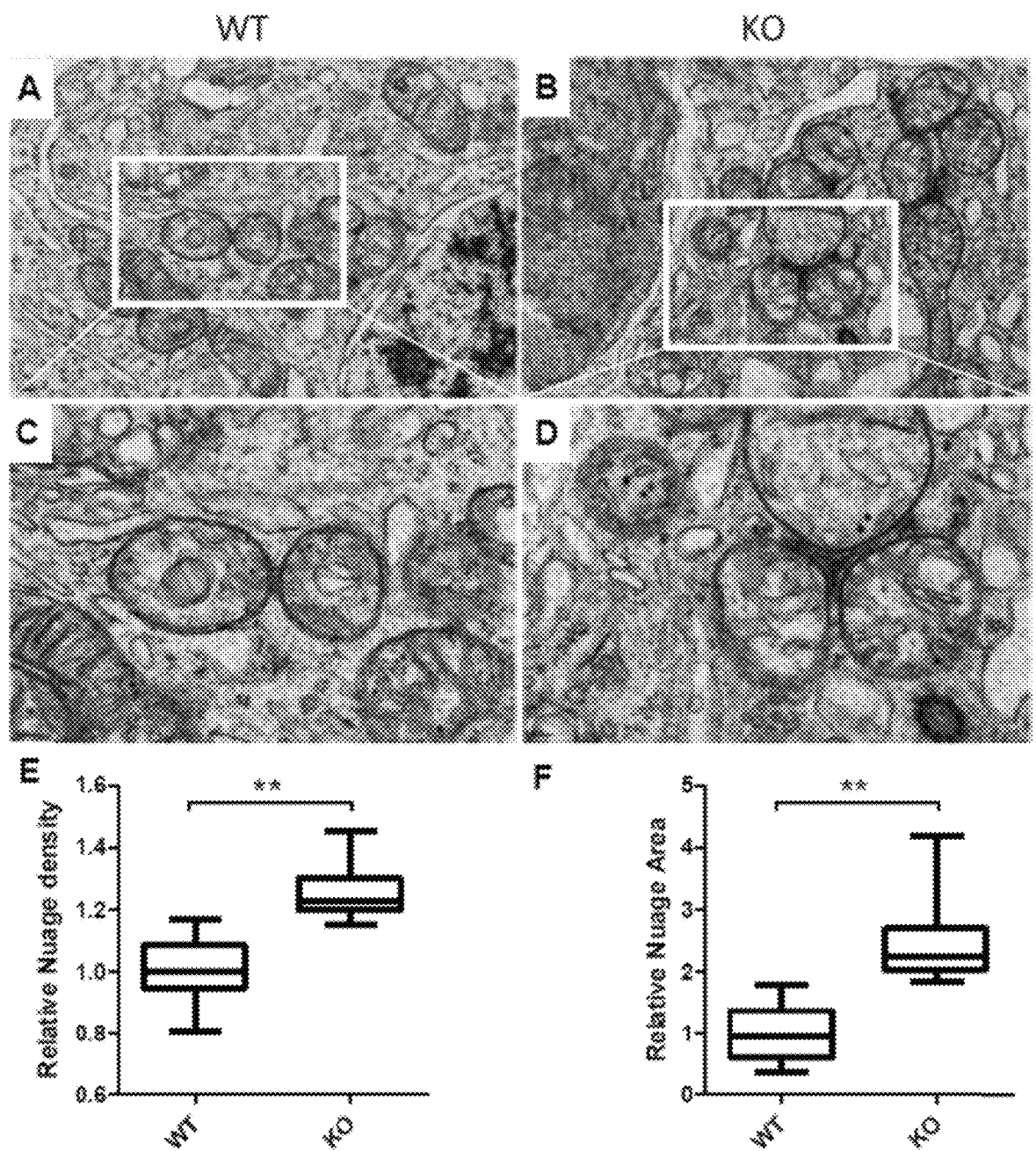
FIGS. 30A-30F show that ALCAT1 knockout mice exhibited high level of nauge formation in testis. Testis samples were analyzed for nauge formation in 3-weeks old WT (FIG. 30A, highlighted in FIG. 30C) and ALCAT1 KO mice (FIG. 30B, highlighted in FIG. 30D). Nauge is a unique feature of mitochondria in testis. NIH ImageJ software was used to quantify nauge density (FIG. 30E), which was then normalized to the density of adjacent mitochondrial matrix to control for contrast and darkness, and relative nauge area (FIG. 30F). Means±SEM (n=24). Consistent with the observations in previous figure, ALCAT1 deficiency improved mitochondrial function in testis, as evidenced by increased nauge formation in testis of the ALCAT1 KO mice. Together, the results evidence that an ALCAT1 inhibitor will provide a novel treatment for diabetes-induced reproductive degeneration, such as erectile dysfunction, a common defect in diabetic patients. *$P<0.05$, **$P<0.01$.

Inactivation of ALCAT1 Prevents Mitochondrial Swelling and Mitophagy by Stimulating PINK1 Expression: Selective mitochondria autophagy, also known as mitophagy, contributes to the maintenance of mitochondrial quality by eliminating damaged mitochondria. Mitophagy also plays an essential role in maintaining mitochondrial quantity and quality by reducing mitochondrial production of ROS and mutation of mitochondrial DNA. Hence, cardiac-specific deficiency of autophagy causes cardiomyopathy. Using EM analysis of ventricle sections, a role of ALCAT1 in mitochondrial dysfunction and autophagy associated with hyperthyroid cardiomyopathy was determined. Consistent with severe oxidative stress in hyperthyroidism, the onset of hyperthyroid cardiomyopathy is associated with mitochondrial swelling, disorganized cristae, and abnormal structure of the mitochondria in WT mice (FIG. 16A, highlighted in FIG. 16B). In contrast, these damages were largely mitigated by ALCAT1 deficiency (FIG. 16C, highlighted in FIG. 16D). As a compensatory response to damaged mitochondria, the expression level of cardiac LC3, an autophagosome marker, was significantly up-regulated by hyperthyroidism in WT mice (FIG. 16E, quantified in FIG. 16F). Furthermore, the expression of the p62 protein, which is negatively correlated with autophagy, was significantly lower in WT mice. In support of these observations, the number of autophagic mitochondria was significantly higher in WT mice in response to the onset of hyperthyroidism, when compared with the ALCAT1 knockout mice (FIG. 20).

PTEN-induced putative kinase 1 (PINK1) is a serine/threonine protein kinase that protects against mitochondrial dysfunction during cellular stress by promoting the clearance of damaged mitochondria via mitophagy. PINK1 deficiency causes oxidative stress and mitophagy, leading to cardiomyopathy in mice. In further support of a causative role of ALCAT1 in mitochondrial dysfunction, cardiac PINK1 expression was significantly upregulated by ALCAT1 deficiency, which is consistent with decreased levels of oxidative stress and mitophagy in the ALCAT1 knockout mice (FIG. 16E, quantified in FIG. 16G). These findings provide evidence that oxidative stress by ALCAT1 plays a key role in mitochondrial dysfunction and mitophagy associated with hyperthyroid cardiomyopathy.

Figure 17A:
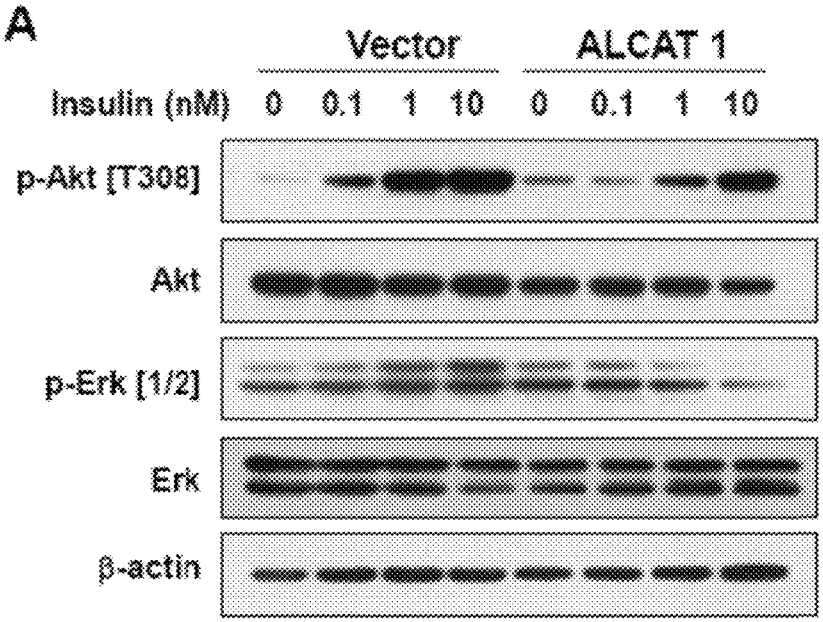
FIGS. 17A-17C show that oxidative stress by ALCAT1 regulates Akt-mTOR signaling in cardiomyocytes.
Figure 17B:
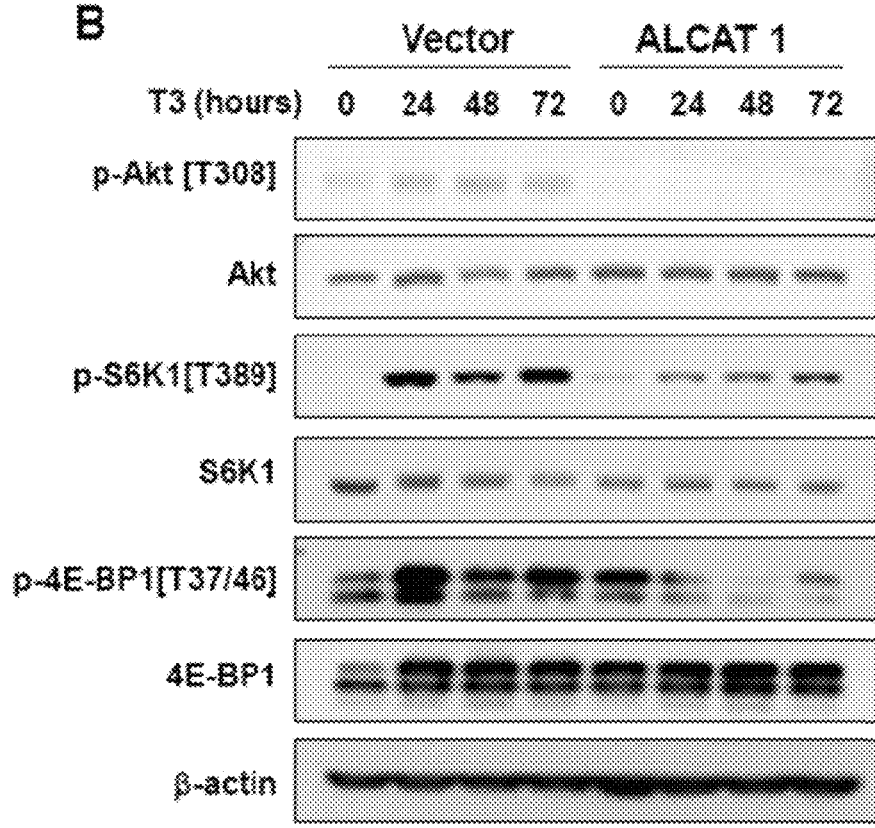
Figure 17C:
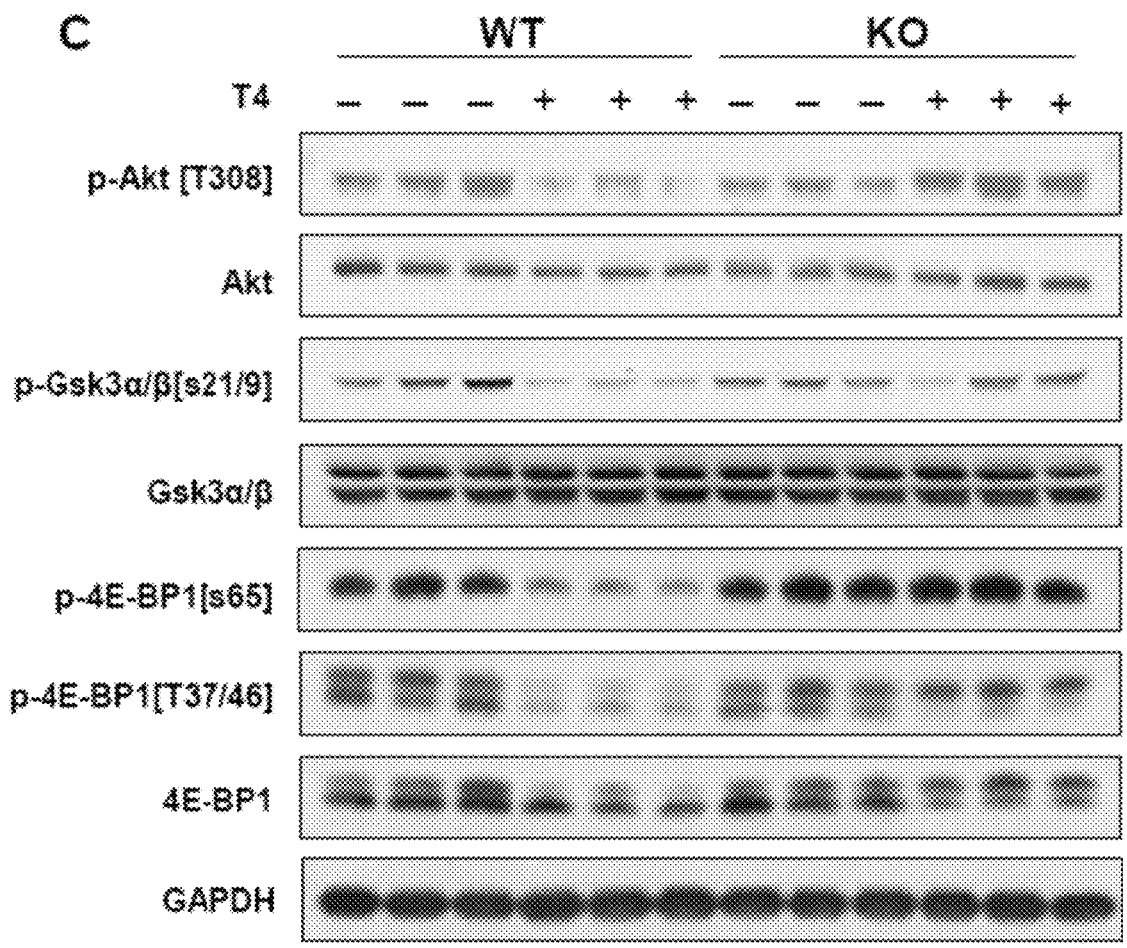

Oxidative Stress by ALCAT1 Regulates Akt-mTOR Signal Transduction Pathways in Cardiomyopathy: Hyperthyroidism leads to cardiomyopathy by stimulating protein synthesis in the cardiomyocytes. To identify molecular mechanisms underlying a role of ALCAT1 in hypertrophic growth, the effects of ALCAT1 overexpression and deficiency were analyzed on signal transduction pathways involved in cellular growth and proliferation, including phosphorylation of Akt, Erk, S6K, and 4E-BP1, in H9c2 cells and in mice with hyperthyroidism. Increased ROS levels lead to insulin resistance which plays a causative role in cardiac dysfunction. As shown in FIG. 17A, treatment of H9c2 cells with insulin dose-dependently stimulated phosphorylation of Akt and Erk in vector control cells. In contrast, ALCAT1 overexpression significantly attenuated insulin-stimulated Akt phosphorylation concurrent with ablation of Erk phosphorylation, providing evidence of severe insulin resistance (FIG. 17A). Furthermore, chronic oxidative stress by ALCAT1 also completely prevented T3-induced activation of Akt, S6K, and 4E-BP signaling pathways in H9c2 cells (FIG. 17B). Consistent with hypertrophic growth of H9c2 cells caused by ALCAT1 overexpression, the basal phosphorylation of S6K and 4E-BP was significantly higher in ALCAT1-expressing H9c2 cells. In support of the findings in H9c2 cells, short term treatment of mice with thyroid hormone stimulated cardiac Akt-mTOR phosphorylation in both ALCAT1 knockout mice and the WT mice (FIG. 20). However, chronic hyperthyroidism caused significant down-regulation of the Akt-mTOR signaling pathways by the onset of cardiomyopathy, as evidenced by significantly lower phosphorylation of Akt and 4E-BP (FIG. 17C). Hyperthyroidism also downregulated phosphorylation of Gsk3 whose deficiency causes cardiomyopathy. Consistent with a lack of cardiac hypertrophy, ALCAT1 deficiency completely prevented the downregulation of phosphorylation of these signaling proteins induced by chronic hyperthyroidism.

Discussion

CL remodeling plays an important role in regulating function of the heart, a tissue with perpetually high energy demand from oxidative phosphorylation. The biological function of CL is determined by the structure of its fatty acyl chains. In the heart, functional CL is enriched with linoleic acid which is important in supporting the activity of mitochondrial enzymes and proteins (Claypool S M & Koehler C M. Trends Biochem Sci. 2012 January; 37(1):32-41). Consequently, a loss of TLCL, the signature CL in the heart, as a consequence of pathological remodeling has been implicated in the etiology of cardiomyopathy and heart failure. However, the enzyme(s) responsible for pathological remodeling of CL in heart diseases remains elusive. ALCAT1 is a lysocardiolipin acyltransferase that catalyzes deleterious remodeling of CL, leading to the production of aberrant CL species commonly found in heart diseases (Li J, et al. (2010) Cell Metab 12(2):154-165). Using H9c2 cardiac cells stably expressing ALCAT1 and mice with targeted inactivation of the ALCAT1 gene, in the present study the role of ALCAT1 overexpression and deficiency in the development of cardiomyopathy caused by hyperthyroidism was studied. These results identify for the first time a key role of ALCAT1 in regulating the onset of hypertrophic cardiomyopathy. Accordingly, overexpression of ALCAT1 caused hypertrophic growth of H9c2 cells, whereas ablation of ALCAT1 prevented the onset of T4-induced cardiomyopathy and its related cardiac dysfunction, including ventricular hypertrophy, ventricular fibrosis, and elevated expression of collagen type I and III. Additionally, ALCAT1 deficiency also normalized the expression of hypertrophic biomarkers, including BNP, β-MHC, ANF, and ACTA1 which are commonly up-regulated by the onset of cardiomyopathy. In support of a potential causative role of ALCAT1 in the etiology of hypertrophic cardiomyopathy, the ALCAT1 mRNA expression is significantly up-regulated by the onset cardiomyopathy in the heart. Furthermore, CL remodeling by ALCAT1 causes depletion of TLCL, which has been identified as the primary cause of cardiomyopathy in Barth syndrome.

Hypothyroidism significantly increases oxidative stress which is known to cause CL peroxidation and heart failure (Drummond G R, et al., (2011) Nat Rev Drug Discov 10(6):453-471; Lesnefsky E J, et al. (2004) Am J Physiol-Heart & Cir Physiol 287(1):H258-267). Pathological CL remodeling in age-related diseases is believed to exacerbate ROS production through enrichment of DHA content in CL. In support of this hypothesis, DHA content in CL significantly increases lipid peroxidation index, which has been implicated in mitochondrial dysfunction in aging and age-related diseases. Accordingly, the onset of aging is also associated with depletion of cardiac TLCL with concurrent enrichment of DHA in CL. Additionally, mitochondrial membrane DHA content is negatively correlated with lifespan and positively correlated with ROS production and lipid peroxidation index. Hence, increased DHA content and CL peroxidation have been identified as common defects associated with cardiac abnormality in hyperthyroidism, diabetes, ischemia-reperfusion injury, and heart failure. In support of ALCAT1 as a key mediator of oxidative stress in T4-induced cardiomyopathy, CL remodeling by ALCAT1 increases DHA content in CL, whereas targeted deletion of ALCAT1 significantly increases the cardiac level of TLCL in the ALCAT1 knockout mice. Consistent with these findings, the results from the present study showed that overexpression of ALCAT1 caused severe oxidative stress, lipid peroxidation, and mtDNA depletion in H9c2 cardiac cell line, leading to impaired differentiation into cardiac myotubes. In direct support of ALCAT1 as the primary mediator of oxidative stress in hyperthyroidism, ablation of ALCAT1 expression completely prevented cardiac lipid peroxidation caused by hyperthyroidism.

Mitophagy is a targeted defense against oxidative stress, mitochondrial dysfunction, and aging. Cardiac mitophagy is up-regulated by the onset of cardiac hypertrophy and heart failure in humans and rodents. Loss of autophagy causes severe oxidative stress in yeast and cardiomyopathy in mice. PINK1 is a key regulator of mitophagy when mutated causes Parkinson's disease. PINK1 also plays an essential role in normal cardiac function. PINK1 protects against mitochondrial dysfunction and oxidative stress by promoting the clearance of damaged mitochondria through regulation of mitophagy. Consequently, PINK1 expression is down-regulated in end-stage human heart failure, whereas PINK1 deficiency in mice causes oxidative stress, mitophagy, and cardiomyopathy. In further support of a causative role of ALCAT1 in the pathogenesis of cardiomyopathy, the present study identified ALCAT1 as a key regulator of mitophagy and PINK1 expression in the heart. It was demonstrated that the onset of cardiomyopathy dramatically increased the number of mitophagic mitochondria, which is supported by the changes of autophagy biomarkers including the expression of LC3 and p62 proteins. In contrast, ablation of ALCAT1 protected mitochondria from oxidative damage associated with hyperthyroid cardiomyopathy. ALCAT1 deficiency also significantly down-regulated the expression of LC3 concurrently with increased expression of p62 protein. Strikingly, ALCAT1 deficiency dramatically increased the expression of PINK1, which is consistent with a protective role of PINK1 against oxidative stress and cardiomyopathy. These findings are further supported by elevated level of mitophagy and cardiomyopathy in mice with targeted deletion of the TAZ gene whose mutation causes TLCL deficiency in Barth syndrome.

The onset of cardiomyopathy stimulates protein synthesis in the cardiomyocytes by activating the Akt-mTOR and Erk pathways. Activation of Akt signaling pathways protect cells against oxidative stress-induced apoptosis, whereas mTOR activation is required for hypertrophic growth of cardiomyocytes. However, chronic hyperthyroidism causes significant down-regulation of Erk, Akt, and mTOR pathways in the late stage of cardiac failure. Accordingly, treatment with rapamycin prevents the onset of T4-induced cardiomyopathy, whereas targeted inactivation of mTOR in mice leads to severe dilated cardiomyopathy characterized by apoptosis, mitophagy, and mitochondrial swelling. In further support of a role of ALCAT1 in oxidative stress in cardiomyopathy, it was found that chronic oxidative stress significantly impaired T4-induced phosphorylation of Akt and downstream signaling components such as GSK-3β, mTOR, and S6 kinase in H9c2 cells overexpressing ALCAT1 and in mice with hyperthyroidism. Oxidative stress by ALCAT1 in H9c2 cells also caused severe insulin resistance which plays a major role in cardiomyopathy. In contrast, ablation of ALCAT1 prevented the onset of cardiomyopathy and restored Akt-mTOR signaling pathways in the ALCAT1 knockout mice.

Importantly, the present findings have additional implications for future studies to uncover molecular mechanisms underlying the causes of other forms of cardiovascular diseases, such as diabetic cardiomyopathy, ischemic reperfusion, and heart failure, since oxidative stress and pathological CL remodeling have been implicated in the etiology of these pathologic conditions. In support of this hypothesis, ALCAT1 is up-regulated by oxidative stress and by the onset of diabetes and obesity. Targeted inactivation of ALCAT1 prevents mitochondrial dysfunction and the onset of obesity which is a major causative factor for type 2 diabetes and cardiovascular diseases. Development of inhibitors of ALCAT1 will provide a potential treatment for cardiac hypertrophy and other heart diseases, the major cause of fatality in the developed countries.

The Abstract of the disclosure will allow the reader to quickly ascertain the nature of the technical disclosure. It is submitted with the understanding that it will not be used to interpret or limit the scope or meaning of the following claims.

What is claimed is:

1. A method of identifying a modulator of acyl-CoA lysocardiolipin acyltransferase 1 (ALCAT1) expression, function or activity, comprising:
   contacting a biological sample with a test agent;
   measuring (a) expression of hypertrophic markers indicative of cardiomyopathy selected from the group consisting of: brain natriuretic peptide (BNP), β-myosin heavy chain (β-MHC), atrial natriuretic factor (ANF), or ACTA1; (b) expression, function or activity of PTEN-induced putative kinase 1 (PINK1); wherein an inhibitor of ALCAT1 expression, function or activity is identified if the test agent decreases the expression of the hypertrophic markers indicative of cardiomyopathy and if the test agent increases the expression, function or activity of PTEN-induced putative kinase 1 (PINK1) as compared to a baseline control, thereby,
   identifying the ALCAT1 modulator.

2. A method of preventing or treating mitochondrial dysfunction associated with aging related diseases or disorders, comprising: administering to a cell or patient a therapeutically effective amount of an agent that inhibits expression, function, activity or combinations thereof, of a lysocardiolipin acyltransferase 1(ALCAT1), mitochondrial polynucleotides, mitochondrial polypeptides, mitochondrial proteins, mtDNA copy number, mitochondrial mass, mitochondrial morphology, mitochondrial fusion, mtDNA mutation rates, or combinations thereof, and increases expression, function or activity of mitofusin-2 (MFN2) as compared to a baseline control.

3. The method of claim 2, wherein a mitofusin is optionally administered with one or more ALCAT1 inhibitors.

4. The method of claim 3, wherein said inhibitor of ALCAT1 decreases oxidative stress as measured by reactive oxygen species (ROS) as compared to a normal baseline control and/or modulates cardiolipin (CL) structure, function, activity, expression or combinations thereof.

5. The method of claim 3, wherein the disease or disorder associated with mitochondrial dysfunction is selected from the group consisting of: diabetes, obesity, cardiac diseases or disorders, erectile dysfunction, menopause, neurodegenerative diseases or disorders, metabolic diseases or disorders.

6. The method of claim 5, wherein said disease or disorder is Amyotrophic lateral sclerosis (ALS) or Barth syndrome.

* * * * *